United States Patent
DeCorte et al.

(10) Patent No.: US 8,686,152 B2
(45) Date of Patent: Apr. 1, 2014

(54) 4,4-DISUBSTITUTED PIPERIDINE DERIVATIVES USEFUL AS INHIBITORS OF DIPEPTIDYL PEPTIDASE-1 (DPP-1)

(75) Inventors: Bart L. DeCorte, Southampton, PA (US); Renee L. DesJarlais, Saint Davids, PA (US); Yifang Huang, Lansdale, PA (US); Michael H. Parker, Chalfont, PA (US); Dennis J. Hlasta, Doylestown, PA (US)

(73) Assignee: Janssen Pharmaceutica NV (BM)

( * ) Notice: Subject to any disclaimer, the term of this patent is extended or adjusted under 35 U.S.C. 154(b) by 214 days.

(21) Appl. No.: 13/043,609

(22) Filed: Mar. 9, 2011

(65) Prior Publication Data

US 2011/0224209 A1 Sep. 15, 2011

Related U.S. Application Data

(60) Provisional application No. 61/312,310, filed on Mar. 10, 2010.

(51) Int. Cl.
*C07D 409/06* (2006.01)
*C07D 405/06* (2006.01)
*A61K 31/4525* (2006.01)
*A61K 31/4535* (2006.01)

(52) U.S. Cl.
USPC ........... 546/193; 546/212; 546/214; 514/318; 514/326

(58) Field of Classification Search
USPC ................... 546/193, 212, 214; 514/318, 326
See application file for complete search history.

(56) References Cited

U.S. PATENT DOCUMENTS

| 2,851,494 A | 9/1985 | Ehrhart et al. |
| 6,350,760 B1 * | 2/2002 | Bakshi et al. ................ 514/323 |

FOREIGN PATENT DOCUMENTS

| WO | WO 98/50534 | 11/1998 |
| WO | WO 2005/121090 | 12/2005 |
| WO | WO 2007/092681 | 8/2007 |
| WO | WO 2009/074829 | 6/2009 |

OTHER PUBLICATIONS

International Search Report, PCT/US2011/027699, dated May 12, 2011.
Methot, N., et al., "In Vivo Inhibition of Serine Protease Processing Requires a High Fractional Inhibition of Cathepsin C", *Molecular Pharmacology*, (2008), vol. 73, No. 6, pp. 1857-1865.

* cited by examiner

*Primary Examiner* — David K O Dell
(74) *Attorney, Agent, or Firm* — Mary A. Appollina

(57) ABSTRACT

The present invention is directed to 4,4-di-substituted piperidine derivatives, pharmaceutical compositions containing them and their use in the treatment of disorders and conditions modulated by DPP-1.

14 Claims, No Drawings

4,4-DISUBSTITUTED PIPERIDINE DERIVATIVES USEFUL AS INHIBITORS OF DIPEPTIDYL PEPTIDASE-1 (DPP-1)

CROSS REFERENCE TO RELATED APPLICATIONS

This application claims the benefit of U.S. Provisional Application 61/312,301, filed on Mar. 10, 2010, which is incorporated by reference herein in its entirety.

FIELD OF THE INVENTION

The present invention is directed to 4,4-di-substituted piperidine derivatives, pharmaceutical compositions containing them and their use in the treatment of disorders and conditions modulated by DPP-1.

BACKGROUND OF THE INVENTION

Chronic Obstructive Pulmonary Disease (COPD) is characterized by the progressive development of irreversible airflow limitation. COPD consists of chronic obstructive bronchitis, with obstruction of small airways, and emphysema, with enlargement of air spaces and destruction of lung parenchyma, loss of lung elasticity, and closure of small airways. In COPD patients, there were increased numbers of neutrophils, cytotoxic T lymphocytes and macrophages in bronchoalveolar lavage (BAL) airways and lung parenchyma. The presence of these inflammatory cells is correlated well with severity of airway obstruction and alveolar wall destruction. It has been shown that neutrophil elastase; cathepsin G and proteinase 3 can produce emphysema and mucus hypersecretion in lab animals. Granzymes A & B are the neutral serine proteases that are expressed exclusively in the granules of activated cytotoxic T lymphocytes. In COPD the protease-antiprotease balance appears to be tipped in favor of increased proteolysis due to increase in polymorphonuclear neutrophil (PMN)-derived proteases, cathepsins and matrix metalloproteases (MMPs). Therefore, a drug that inhibits all or most of the relevant proteases mentioned above is expected to be effective in the treatment of COPD.

Dipeptidyl Peptidase-1 (DPP-1, cathepsin C) is a member of the lysosomal papain-type cysteine protease family that also includes cathepsin B, K, H, L, O, and S. DPP-1 (MW 200 kd) is composed of a dimer of disulfide-linked heavy and light chains, both from a single protein precursor. DPP-1 mRNA is highly expressed in tissues such as lung, spleen, kidney and liver; in inflammatory cells such as PMN, cytotoxic T lymphocytes, alveolar macrophages and mast cells. The biological function of DPP-1 is to convert inactive proenzymes into active enzyme by removing a dipeptide from N-terminal. The proenzymes that are activated by DPP-1 are PMN-derived proteases, granzymes A & B, chymase and tryptase. Since these enzymes play an important pathological role in COPD, inhibition of DDP-1 by small molecules would be a rational therapeutic intervention for COPD. Additional therapeutic indications for a DPP-1 inhibitor are asthma, rhinitis, and rheumatoid arthritis.

There remains a need for inhibitors of DPP-1 for the treatment of DPP-1 mediated disorders and conditions, including but not limited to rheumatoid arthritis, asthma, chronic obstructive pulmonary disease, sepsis, irritable bowel disease, cystic fibrosis, and abdominal aortic aneurism.

SUMMARY OF THE INVENTION

The present invention is directed to compounds of formula (I)

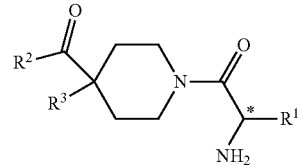

wherein
$R^1$ is selected from the group consisting of $C_{1-4}$alkyl, $C_{2-4}$alkynyl, —$CH_2$—CN, —CH(OH)—$CH_3$, —($C_{1-2}$alkyl)-O—($C_{1-2}$alkyl), —($C_{1-2}$alkyl)-S—($C_{1-2}$alkyl), —($C_{1-2}$alkyl)-SO—($C_{1-2}$alkyl), —($C_{1-2}$alkyl)-$SO_2$—($C_{1-2}$alkyl), —$CH_2$-phenyl, —$CH_2$-(5 to 6 membered heteroaryl) and —CH(OH)-(5 to 6 membered heteroaryl);

wherein the 5 to 6 membered heteroaryl, whether alone or as part of a substituent group, is optionally substituted with a halogen;

$R^2$ is selected from the group consisting of —O-$Q^1$ and —$NR^A$-$Q^1$;

$R^A$ is selected from the group consisting of hydrogen and methyl;

$Q^1$ is selected from the group consisting of hydrogen, $C_{1-4}$alkyl, $C_{3-8}$cycloalkyl, —$CH_2$—($C_{3-8}$cycloalkyl), heterocyclyl and —$CH_2$-(heterocyclyl);

wherein the $C_{3-8}$cycloalkyl or heterocyclyl, whether alone or as part of a substituent group is optionally substituted with one or more substituents independently selected from the group consisting of halogen, hydroxy, $C_{1-4}$alkyl, trifluoromethyl, $C_{1-4}$alkoxy, cyano, amino, ($C_{1-4}$alkyl)amino, di($C_{1-4}$alkyl)amino, —$CO_2H$ and —C(O)—O—($C_{1-4}$alkyl);

alternatively, (when $R^2$ is —$NR^A$-$Q^1$) $R^A$ and $Q^1$ are taken together with the nitrogen atom to which they are bound to form a ring structure selected from the group consisting of piperidinyl, piperazinyl, pyrrolidinyl, morpholinyl, azepinyl, azetadinyl and decahydro-isoquinolin-2-yl;

$R^3$ is selected from the group consisting of
(a) phenyl; wherein the phenyl is optionally substituted with one or more substituents independently selected from the group consisting of halogen, cyano, nitro, $NR^BR^C$, $C_{1-4}$alkyl, trifluoromethyl, $C_{1-4}$alkoxy, —$CO_2H$, —C(O)—$NR^DR^E$, —NH—C(O)—($C_{1-4}$alkyl), —NH—$SO_2$—($C_{1-4}$alkyl), —NH—$SO_2$—$CF_3$ and —NH—$SO_2$—(pyridyl);

wherein $R^B$ and $R^D$ are each independently selected from the group consisting of hydrogen and $C_{1-4}$alkyl;

and wherein $R^D$ is selected from the group consisting of hydrogen and $C_{1-4}$alkyl; and $R^E$ is selected from the group consisting of hydrogen, $C_{1-4}$alkyl, $C_{3-8}$cycloalkyl and phenyl;

(b) —($CH_2$)—$R^4$; wherein $R^4$ is selected from the group consisting of phenyl, pyridyl, pyrimidinyl and thiazolyl;

wherein the phenyl, pyridyl, pyrimidinyl or thiazolyl is optionally substituted with one or more substituents independently selected from the group consisting of halogen, cyano, nitro, $NR^FR^G$, $C_{1-4}$alkyl, trifluoromethyl, $C_{1-4}$alkoxy, —$CO_2H$, —C(O)—$NR^HR^J$, —NH—C(O)—($C_{1-4}$alkyl), —NH—$SO_2$—($C_{1-4}$alkyl), —NH—$SO_2$—$CF_3$ and —NH—$SO_2$—(pyridyl);

wherein $R^F$ and $R^G$ are each independently selected from the group consisting of hydrogen and $C_{1-4}$alkyl;

and wherein $R^H$ is selected from the group consisting of hydrogen and $C_{1-4}$alkyl; and $R^J$ is selected from the group consisting of hydrogen, $C_{1-4}$alkyl, $C_{3-8}$cycloalkyl and phenyl;

alternatively, $R^H$ and $R^J$ are taken together with the nitrogen atom to which they are bound to form a ring structure selected from the group consisting of piperidinyl, piperazinyl, pyrrolidinyl, morpholinyl, azepinyl and azetadinyl;

and (c) —CH$_2$-phenyl-Q$^2$;

wherein Q$^2$ is selected from the group consisting of phenyl, pyridyl, pyrimidinyl, imidazolyl, thiazolyl, triazolyl, tetrazolyl and benzo[d][1,3]dioxolyl;

and wherein the Q$^2$ phenyl or pyridyl is optionally substituted with one or more substituents independently selected from halogen, hydroxy, cyano, C$_{1-4}$alkyl, trifluoromethyl, C$_{1-4}$alkoxy, —NR$^K$R$^L$, —NH—C(O)—(C$_{1-4}$alkyl), —CO$_2$H and —C(O)—O—(C$_{1-4}$alkyl); and wherein R$^K$ and R$^L$ are each independently selected from the group consisting of hydrogen and C$_{1-4}$alkyl;

(wherein the Q$^2$ group is bound to the phenyl at the 2-, 3- or 4-position);

provided that when R$^1$ is —CH(OH)—CH$_3$ and R$^3$ is phenyl, then R$^2$ is other than ethoxy;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by DPP-1 (cathepsin C) (selected from the group consisting of rheumatoid arthritis, asthma, chronic obstructive pulmonary disease, sepsis, irritable bowel disease, cystic fibrosis, and abdominal aortic aneurism) in a subject in need thereof comprising administering to the subject a therapeutically effective amount of any of the compounds or pharmaceutical compositions described above.

Another example of the invention is the use of any of the compounds described herein in the preparation of a medicament for treating: (a) rheumatoid arthritis, (b) asthma, (c) chronic obstructive pulmonary disease, (d) sepsis, (e) irritable bowel disease, (f) cystic fibrosis, or (g) abdominal aortic aneurism, in a subject in need thereof.

In another example, the present invention is directed to a compound as described herein for use in a methods for treating a disorder selected from the group consisting of rheumatoid arthritis, asthma, chronic obstructive pulmonary disease, sepsis, irritable bowel disease, cystic fibrosis, and abdominal aortic aneurism, in a subject in need thereof.

DETAILED DESCRIPTION OF THE INVENTION

The present invention is directed to a process for the preparation of compound of formula (I)

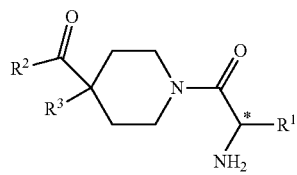

(I)

wherein R$^1$, R$^2$ and R$^3$ are as herein defined, and pharmaceutically acceptable salts thereof. The compounds of formula (I) of the present invention are inhibitors of DPP-1, useful in the treatment of disorders, diseases and conditions mediated by DPP-1 (cathepsin C), including, but not limited to, rheumatoid arthritis, asthma, chronic obstructive pulmonary disease, sepsis, irritable bowel disease, cystic fibrosis, and abdominal aortic aneurism.

In an embodiment of the present invention, R$^1$ is selected from the group consisting of C$_{1-4}$alkyl, C$_{2-4}$alkynyl, —CH$_2$—CN, —CH(OH)—CH$_3$, —(C$_{1-2}$alkyl)-O—(C$_{1-2}$alkyl), —(C$_{1-2}$alkyl)-S—(C$_{1-2}$alkyl), —(C$_{1-2}$alkyl)-SO—(C$_{1-2}$alkyl), —(C$_{1-2}$alkyl)-SO$_2$—(C$_{1-2}$alkyl), —CH$_2$-phenyl, —CH$_2$-(5 to 6 membered heteroaryl) and —CH(OH)-(5 to 6 membered heteroaryl); wherein the 5 to 6 membered heteroaryl, whether alone or as part of a substituent group, is optionally substituted with a halogen. In another embodiment of the present invention, R$^1$ is selected from the group consisting of C$_{1-4}$alkyl, C$_{2-4}$alkynyl, —CH(OH)—CH$_3$, —CH$_2$—CN, —(C$_{1-2}$alkyl)-O—(C$_{1-2}$alkyl), —(C$_{1-2}$alkyl)-S—(C$_{1-2}$alkyl), —(C$_{1-2}$alkyl)-SO—(C$_{1-2}$alkyl), —(C$_{1-2}$alkyl)-SO$_2$—(C$_{1-2}$alkyl), —CH$_2$-phenyl, —CH$_2$-(5 membered heteroaryl) and —CH(OH)-(5 membered heteroaryl); wherein the 5 membered heteroaryl is optionally substituted with a halogen.

In an embodiment of the present invention, R$^1$ is selected from the group consisting of ethyl, n-propyl, n-propyn-2-yl, 1R-hydroxy-ethyl, —CH$_2$—CN, -(methyl)-O-(methyl), -(methyl)-S-(methyl), -(ethyl)-S-(methyl), -(ethyl)-S-(ethyl), -(ethyl)-SO-(ethyl), -(ethyl)-SO$_2$-(ethyl), —CH$_2$-phenyl, —CH$_2$-(fur-2-yl), —CH$_2$-(thien-2-yl), —CH$_2$-(4-bromo-thien-2-yl), —CH$_2$-(5-chloro-thien-2-yl), —CH$_2$-(imidazolyl-4-yl), —CH$_2$-(thiazol-2-yl), —CH$_2$-(pyrazol-1-yl), —CH$_2$-(1,2,4-triazol-1-yl) and —CH(OH)-(thien-2-yl). In another embodiment of the present invention, R$^1$ is selected from the group consisting of —CH$_2$—CN, -(methyl)-S-(methyl), -(ethyl)-S-(methyl), —CH$_2$-(fur-2-yl), —CH$_2$-(thien-2-yl), —CH$_2$-(imidazolyl-4-yl), —CH$_2$-(thiazol-2-yl) and —CH(OH)-(thien-2-yl). In another embodiment of the present invention, R$^1$ is selected from the group consisting of -(ethyl)-S-(methyl), —CH$_2$-(fur-2-yl), —CH$_2$-(thien-2-yl) and —CH$_2$-(thiazol-2-yl). In another embodiment of the present invention, R$^1$ is selected from the group consisting of fur-2-yl-methyl- and thien-2-yl-methyl. In another embodiment of the present invention, R$^1$ is —CH$_2$-(thien-2-yl).

In an embodiment of the present invention, R$^1$ is other than —CH(OH)—CH$_3$.

In an embodiment of the present invention, R$^2$ is selected from the group consisting of —O-Q$^1$ and —NR$^A$-Q$^1$; wherein R$^A$ is selected from the group consisting of hydrogen and methyl; wherein Q$^1$ is selected from the group consisting of hydrogen, C$_{1-4}$alkyl, C$_{3-6}$cycloalkyl, —CH$_2$—(C$_{3-6}$cycloalkyl), 5 to 6 membered heterocyclyl and —CH$_2$-(5 to 6 membered heterocyclyl); wherein the C$_{3-6}$cycloalkyl or 5 to 6 membered heterocyclyl, whether alone or as part of a substituent group is optionally substituted with one to two substituents independently selected from the group consisting of halogen, hydroxy, C$_{1-4}$alkyl, trifluoromethyl, —CO$_2$H and —C(O)—O—(C$_{1-4}$alkyl); alternatively, R$^A$ and Q$^1$ are taken together with the nitrogen atom to which they are bound to form a ring structure selected from the group consisting of piperidinyl, piperazinyl, pyrrolidinyl, morpholinyl and decahydro-isoquinolin-2-yl.

In another embodiment of the present invention, R$^2$ is selected from the group consisting of —OH, —OCH$_3$, —O—CH$_2$—(C$_{5-6}$cycloalkyl) and —NR$^A$-Q$^1$; wherein R$^A$ is selected from the group consisting of hydrogen and methyl; wherein $Q^1$ is selected from the group consisting of $C_{5-6}$cycloalkyl, —$CH_2$—($C_{5-6}$cycloalkyl), 5 to 6 membered saturated heterocyclyl and —$CH_2$-(5 to 6 membered heterocyclyl); wherein the $C_{5-6}$cycloalkyl or 5 to 6 membered heterocyclyl, whether alone or as part of a substituent group is optionally substituted with a substituent selected form the group consisting of hydroxy, $C_{1-2}$alkyl, —$CO_2H$ and —C(O)—O—($C_{1-2}$alkyl); alternatively, $R^A$ and $Q^1$ are taken together with the nitrogen atom to which they are bound to form a ring structure selected form the group consisting of piperidin-1yl, morpholin-4-yl and decahydro-isoquinolin-2-yl.

In another embodiment of the present invention, $R^2$ is selected from the group consisting of hydroxy, methoxy, cyclohexyl-methoxy-, morpholin-4-yl, piperidin-1-yl, decahydro-isoquinolin-2-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-.

In another embodiment of the present invention, $R^2$ is selected from the group consisting of cyclohexyl-methoxy-, piperidin-1-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-. In another embodiment of the present invention, $R^2$ is selected from the group consisting of cyclohexyl-methoxy-, cyclohexyl-amino, cyclohexyl-methyl-amino-, trans-(1-(4-methoxycarbonyl-cyclohexyl)-amino)-, trans-(1-(4-carboxy-cyclohexyl)-amino)-, trans-(1-(4-methoxycarbonyl-cyclohexyl)-amino)-, N-methyl-N-(cyclohexyl-methyl)-amino-, and tetrahydropyran-4-yl-methyl-amino-. In another embodiment of the present invention, $R^2$ is selected from the group consisting of cyclohexyl-amino, cyclohexyl-methyl-amino-, trans-(1-(4-methoxycarbonyl-cyclohexyl)-amino)-, N-methyl-N-(cyclohexyl-methyl)-amino-, and tetrahydropyran-4-yl-methyl-amino-. In another embodiment of the present invention, $R^2$ is selected from the group consisting of cyclohexyl-amino, cyclohexyl-methyl-amino-, trans-(1-(4-methoxycarbonyl-cyclohexyl)-amino)- and N-methyl-N-(cyclohexyl-methyl)-amino-. In another embodiment of the present invention, $R^2$ is selected form the group consisting of cyclohexyl-methyl-amino and cyclohexyl-amino-.

In an embodiment of the present invention, $R^2$ is other than ethoxy. In another embodiment of the present invention, $R^2$ is other than —O—($C_{1-2}$alkyl). In another embodiment of the present invention, $R^2$ is other than —O—($C_{1-4}$alkyl). In another embodiment of the present invention, $R^2$ is other than —O—($C_{2-3}$alkyl).

In an embodiment of the present invention, $R^2$ is —O-$Q^1$. In another embodiment of the present invention, $R^2$ is selected from the group consisting of hydroxy, methoxy and —O—$CH_2$—($C_{5-6}$cycloalkyl). In another embodiment of the present invention, $R^2$ is selected from the group consisting of hydroxy, methoxy and —O—$CH_2$-cyclohexyl. In another embodiment of the present invention, $R^2$ is —O—$CH_2$-cyclohexyl.

In another embodiment of the present invention, $R^2$ is —$NR^A$-$Q^1$. In an embodiment of the present invention, $R^A$ is selected from the group consisting of hydrogen and methyl. In another embodiment of the present invention, $R^A$ is hydrogen.

In an embodiment of the present invention, $R^2$ is —$NR^A$-$Q^1$; wherein $R^A$ is selected from the group consisting of hydrogen and methyl; wherein $Q^1$ is selected from the group consisting of hydrogen, $C_{1-4}$alkyl, $C_{3-6}$cycloalkyl, —$CH_2$—($C_{3-6}$cycloalkyl), 5 to 6 membered heterocyclyl and —$CH_2$-(5 to 6 membered heterocyclyl); wherein the $C_{3-6}$cycloalkyl or 5 to 6 membered heterocyclyl, whether alone or as part of a substituent group is optionally substituted with one to two substituents independently selected from the group consisting of halogen, hydroxy, $C_{1-4}$alkyl, trifluoromethyl, —$CO_2H$ and —C(O)—O—($C_{1-4}$alkyl); alternatively, $R^A$ and $Q^1$ are taken together with the nitrogen atom to which they are bound to form a ring structure selected from the group consisting of piperidinyl, piperazinyl, pyrrolidinyl, morpholinyl and decahydro-isoquinolin-2-yl.

In another embodiment of the present invention, $R^2$—$NR^A$-$Q^1$; wherein $R^A$ is selected from the group consisting of hydrogen and methyl; wherein $Q^1$ is selected from the group consisting of $C_{5-6}$cycloalkyl, —$CH_2$—($C_{5-6}$cycloalkyl), 5 to 6 membered saturated heterocyclyl and —$CH_2$-(5 to 6 membered heterocyclyl); wherein the $C_{5-6}$cycloalkyl or 5 to 6 membered heterocyclyl, whether alone or as part of a substituent group is optionally substituted with a substituent selected form the group consisting of hydroxy, $C_{1-2}$alkyl, —$CO_2H$ and —C(O)—O—($C_{1-2}$alkyl); alternatively, $R^A$ and $Q^1$ are taken together with the nitrogen atom to which they are bound to form a ring structure selected form the group consisting of piperidin-1yl, morpholin-4-yl and decahydro-isoquinolin-2-yl.

In another embodiment of the present invention, $R^2$ is selected from the group consisting of morpholin-4-yl, piperidin-1-yl, decahydro-isoquinolin-2-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-. In another embodiment of the present invention, $R^2$ is selected from the group consisting of piperidin-1-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-. In another embodiment of the present invention, $R^2$ is selected from the group consisting of cyclohexyl-amino, cyclohexyl-methyl-amino-, trans-(1-(4-methoxycarbonyl-cyclohexyl)-amino)-, trans-(1-(4-carboxy-cyclohexyl)-amino)-, trans-(1-(4-methoxycarbonyl-cyclohexyl)-amino)-, N-methyl-N-(cyclohexyl-methyl)-amino-, and tetrahydropyran-4-yl-methyl-amino-.

In an embodiment of the present invention, $R^2$ is —$NR^A$-$Q^1$; wherein $R^A$ and $Q^1$ are taken together with the nitrogen atom to which they are bound to form a ring structure selected from the group consisting of piperidinyl, piperazinyl, pyrrolidinyl, morpholinyl and decahydro-isoquinolin-2-yl. In another embodiment of the present invention, $R^2$ is —$NR^A$-$Q^1$; wherein $R^A$ and $Q^1$ are taken together with the nitrogen atom to which they are bound to form a ring structure selected form the group consisting of piperidin-1yl, morpholin-4-yl and decahydro-isoquinolin-2-yl. In another embodiment of the present invention, $R^2$ is —$NR^A$-$Q^1$; wherein $R^A$ and $Q^1$ are taken together with the nitrogen atom to which they are bound to form piperidin-1yl.

In an embodiment of the present invention, $R^3$ is selected from the group consisting of (a) phenyl; wherein the phenyl is optionally substituted with one to two substituents independently selected from the group consisting of halogen, cyano, nitro, $NR^BR^C$, $C_{1-4}$alkyl, trifluoromethyl, —$CO_2H$ and —$C(O)$—$NR^DR^E$; wherein $R^B$ and $R^C$ are each independently selected from the group consisting of hydrogen and $C_{1-2}$alkyl; and wherein $R^D$ is selected from the group consisting of hydrogen and $C_{1-4}$alkyl; and $R^E$ is selected from the group consisting of hydrogen, $C_{1-4}$alkyl, $C_{3-8}$cycloalkyl and phenyl;

(b) —$(CH_2)$—$R^4$; wherein $R^4$ is selected from the group consisting of phenyl and pyridyl; wherein the phenyl or pyridyl is optionally substituted with one to two substituents independently selected from the group consisting of halogen, cyano, nitro, $NR^FR^G$, $C_{1-4}$alkyl, trifluoromethyl, $C_{1-4}$alkoxy, —$CO_2H$, —$C(O)$—$NR^HR^J$, —$NH$—$C(O)$—$(C_{1-4}$alkyl), —$NH$—$SO_2$—$(C_{1-4}$alkyl), —$NH$—$SO_2$—$CF_3$ and —$NH$—$SO_2$-(pyridyl); wherein $R^F$ and $R^G$ are each independently selected from the group consisting of hydrogen and $C_{1-2}$alkyl; wherein $R^H$ is selected from the group consisting of hydrogen and $C_{1-4}$alkyl; and $R^J$ is selected from the group consisting of hydrogen, $C_{1-4}$alkyl, $C_{3-6}$cycloalkyl and phenyl; alternatively, $R^H$ and $R^J$ are taken together with the nitrogen atom to which they are bound to form a ring structure selected from the group consisting of piperidinyl, piperazinyl, pyrrolidinyl and morpholinyl;

and (c) —$CH_2$-phenyl-$Q^2$; wherein $Q^2$ is selected from the group consisting of phenyl, pyridyl, pyrimidinyl, tetrazolyl and benzo[d][1,3]dioxolyl; and wherein the $Q^2$ phenyl or pyridyl is optionally substituted with one to two substituents independently selected from halogen, hydroxy, cyano, trifluoromethyl, $C_{1-4}$alkoxy, —$NR^KR^L$, —$NH$—$C(O)$—$(C_{1-4}$alkyl), —$CO_2H$ and —$C(O)$—$O$—$(C_{1-4}$alkyl); and wherein $R^K$ and $R^L$ are each independently selected from the group consisting of hydrogen and $C_{1-4}$alkyl.

In another embodiment of the present invention, $R^3$ is selected from the group consisting of (a) phenyl; wherein the phenyl is optionally substituted with one to two substituent independently selected from the group consisting of $C_{1-2}$alkyl and trifluoromethyl;

(b) —$CH_2$—$R^4$; wherein $R^4$ is selected from the group consisting of phenyl and pyridyl; wherein the phenyl is optionally substituted with one to two substituents independently selected from the group consisting of halogen, trifluoromethyl, $C_{1-2}$alkoxy, cyano, nitro, amino, —$CO_2H$, —$C(O)$—$NR^HR^J$, —$NH$—$C(O)$—$(C_{1-2}$alkyl), —$NH$—$SO_2$—$(C_{1-2}$alkyl), —$NH$—$SO_2$—$CF_3$ and —$NH$—$SO_2$-(pyridyl); wherein $R^H$ is selected from the group consisting of hydrogen and $C_{1-2}$alkyl; and $R^J$ is selected from the group consisting of hydrogen, $C_{1-2}$alkyl, $C_{5-6}$cycloalkyl and phenyl; alternatively, $R^H$ and $R^J$ are taken together with the nitrogen atom to which they are bound to form a ring structure selected from the group consisting of pyrrolidinyl and morpholinyl;

and (c) —$CH_2$-(phenyl)-$Q^2$; wherein $Q^2$ is selected from the group consisting of phenyl, pyridyl, pyrimidinyl, tetrazolyl and benzo[d][1,3]dioxolyl; and wherein the $Q^2$ phenyl or pyridyl is optionally substituted with a substituent selected from the group consisting of halogen, hydroxy, cyano, trifluoromethyl, $C_{1-2}$alkoxy, —$NH$—$C(O)$—$(C_{1-2}$alkyl) and $CO_2H$.

In another embodiment of the present invention, $R^3$ is selected from the group consisting of phenyl, 4-methylphenyl, 3,5-di(trifluoromethyl)phenyl, —$CH_2$-phenyl, —$CH_2$-(4-chlorophenyl), —$CH_2$-(3-iodophenyl), —$CH_2$-(4-iodophenyl), —$CH_2$-(2-cyanophenyl), —$CH_2$-(4-cyanophenyl), —$CH_2$-(4-nitrophenyl), —$CH_2$-(4-aminophenyl), —$CH_2$-(4-trifluoromethylphenyl), —$CH_2$-(2-carboxyphenyl), —$CH_2$-(4-carboxyphenyl), —$CH_2$-(3-methoxyphenyl), —$CH_2$-(2,4-difluorophenyl), —$CH_2$-(4-(amino-carbonyl)-phenyl), —$CH_2$-(4-(cyclohexyl-amino-carbonyl)-phenyl), —$CH_2$-(4-(phenyl)amino-carbonyl)-phenyl), —$CH_2$-(4-(dimethyl-amino-carbonyl)-phenyl), —$CH_2$-(4-(morpholin-4-yl-carbonyl)-phenyl), —$CH_2$-(4-(pyrrolidin-1-yl-carbonyl)-phenyl), —$CH_2$-(4-(methyl-sulfonyl-amino)-phenyl), —$CH_2$-(4-(trifluoromethyl-sulfonyl)amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl), —$CH_2$-(pyrid-4-yl), —$CH_2$-(3-(phenyl)-phenyl), —$CH_2$-(4-(phenyl)-phenyl), —$CH_2$-(4-(4-cyanophenyl)-phenyl), —$CH_2$-(4-(3-methoxyphenyl)-phenyl), —$CH_2$-(3-(3-carboxyphenyl)-phenyl), —$CH_2$-(3-(4-carboxyphenyl)-phenyl), —$CH_2$-(4-(3-carboxyphenyl)-phenyl), —$CH_2$-(4-(4-carboxyphenyl)-phenyl), —$CH_2$-(3-(4-trifluoromethyl-phenyl)-phenyl), —$CH_2$-(4-(4-trifluoromethyl-phenyl)-phenyl), —$CH_2$-(4-(2-methyl-carbonyl)amino-phenyl)-phenyl), —$CH_2$-(4-(3-methyl-carbonyl-amino-phenyl)-phenyl), —$CH_2$-(4-(pyrid-3-yl)-phenyl), —$CH_2$-(4-(pyrid-4-yl)-phenyl), —$CH_2$-(4-(2-methoxy-pyrdi-3-yl)-phenyl), —$CH_2$-(4-(6-methoxy-pyrid-3-yl)-phenyl), —$CH_2$-(4-(2-chloro-pyrid-3-yl)-phenyl), —$CH_2$-(3-(6-hydroxy-pyrid-3-yl)-phenyl), —$CH_2$-(4-(6-hydroxy-pyrid-3-yl)-phenyl), —$CH_2$-(3-(pyrimidin-5-yl)-phenyl), —$CH_2$-(4-(pyrimidin-5-yl)-phenyl), —$CH_2$-(4-(tetrazol-5-yl)-phenyl) and —$CH_2$-(4-(benzo[d][1,3]dioxol-5-yl)-phenyl).

In another embodiment of the present invention, $R^3$ is selected from the group consisting of phenyl, 4-methylphenyl, 3,5-di(trifluoromethyl)phenyl, —$CH_2$-phenyl, —$CH_2$-(4-chlorophenyl), —$CH_2$-(3-iodophenyl), —$CH_2$-(4-iodophenyl), —$CH_2$-(2-cyanophenyl), —$CH_2$-(4-cyanophenyl), —$CH_2$-(4-nitrophenyl), —$CH_2$-(4-aminophenyl), —$CH_2$-(4-trifluoromethylphenyl), —$CH_2$-(2-carboxyphenyl), —$CH_2$-(4-carboxyphenyl), —$CH_2$-(3-methoxyphenyl), —$CH_2$-(2,4-difluorophenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-yl-carbonyl)-phenyl), —$CH_2$-(4-(pyrrolidin-1-yl-carbonyl)-phenyl), —$CH_2$-(4-(methyl-sulfonyl-amino)-phenyl), —$CH_2$-(4-(trifluoromethyl-sulfonyl-amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl), —$CH_2$-(pyrid-4-yl), —$CH_2$-(3-(phenyl)-phenyl), —$CH_2$-(4-(phenyl)-phenyl), —$CH_2$-(4-(4-cyanophenyl)-phenyl), —$CH_2$-(4-(3-methoxyphenyl)-phenyl), —CH$_2$-(3-(3-carboxyphenyl)-phenyl), —CH$_2$-(3-(4-carboxyphenyl)-phenyl), —CH$_2$-(4-(3-carboxyphenyl)-phenyl), —CH$_2$-(4-(4-carboxyphenyl)-phenyl), —CH$_2$-(3-(4-trifluoromethyl-phenyl)-phenyl), —CH$_2$-(4-(4-trifluoromethyl-phenyl)-phenyl), —CH$_2$-(4-(2-methyl-carbonyl-amino-phenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl), —CH$_2$-(4-(tetrazol-5-yl)-phenyl) and —CH$_2$-(4-(benzo[d][1,3]dioxol-5-yl)-phenyl).

In another embodiment of the present invention, R$^3$ is selected from the group consisting of phenyl, 4-methylphenyl, 3,5-di(trifluoromethyl)phenyl, —CH$_2$-phenyl, —CH$_2$-(4-chlorophenyl), —CH$_2$-(3-iodophenyl), —CH$_2$-(4-iodophenyl), —CH$_2$-(2-cyanophenyl), —CH$_2$-(4-cyanophenyl), —CH$_2$-(4-nitrophenyl), —CH$_2$-(4-aminophenyl), —CH$_2$-(4-trifluoromethylphenyl), —CH$_2$-(2-carboxyphenyl), —CH$_2$-(4-carboxyphenyl), —CH$_2$-(3-methoxyphenyl), —CH$_2$-(2,4-difluorophenyl), —CH$_2$-(4-(amino-carbonyl)-phenyl), —CH$_2$-(4-(cyclohexyl-amino-carbonyl)-phenyl), —CH$_2$-(4-(phenyl)amino-carbonyl)-phenyl), —CH$_2$-(4-(dimethyl-amino-carbonyl)-phenyl), —CH$_2$-(4-(morpholin-4-yl-carbonyl)phenyl), —CH$_2$-(4-(pyrrolidin-1-yl-carbonyl)-phenyl), —CH$_2$-(4-(methyl-sulfonyl-amino)-phenyl), —CH$_2$-(4-(trifluoromethyl-sulfonyl)amino)-phenyl), —CH$_2$-(4-(pyrid-2-yl-sulfonyl)amino)-phenyl), —CH$_2$-(4-(methyl-carbonyl-amino)-phenyl), —CH$_2$-(pyrid-3-yl), —CH$_2$-(pyrid-4-yl), —CH$_2$-(4-(phenyl)-phenyl), —CH$_2$-(4-(4-cyanophenyl)-phenyl), —CH$_2$-(4-(3-methoxyphenylyphenyl), —CH$_2$-(3-(3-carboxyphenyl)-phenyl), —CH$_2$-(3-(4-carboxyphenyl)-phenyl), —CH$_2$-(4-(3-carboxyphenyl)-phenyl), —CH$_2$-(4-(4-carboxyphenyl)-phenyl), —CH$_2$-(3-(4-trifluoromethyl-phenyl)-phenyl), —CH$_2$-(4-(4-trifluoromethyl-phenyl)-phenyl), –CH$_2$-(4-(2-methyl-carbonyl)amino-phenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-pentyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)phenyl), —CH$_2$-(4-(pyrimidin-5-yl)phenyl), —CH$_2$-(4-(tetrazol-5-yl)-phenyl) and —CH$_2$-(4-(benzo[d][1,3]dioxol-5-yl)-phenyl).

In another embodiment of the present invention, R$^3$ is selected from the group consisting of phenyl, 4-methylphenyl, 3,5-di(trifluoromethyl)phenyl, —CH$_2$-phenyl, —CH$_2$-(3-iodophenyl), —CH$_2$-(4-iodophenyl), —CH$_2$-(4-cyanophenyl), —CH$_2$-(4-nitrophenyl), —CH$_2$-(4-aminophenyl), —CH$_2$-(3-methoxyphenyl), —CH$_2$-(4-(amino-carbonyl)-phenyl), —CH$_2$-(4-(cyclohexyl-amino-carbonyl)-phenyl), —CH$_2$-(4-(phenyl-amino-carbonyl)-phenyl), —CH$_2$-(4-(dimethyl-amino-carbonyl)-phenyl), —CH$_2$-(4-(morpholin-4-yl-carbonyl)-phenyl), —CH$_2$-(4-(pyrrolidin-1-yl-carbonyl)-phenyl), —CH$_2$-(4-(methyl-sulfonyl-amino)-phenyl), —CH$_2$-(4-(pyrid-2-yl-sulfonyl-amino)-phenyl), —CH$_2$-(4-(methyl-carbonyl-amino)-phenyl), —CH$_2$-(pyrid-3-yl), —CH$_2$-(pyrid-4-yl), —CH$_2$-(4-(phenyl)-phenyl), —CH$_2$-(4-(4-cyanophenylyl)-phenyl), —CH$_2$-(4-(3-methoxyphenyl)-phenyl), —CH$_2$-(4-(2-methyl-carbonyl-amino-phenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl), —CH$_2$-(4-(tetrazol-5-yl)-phenyl) and —CH$_2$-(4-(benzo[d][1,3]dioxol-5-yl)-phenyl).

In another embodiment of the present invention, R$^3$ is selected from the group consisting of phenyl, 4-methylphenyl, —CH$_2$-phenyl, —CH$_2$-(4-iodophenyl), —CH$_2$-(4-cyanophenyl), —CH$_2$-(4-nitrophenyl), —CH$_2$-(4-(amino-carbonyl)-phenyl), —CH$_2$-(4-(cyclohexyl-amino-carbonyl)-phenyl), —CH$_2$-(4-(phenyl-amino-carbonyl)-phenyl), —CH$_2$-(4-(morpholin-4-yl-carbonyl)-phenyl), —CH$_2$-(4-(methyl-sulfonyl-amino)-phenyl), —CH$_2$-(4-(pyrid-2-yl-sulfonyl-amino)-phenyl), —CH$_2$-(4-(methyl-carbonyl-amino)-phenyl), —CH$_2$-(pyrid-4-yl), —CH$_2$-(4-(phenyl)-phenyl), —CH$_2$-(4-(4-cyanophenyl)-phenyl), —CH$_2$-(4-(3-methoxyphenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl) and —CH$_2$-(4-(benzo[d][1,3]dioxol-5-yl)-phenyl).

In another embodiment of the present invention, R$^3$ is selected from the group consisting of —CH$_2$-(pyrid-3-yl) and —CH$_2$-(4-(phenyl)-phenyl). In another embodiment of the present invention, R$^3$ is selected from the group consisting of phenyl, 4-methylphenyl, —CH$_2$-(4-cyanophenyl), —CH$_2$-(4-nitrophenyl), —CH$_2$-(4-(pyrid-2-yl-sulfonyl-amino)-phenyl), —CH$_2$-(4-(pyrid-4-yl)-phenyl), —CH$_2$-(4-(6-methoxy-pyrid-3-yl)-phenyl), —CH$_2$-(4-(6-hydroxy-pyrid-3-yl)-phenyl) and —CH$_2$-(4-(pyrimidin-5-yl)-phenyl).

In an embodiment of the present invention, R$^3$ is phenyl; wherein the phenyl is optionally substituted with one or more substituents independently selected from the group consisting of halogen, cyano, nitro, NR$^B$R$^C$, C$_{1-4}$alkyl, trifluoromethyl, C$_{1-4}$alkoxy, —CO$_2$H, —C(O)—NR$^D$R$^E$, —NH—C(O)—(C$_{1-4}$alkyl), —NH—SO$_2$—(C$_{1-4}$alkyl), —NH—SO$_2$—CF$_3$ and —NH—SO$_2$-(pyridyl); wherein R$^B$ and R$^C$ are each independently selected from the group consisting of hydrogen and C$_{1-4}$alkyl; and wherein R$^D$ is selected from the group consisting of hydrogen and C$_{1-4}$alkyl; and R$^E$ is selected from the group consisting of hydrogen, C$_{1-4}$alkyl, C$_{3-8}$cycloalkyl and phenyl.

In another embodiment of the present invention, R$^3$ is phenyl; wherein the phenyl is optionally substituted with one to two substituents independently selected from the group consisting of halogen, cyano, nitro, NR$^B$R$^C$, C$_{1-4}$alkyl, trifluoromethyl, —CO$_2$H and —C(O)—NR$^D$R$^E$; wherein R$^B$ and R$^C$ are each independently selected from the group consisting of hydrogen and C$_{1-2}$alkyl; and wherein R$^D$ is selected from the group consisting of hydrogen and C$_{1-4}$alkyl; and R$^E$ is selected from the group consisting of hydrogen, C$_{1-4}$alkyl, C$_{3-8}$cycloalkyl and phenyl. In another embodiment of the present invention, R$^3$ is (a) phenyl; wherein the phenyl is optionally substituted with one to two substituent independently selected from the group consisting of C$_{1-2}$alkyl and trifluoromethyl. In another embodiment of the present invention, R$^3$ is selected from the group consisting of phenyl, 4-methylphenyl and 3,5-di(trifluoromethyl)phenyl. In another embodiment of the present invention, R$^3$ is selected from the group consisting of phenyl and 4-methylphenyl.

In another embodiment of the present invention, $R^3$ is —$(CH_2)$—$R^4$; wherein $R^4$ is selected from the group consisting of phenyl, pyridyl, pyrimidinyl and thiazolyl; wherein the phenyl, pyridyl, pyrimidinyl or thiazolyl is optionally substituted with one or more substituents independently selected from the group consisting of halogen, cyano, nitro, $NR^F R^G$, $C_{1-4}$alkyl, trifluoromethyl, $C_{1-4}$alkoxy, —$CO_2H$, —$C(O)$—$NR^H R^J$, —NH—$C(O)$—$(C_{1-4}$alkyl), —NH—$SO_2$—$(C_{1-4}$alkyl), —NH—$SO_2$—$CF_3$ and —NH—$SO_2$-(pyridyl); wherein $R^F$ and $R^G$ are each independently selected from the group consisting of hydrogen and $C_{1-4}$alkyl; and wherein $R^H$ is selected from the group consisting of hydrogen and $C_{1-4}$alkyl; and $R^J$ is selected from the group consisting of hydrogen, $C_{1-4}$alkyl, $C_{3-8}$cycloalkyl and phenyl; alternatively, $R^H$ and $R^J$ are taken together with the nitrogen atom to which they are bound to form a ring structure selected from the group consisting of piperidinyl, piperazinyl, pyrrolidinyl, morpholinyl, azepinyl and azetadinyl.

In another embodiment of the present invention, $R^3$ is —$CH_2$—$R^4$; wherein $R^4$ is selected from the group consisting of phenyl and pyridyl; wherein the phenyl or pyridyl is optionally substituted with one to two substituents independently selected from the group consisting of halogen, cyano, nitro, $NR^F R^G$, $C_{1-4}$alkyl, trifluoromethyl, $C_{1-4}$alkoxy, —$CO_2H$, —$C(O)$—$NR^H R^J$, —NH—$C(O)$—$(C_{1-4}$alkyl), —NH—$SO_2$—$(C_{1-4}$alkyl), —NH—$SO_2$—$CF_3$ and —NH—$SO_2$-(pyridyl); where $R^F$ and $R^G$ are each independently selected from the group consisting of hydrogen and $C_{1-2}$alkyl; wherein $R^H$ is selected from the group consisting of hydrogen and $C_{1-4}$alkyl; and $R^J$ is selected from the group consisting of hydrogen, $C_{1-4}$alkyl, $C_{3-6}$cycloalkyl and phenyl; alternatively, $R^H$ and $R^J$ are taken together with the nitrogen atom to which they are bound to form a ring structure selected from the group consisting of piperidinyl, piperazinyl, pyrrolidinyl and morpholinyl.

In another embodiment of the present invention, $R^3$ is —$CH_2$—$R^4$; wherein $R^4$ is selected from the group consisting of phenyl and pyridyl; wherein the phenyl is optionally substituted with one to two substituents independently selected from the group consisting of halogen, trifluoromethyl, $C_{1-2}$alkoxy, cyano, nitro, amino, —$CO_2H$, —$C(O)$—$NR^H R^J$, —NH—$C(O)$—$(C_{1-2}$alkyl), —NH—$SO_2$—$(C_{1-2}$alkyl), —NH—$SO_2$—$CF_3$ and —NH—$SO_2$-(pyridyl); wherein $R^H$ is selected from the group consisting of hydrogen and $C_{1-2}$alkyl; and $R^J$ is selected from the group consisting of hydrogen, $C_{1-2}$alkyl, $C_{5-6}$cycloalkyl and phenyl; alternatively, $R^H$ and $R^J$ are taken together with the nitrogen atom to which they are bound to form a ring structure selected from the group consisting of pyrrolidinyl and morpholinyl.

In another embodiment of the present invention, $R^3$ is selected from the group consisting of —$CH_2$-phenyl, —$CH_2$-(4-chlorophenyl), —$CH_2$-(3-iodophenyl), —$CH_2$-(4-iodophenyl), —$CH_2$-(2-cyanophenyl), —$CH_2$-(4-cyanophenyl), —$CH_2$-(4-nitrophenyl), —$CH_2$-(4-aminophenyl), —$CH_2$-(4-trifluoromethylphenyl), —$CH_2$-(2-carboxyphenyl), —$CH_2$-(4-carboxyphenyl), —$CH_2$-(3-methoxyphenyl), —$CH_2$-(2,4-difluorophenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-yl-carbonyl)-phenyl), —$CH_2$-(4-(pyrrolidin-1-yl-carbonyl)-phenyl), —$CH_2$-(4-(methyl-sulfonyl-amino)-phenyl), —$CH_2$-(4-(trifluoromethyl-sulfonyl-amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl) and —$CH_2$-(pyrid-4-yl).

In another embodiment of the present invention, $R^3$ is selected from the group consisting of —$CH_2$-phenyl, —$CH_2$-(3-iodophenyl), —$CH_2$-(4-iodophenyl), —$CH_2$-(4-cyanophenyl), —$CH_2$-(4-nitrophenyl), —$CH_2$-(4-aminophenyl), —$CH_2$-(3-methoxyphenyl), —$CH_2$-(4-(aminocarbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-yl-carbonyl)phenyl), —$CH_2$-(4-(pyrrolidin-1-yl-carbonyl)-phenyl), —$CH_2$-(4-(methyl-sulfonyl-amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl) and —$CH_2$-(pyrid-4-yl). In another embodiment of the present invention, $R^3$ is selected from the group consisting of —$CH_2$-phenyl, —$CH_2$-(4-iodophenyl), —$CH_2$-(4-cyanophenyl), —$CH_2$-(4-nitrophenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(morpholin-4-yl-carbonyl)phenyl), —$CH_2$-(4-(methyl-sulfonyl-amino)-phenyl), —$CH_2$-(4-(pyrid-2-yl-sulfonyl-amino)-phenyl), —$CH_2$-(4-(methyl-carbonyl-amino)-phenyl) and —$CH_2$-(pyrid-4-yl). In another embodiment of the present invention, $R^3$ is selected from the group consisting of —$CH_2$-(4-cyanophenyl), —$CH_2$-(4-nitrophenyl) and —$CH_2$-(4-(pyrid-2-yl-sulfonyl-amino)-phenyl). In another embodiment of the present invention, $R^3$ is —$CH_2$-(pyrid-3-yl).

In another embodiment of the present invention, $R^3$ is —$CH_2$-phenyl-$Q^2$; wherein the $Q^2$ is selected from the group consisting of phenyl, pyridyl, pyrimidinyl, imidazolyl, thiazolyl, triazolyl, tetrazolyl and benzo[d][1,3]dioxolyl; and wherein the $Q^2$ phenyl or pyridyl is optionally substituted with one or more substituent groups independently selected from halogen, hydroxy, cyano, $C_{1-4}$alkyl, trifluoromethyl, $C_{1-4}$alkoxy, —$NR^K R^L$, —NH—$C(O)$—$(C_{1-4}$alkyl), —$CO_2H$ and —$C(O)$—$O$—$(C_{1-4}$alkyl); and wherein $R^K$ and $R^L$ are each independently selected from the group consisting of hydrogen and $C_{1-4}$alkyl.

In another embodiment of the present invention, $R^3$ is —$CH_2$-phenyl-$Q^2$; wherein $Q^2$ is selected from the group consisting of phenyl, pyridyl, pyrimidinyl, tetrazolyl and benzo[d][1,3]dioxolyl; and wherein the $Q^2$ phenyl or pyridyl is optionally substituted with one to two substituents independently selected from halogen, hydroxy, cyano, trifluoromethyl, $C_{1-4}$alkoxy, —$NR^K R^L$, —NH—$C(O)$—$(C_{1-4}$alkyl), —$CO_2H$ and —$C(O)$—$O$—$(C_{1-4}$alkyl); and wherein $R^K$ and $R^L$ are each independently selected from the group consisting of hydrogen and $C_{1-4}$alkyl. In another embodiment of the present invention, $R^3$ is —$CH_2$-(phenyl)-$Q^2$; wherein $Q^2$ is selected from the group consisting of phenyl, pyridyl, pyrimidinyl, tetrazolyl and benzo[d][1,3]dioxolyl; and wherein the $Q^2$ phenyl or pyridyl is optionally substituted with a substituent selected from the group consisting of halogen, hydroxy, cyano, trifluoromethyl, $C_{1-2}$alkoxy, —NH—C(O)—$(C_{1-2}$alkyl) and $CO_2H$.

In another embodiment of the present invention, $R^3$ is selected from the group consisting of —$CH_2$-(3-(phenyl)-phenyl), —$CH_2$-(4-(phenyl)-phenyl), —$CH_2$-(4-(4-cyanophenyl)-phenyl), —$CH_2$-(4-(3-methoxyphenyl)-phenyl), —$CH_2$-(3-(3-carboxyphenyl)-phenyl), —$CH_2$-(3-(4-carboxyphenyl)-phenyl), —$CH_2$-(4-(3-carboxyphenyl)-phenyl), —$CH_2$-(4-(4-carboxyphenyl)-phenyl), —$CH_2$-(3-(4-trifluoromethyl-phenyl)-phenyl), —$CH_2$-(4-(4-trifluoromethyl-phenyl)-phenyl), —$CH_2$-(4-(2-methyl-carbonyl-amino-phenyl)-phenyl), —$CH_2$-(4-(3-methyl-carbonyl-amino-phenyl)-phenyl), —$CH_2$-(4-(pyrid-3-yl)-phenyl), —$CH_2$-(4-(pyrid-4-yl)-phenyl), —$CH_2$-(4-(2-methoxy-pyrdi-3-yl)-phenyl), —CH₂-(4-(6-methoxy-pyrid-3-yl)-phenyl), —CH₂-(4-(2-chloro-pyrid-3-yl)-phenyl), —CH₂-(3-(6-hydroxy-pyrid-3-yl)-phenyl), —CH₂-(4-(6-hydroxy-pyrid-3-yl)-phenyl), —CH₂-(3-(pyrimidin-5-yl)-phenyl), —CH₂-(4-(pyrimidin-5-yl)-phenyl), —CH₂-(4-(tetrazol-5-yl)-phenyl) and —CH₂-(4-(benzo[d][1,3]dioxol-5-yl)-phenyl).

In another embodiment of the present invention, R³ is selected from the group consisting of —CH₂-(4-(phenyl)-phenyl), —CH₂-(4-(4-cyanophenyl)-phenyl), —CH₂-(4-(3-methoxyphenyl)-phenyl), —CH₂-(3-(3-carboxyphenyl)-phenyl), —CH₂-(3-(4-carboxyphenyl)-phenyl), —CH₂-(4-(3-carboxyphenyl)-phenyl), —CH₂-(4-(4-carboxyphenyl)-phenyl), —CH₂-(3-(4-trifluoromethyl-phenyl)-phenyl), —CH₂-(4-(4-trifluoromethyl-phenyl)-phenyl), —CH₂-(4-(2-methyl-carbonyl-amino-phenyl)-phenyl), —CH₂-(4-(3-methyl-carbonyl-amino-phenyl)-phenyl), —CH₂-(4-(pyrid-3-yl)-phenyl), —CH₂-(4-(pyrid-4-yl)-phenyl), —CH₂-(4-(2-methoxy-pyrdi-3-yl)-phenyl), —CH₂-(4-(6-methoxy-pyrid-3-yl)-phenyl), —CH₂-(4-(2-chloro-pyrid-3-yl)-phenyl), —CH₂-(3-(6-hydroxy-pyrid-3-yl)-phenyl), —CH₂-(4-(6-hydroxy-pyrid-3-yl)-phenyl), —CH₂-(3-(pyrimidin-5-yl)-phenyl), —CH₂-(4-(pyrimidin-5-yl)-phenyl), —CH₂-(4-(tetrazol-5-yl)-phenyl) and —CH₂-(4-(benzo[d][1,3]dioxol-5-yl)-phenyl). In another embodiment of the present invention, R³ is selected from the group consisting of —CH₂-(4-(phenyl)-phenyl), —CH₂-(4-(4-cyanophenyl)-phenyl), —CH₂-(4-(3-methoxyphenyl)-phenyl), —CH₂-(4-(2-methyl-carbonyl-amino-phenyl)-phenyl), —CH₂-(4-(3-methyl-carbonyl-amino-phenyl)-phenyl), —CH₂-(4-(pyrid-3-yl)-phenyl), —CH₂-(4-(pyrid-4-yl)-phenyl), —CH₂-(4-(2-methoxy-pyrdi-3-yl)-phenyl), —CH₂-(4-(6-methoxy-pyrid-3-yl)-phenyl), —CH₂-(4-(2-chloro-pyrid-3-yl)-phenyl), —CH₂-(3-(6-hydroxy-pyrid-3-yl)phenyl), —CH₂-(4-(6-hydroxy-pyrid-3-yl)-phenyl), —CH₂-(3-(pyrimidin-5-yl)phenyl), —CH₂-(4-(pyrimidin-5-yl)phenyl), —CH₂-(4-(tetrazol-5-yl)-phenyl) and —CH₂-(4-(benzo[d][1,3]dioxol-5-yl)-phenyl).

In another embodiment of the present invention, R³ is selected from the group consisting of —CH₂-(4-(phenyl)-phenyl), —CH₂-(4-(4-cyanophenyl)-phenyl), —CH₂-(4-(3-methoxyphenyl)-phenyl), —CH₂-(4-(3-methyl-carbonyl-amino-phenyl)-phenyl), —CH₂-(4-(pyrid-3-yl)-phenyl), —CH₂-(4-(pyrid-4-yl)-phenyl), —CH₂-(4-(2-methoxy-pyrdi-3-yl)-phenyl), —CH₂-(4-(6-methoxy-pyrid-3-yl)-phenyl), —CH₂-(4-(2-chloro-pyrid-3-yl)-phenyl), —CH₂-(3-(6-hydroxy-pyrid-3-yl)-phenyl), —CH₂-(4-(6-hydroxy-pyrid-3-yl)-phenyl), —CH₂-(3-(pyrimidin-5-yl)-phenyl), —CH₂-(4-(pyrimidin-5-yl)-phenyl) and —CH₂-(4-(benzo[d][1,3]dioxol-5-yl)-phenyl). In another embodiment of the present invention, R³ is selected from the group consisting of —CH₂-(4-(pyrid-4-yl)phenyl), —CH₂-(4-(6-methoxy-pyrid-3-yl)-phenyl), —CH₂-(4-(6-hydroxy-pyrid-3-yl)-phenyl) and —CH₂-(4-(pyrimidin-5-yl)-phenyl). In another embodiment of the present invention, R³ is —CH₂-(4-(phenyl)-phenyl).

In an embodiment of the present invention, R³ is other than phenyl.

In an embodiment, the present invention is directed to compounds of formula (I) wherein the stereo-center denoted with the "*" symbol is present in (R) configuration. Preferably, the compound of formula (I) is present in the (R) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

In an embodiment, the present invention is directed to compounds of formula (I) wherein the stereo-center denoted with the "*" symbol is present in (S) configuration. Preferably, the compound of formula (I) is present in the (S) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

Additional embodiments of the present invention, include those wherein the substituents selected for one or more of the variables defined herein (i.e. $R^1$, $R^2$, $R^3$, etc.) are independently selected to be any individual substituent or any subset of substituents selected from the complete list as defined herein. In another embodiment of the present invention is any single compound or subset of compounds selected from the representative compounds listed in Tables 1 to 3, below.

Representative compounds of formula (I) of the present invention are as listed in Tables 1 to 3, below. Unless otherwise noted, the compounds of the present invention listed in Tables 1 to 3, below, were prepared in an enantiomeric excess of the stereo-isomer wherein the amino group bound to the —CH—R¹ is present in the down orientation. Unless otherwise noted, said stereo-isomer is the corresponding (S)-enantiomer.

TABLE 1

Representative Compounds of Formula (I)

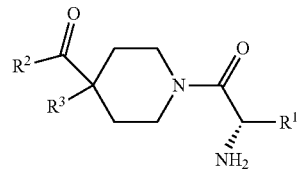

| ID No | R¹ | R² | R³ |
|---|---|---|---|
| 69 | thien-2-yl-methyl | cyclohexyl-amino- | phenyl |
| 70 | ethyl | cyclohexyl-amino- | phenyl |
| 75 | imidazol-4-yl-methyl | cyclohexyl-amino- | phenyl |
| 85 | thien-2-yl-methyl | trans-(1-(4-hydroxy-cyclohexyl)-amino- | phenyl |
| 91 | thien-2-yl-methyl | cylohexyl-methyl-amino- | phenyl |
| 103 | thien-2-yl-methyl | tetrahydro-pyrany-4-yl-amino- | phenyl |
| 104 | thien-2-yl-methyl | tetrahydro-pyrany-4-yl-methyl-amino- | phenyl |
| 109 | thien-2yl-methyl | trans-(1-(4-methoxycarbonyl-cyclohexyl)-amino)- | phenyl |
| 110 | thien-2-yl-methyl | trans-(1-(4-methoxycarbonyl-cyclohexyl)-methyl-amino)- | phenyl |
| 111 | thien-2-yl-methyl | trans-(1-(4-carboxy-cyclohexyl)-amino)- | phenyl |
| 112 | thien-2-yl-methyl | trans-1-((4-carboxy-cyclohexyl)-methyl-amino)- | phenyl |
| 113 | thien-2-yl-methyl | trans-(1-(4-methoxycarbonyl-cyclohexyl)-amino)- | phenyl |
| 114 | thien-2-yl-methyl | 4,5-dihydro-thiazol-2-yl-amino- | phenyl |
| 115 | thien-2-yl-methyl | trans-(1-(4-carboxy-cyclohexyl)-amino)- | phenyl |
| 120 | thien-2-yl-methyl | trans-(1-(4-hydroxy-cyclohexyl)-amino)- | 3,5-di(trifluoromethyl)-phenyl |
| 129 | thien-2-yl-methyl | cyclohexyl-methyl-amino- | 4-methyl-phenyl |

TABLE 1-continued

Representative Compounds of Formula (I)

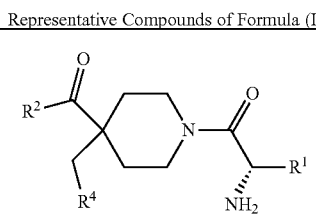

| ID No | R¹ | R² | R³ |
|---|---|---|---|
| 130 | thien-2-yl-methyl | tetrahydropyran-4-yl-methyl-amino- | 4-methyl-phenyl |
| 131 | thien-2-yl-methyl | 4-hydroxy-cyclohexyl-amino- | 4-methyl-phenyl |
| 133 | thien-2-yl-methyl | cyclohexyl-methyl-amino- | 3,5-di(trifluoromethyl)-phenyl |
| 134 | thien-2-yl-methyl | N-(cyclohexyl-methyl)-N-methyl-amino- | phenyl |
| 138 | ethyl | cyclohexyl-methyl-amino- | phenyl |
| 139 | 1R-hydroxy-ethyl | cyclohexyl-methyl-amino- | phenyl |
| 152 | thien-2-yl-methyl | 1-methyl-piperidin-4-yl-methyl-amino- | phenyl |

TABLE 2

Representative Compounds of Formula (I)

| ID No | R¹ | R² | R⁴ |
|---|---|---|---|
| 10 | ethyl | cyclohexyl-methoxy- | phenyl |
| 11 | thien-2-yl-methyl | cyclohexyl-methoxy- | phenyl |
| 12 | imidazol-4-yl-methyl | cyclohexyl-methoxy- | phenyl |
| 13 | ethyl | cyclohexyl-methoxy- | 4-chlorophenyl |
| 14 | thien-2-yl-methyl | cyclohexyl-methoxy- | 4-chlorophenyl |
| 15 | thien-2-yl-methyl | cyclohexyl-methoxy- | 4-cyanophenyl |
| 16 | imidazol-4-yl-methyl | cyclohexyl-methoxy- | 4-cyanophenyl |
| 17 | ethyl | cyclohexyl-methoxy- | 4-cyanophenyl |
| 18 | ethyl | cyclohexyl-methoxy- | 4-trifluoromethyl-phenyl |
| 19 | thien-2-yl-methyl | cyclohexyl-methoxy- | 4-trifluoromethyl-phenyl |
| 20 | imidazol-4-yl-methyl | cyclohexyl-methoxy- | 4-trifluoromethyl-phenyl |
| 21 | ethyl | cyclohexyl-methoxy- | pyrid-4-yl |
| 22 | thien-2-yl-methyl | cyclohexyl-methoxy- | pyrid-4-yl |
| 23 | ethyl | cyclohexyl-methoxy- | pyrid-3-yl |
| 24 | thien-2-yl-methyl | cyclohexyl-methoxy- | pyrid-3-yl |
| 25 | imidazol-4-yl-methyl | cyclohexyl-methoxy- | pyrid-3-yl |
| 26 | ethyl | cyclohexyl-methoxy- | 2,4-difluorophenyl |
| 27 | thien-2-yl-methyl | cyclohexyl-methoxy- | 2,4-difluorophenyl |
| 28 | imidazol-4-yl-methyl | cyclohexyl-methoxy- | 2,4-difluorophenyl |
| 41 | thien-2-yl-methyl | cyclohexyl-amino- | 4-iodophenyl |
| 56 | thien-2-yl-methyl | cyclohexyl-amino- | 4-(cyclohexyl-amino-carbonyl)-phenyl |
| 57 | thien-2-yl-methyl | cyclohexyl-amino- | 4-(morpholin-4-yl-carbonyl)-phenyl |
| 58 | thien-2-yl-methyl | cyclohexyl-amino- | 4-(pyrrolidin-1-yl-carbonyl)-phenyl |
| 59 | thien-2-yl-methyl | cyclohexyl-amino- | 4-(dimethyl-amino-carbonyl)-phenyl |
| 60 | thien-2-yl-methyl | cyclohexyl-amino- | 4-(phenyl-amino-carbonyl)-phenyl |
| 61 | thien-2-yl-methyl | cyclohexyl-amino- | 4-(amino-carbonyl)-phenyl |
| 62 | thien-2-yl-methyl | cyclohexyl-amino- | 4-carboxyphenyl |
| 66 | thien-2-yl-methyl | cyclohexyl-amino- | pyrid-3-yl |
| 67 | ethyl | cyclohexyl-amino- | pyrid-3-yl |
| 68 | imidazol-4-yl-methyl | cyclohexyl-amino- | pyrid-3-yl |
| 71 | thien-2-yl-methyl | cyclohexyl-amino- | pyrid-4-yl |
| 72 | ethyl | cyclohexyl-amino- | pyrid-4-yl |
| 73 | methylthio-ethyl | cyclohexyl-amino- | 4-iodophenyl |
| 74 | ethyl-sulfonyl-ethyl | cyclohexyl-amino- | 4-iodophenyl |
| 77 | ethyl | cyclohexyl-amino- | 4-iodophenyl |
| 79 | imidazol-4-yl-methyl | cyclohexyl-amino- | 4-nitrophenyl |
| 80 | thien-2-yl-methyl | cyclohexyl-amino- | 2-carboxyphenyl |
| 81 | thien-2-yl-methyl | cyclohexyl-amino- | 4-nitrophenyl |
| 82 | thien-2-yl-methyl | cyclohexyl-amino- | 2-cyanophenyl |
| 83 | ethyl | cyclohexyl-amino- | 3-methoxy-phenyl |
| 84 | thien-2-yl-methyl | cyclohexyl-amino- | 3-methoxy-phenyl |
| 86 | thien-2-yl-methyl | cyclohexyl-amino- | phenyl |
| 87 | thien-2-yl-methyl | cyclohexyl-amino- | 4-(pyrid-2-yl-sulfonyl-amino)-phenyl |
| 88 | thien-2-yl-methyl | cyclohexyl-amino- | 4-(methyl-sulfonyl-amino)-phenyl |
| 89 | thien-2-yl-methyl | cyclohexyl-amino- | 4-(trifluoromethyl-sulfonyl-amino)-phenyl |
| 90 | thien-2-yl-methyl | cyclohexyl-amino- | 4-(methyl-carbonyl-amino)-phenyl |
| 92 | 4-bromo-thien-2-yl-methyl | cyclohexyl-amino- | 4-iodophenyl |
| 95 | thien-2-yl-methyl | cyclohexyl-amino- | 4-aminophenyl |
| 96 | thien-2-yl-methyl | cyclohexyl-amino- | 3-iodophenyl |
| 116 | thien-2-yl-methyl | cyclohexyl-methyl-amino- | 4-amino-carbonyl-phenyl |
| 117 | thien-2-yl-methyl | 4-hydroxy-cyclohexyl-amino- | 4-amino-carbonyl-phenyl |
| 121 | thien-2-yl-methyl | tetrahydro-pyran-4-yl-methyl-amino- | pyrid-4-yl |
| 122 | thien-2-yl-methyl | morpholin-4-yl | pyrid-4-yl |
| 124 | thien-2-yl-methyl | cyclohexyl-methyl-amino- | 4-cyanophenyl |
| 125 | thien-2-yl-methyl | 4-hydroxy-cyclohexyl-amino- | 4-cyanophenyl |
| 136 | n-propyl | cyclohexyl-methyl-amino- | pyrid-3-yl |

TABLE 3

Representative Compounds of Formula (I)

| ID No | R¹ | R² | Q² |
|---|---|---|---|
| 1 | thien-2-yl-methyl | methoxy | 4-phenyl |
| 2 | thien-2-yl-methyl | hydroxy | 4-phenyl |
| 3 | thien-2-yl-methyl | cyclohexyl-methyl-amino | 4-phenyl |
| 4 | thien-2-yl-methyl | piperidin-1-yl | 4-phenyl |
| 5 | ethyl | cyclohexyl-methyl-amino | 4-phenyl |
| 6 | thien-2-yl-methyl | tetrahydro-pyan-4-yl-methyl-amino- | 4-phenyl |
| 7 | thien-2-yl-methyl | decahydro-isoquinolin-2-yl | 4-phenyl |
| 8 | thien-2-yl-methyl | cyclohexyl-amino- | 4-phenyl |
| 9 | imidazol-4-yl-methyl | cyclohexyl-methyl-amino- | 4-phenyl |
| 29 | ethyl | cyclohexyl-methoxy- | 3-phenyl |
| 30 | thien-2-yl-methyl | cyclohexyl-methoxy- | 3-phenyl |
| 31 | imidazol-4-yl-methyl | cyclohexyl-methoxy- | 3-phenyl |
| 32 | 1,2,4-triazol-1-yl-methyl | cyclohexyl-amino- | 4-phenyl |
| 33 | thiazol-2-yl-methyl | cyclohexyl-amino- | 4-phenyl |
| 34 | pyrazol-1-yl-methyl | cyclohexyl-amino- | 4-phenyl |
| 35 | n-propyn-2-yl | cyclohexyl-amino- | 4-phenyl |
| 36 | cyano-methyl- | cyclohexyl-amino- | 4-phenyl |
| 37 | fur-2-yl-methyl | cyclohexyl-amino- | 4-phenyl |
| 38[b] | methylthio-methyl- | cyclohexyl-amino- | 4-phenyl |
| 39 | methoxy-methyl- | cyclohexyl-amino- | 4-phenyl |
| 40 | thien-2-yl-methyl | cyclohexyl-amino- | 4-(benzo[d][1,3]dioxol-5-yl) |
| 42 | thien-2-yl-methyl | cyclohexyl-amino- | 4-(pyrid-4-yl) |
| 43 | thien-2-yl-methyl | cyclohexyl-amino- | 4-(pyrimidin-5-yl) |
| 44 | thien-2-yl-methyl | cyclohexyl-amino- | 4-(6-methoxy-pyrid-3-yl) |
| 45 | thien-2-yl-methyl | cyclohexyl-amino- | 4-(2-methyl-carbonyl-amino-phenyl) |
| 46 | thien-2-yl-methyl | cyclohexyl-amino- | 4-(2-methoxy-pyrid-3-yl) |
| 47 | thien-2-yl-methyl | cyclohexyl-amino- | 4-(3-methoxy-phenyl) |
| 48 | thien-2-yl-methyl | cyclohexyl-amino- | 4-(2-chloro-pyrid-3-yl) |
| 49 | thien-2-yl-methyl | cyclohexyl-amino- | 4-(6-hydroxy-pyrid-3-yl) |
| 50 | thien-2-yl-methyl | cyclohexyl-amino- | 4-(pyrid-3-yl) |
| 51 | thien-2-yl-methyl | cyclohexyl-amino- | 4-(4-cyano-phenyl) |
| 52 | thien-2-yl-methyl | cyclohexyl-amino- | 4-(4-carboxy-phenyl) |
| 53 | thien-2-yl-methyl | cyclohexyl-amino- | 4-(4-trifluoro-methyl-phenyl) |
| 54 | thien-2-yl-methyl | cyclohexyl-amino- | 4-(3-methyl-carbonyl-amino-phenyl) |
| 55 | thien-2-yl-methyl | cyclohexyl-amino- | 4-(3-carboxy-phenyl) |
| 78 | 5-chloro-thien-2-yl-methyl | cyclohexyl-amino- | 4-phenyl |
| 97 | thien-2-yl-methyl | cyclohexyl-amino- | 3-(pyrimidin-5-yl) |
| 98 | thien-2-yl-methyl | cyclohexyl-amino- | 3-(6-hydroxy-pyrid-3-yl) |
| 99 | thien-2-yl-methyl | cyclohexyl-amino- | 4-(4-cyano-phenyl) |
| 100 | thien-2-yl-methyl | cyclohexyl-amino- | 3-(4-trifluoro-methyl-phenyl) |
| 101 | thien-2-yl-methyl | cyclohexyl-amino- | 3-(3-carboxy-phenyl) |
| 102 | thien-2-yl-methyl | cyclohexyl-amino- | 3-(4-carboxy-phenyl) |
| 106 | ethyl-thio-ethyl | cyclohexyl-methyl-amino- | 4-phenyl |
| 107 | ethyl-SO-ethyl | cyclohexyl-methyl-amino- | 4-phenyl |
| 108 | benzyl | cyclohexyl-methyl-amino- | 4-phenyl |
| 123 | 1-hydroxy-1-(thien-2-yl)-methyl | cyclohexyl-methyl-amino- | 4-phenyl |
| 126 | thien-2-yl-methyl | cyclohexyl-amino- | 4-(tetrazol-5-yl) |
| 127 | thien-2-yl-methyl | cyclohexyl-methyl-amino- | 4-(tetrazol-5-yl) |
| 128 | thien-2-yl-methyl | 4-hydroxy-cyclohexyl-amino- | 4-(tetrazol-5-yl) |

[b]For this compound, the amine group, bound to the —CH—R¹ portion of the compound of formula (I) is present in a "down" orientation as drawn, however, due to the nature of the R¹ substituent group and stereo-orientation naming convention, said the stereo-center is defined as being present in the (R) configuration.

Additionally, compound #118, whose structure is shown below (#118)

wherein R¹ is thien-2-yl-methyl- and R³ is 3,5-di(trifluoromethyl)-phenyl), was prepared as an intermediate in the synthesis of compound #120 and compound #133.

In an embodiment, the present invention is directed to compounds of formula (I) whose $IC_{50}$, measured according to the procedure described in Biological Example 1, is less than or equal to about 10 μM, preferably less than or equal to about 5.0 μM, more preferably less than or equal to about 1.0 μM, more preferably less than or equal to about 0.5 μM, more preferably less than or equal to about 0.1 μM.

As used herein, "halogen" shall mean chlorine, bromine, fluorine and iodine.

As used herein, the term "$C_{1-4}$alkyl" whether used alone or as part of a substituent group, shall include straight and branched carbon chain compositions of one to four carbon atoms. For example, $C_{1-4}$alkyl radicals include methyl, ethyl, propyl, isopropyl, butyl, isobutyl, sec-butyl and t-butyl. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, the term "$C_{2-4}$alkynyl" whether used alone or as part of a substituent group, shall include straight and branched carbon chain compositions of two to four carbon atoms, further containing one or more, preferably one, unsaturated triple bond. For example, alkynyl radicals include ethynyl, n-propyn-2-yl, n-butyn-2-yl, and the like.

As used herein, the term "$C_{1-4}$alkoxy" whether used alone or as part of a substituent group, shall denote an oxygen ether radical of any of the above described straight and branched carbon chain compositions of one to four carbon atoms. For example, alkoxy radicals include methoxy, ethoxy, propoxy, isopropoxy, n-butoxy, isobutoxy, sec-butoxy and t-butoxy As used herein, unless otherwise noted, the term "$C_{3-8}$cycloalkyl" shall mean any stable 3-6 membered monocyclic, saturated ring system, for example cyclopropyl, cyclobutyl, cyclopentyl, cyclohexyl, cycloheptyl and cyclooctyl. Preferably, the $C_{3-8}$cycloalkyl is selected from the group consisting of cyclopentyl and cyclohexyl, more preferably the $C_{3-8}$cycloalkyl is cyclohexyl.

As used herein, unless otherwise noted, "5 to 6 membered heteroaryl" shall denote any five or six membered, monocyclic aromatic ring structure containing at least one heteroatom selected from the group consisting of O, N and S, optionally containing one to three additional heteroatoms independently selected from the group consisting of O, N and S. The 5 to 6 membered heteroaryl group may be attached at any heteroatom or carbon atom of the ring such that the result is a stable structure. Examples of suitable heteroaryl groups include, but are not limited to, furyl, thienyl, pyrrolyl, oxazolyl, thiazolyl, pyrazolyl, imidazolyl, isoxazolyl, isothiazolyl, triazolyl, thiadiazolyl, tetrazolyl, pyridyl, pyridazinyl, pyrimidinyl, pyrazinyl, pyranyl, and the like. Preferred heteroaryl groups include, but are not limited to, furyl, thienyl, imidazolyl, thiazolyl, pyrazolyl and triazolyl (for example, 1,2,4-triazolyl).

As used herein, the term "heterocyclyl" shall denote any five to seven membered monocyclic, saturated, partially unsaturated or aromatic ring structure containing at least one heteroatom selected from the group consisting of O, N and S, optionally containing one to three additional heteroatoms independently selected from the group consisting of O, N and S; or any nine to ten membered saturated, partially unsaturated, partially aromatic (including benzo-fused) or aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure. Examples of suitable heterocyclyl groups include, but are not limited to, furyl, thienyl, pyrrolyl, pyrrolidinyl, pyrrolinyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, tetrazolyl, pyranyl, tetrahydropyranyl, pyridyl, piperidinyl, piperazinyl, dioxanyl, morpholinyl, thiomorpholinyl, pyridazinyl, pyrimidinyl, pyrazinyl, triazinyl, indolyl, indolizinyl, isoindolinyl, indolinyl, benzofuryl, benothienyl, indazolinyl, benzimidazolyl, benzthiazolyl, purinyl, quinolizinyl, quinolinyl, isoquinolinyl, cinnolinyl, quinazolinyl, quinoxalinyl, pteridinyl, 1H-pyrazolo[3,4-d]pyrimidinyl, benzo[d][1,3]dioxolyl, 2,3-dihydrobenzofuryl, 1,2,3,4-tetrahydroquinolinyl, 4,5-dihydro-thiazolyl, and the like. Preferred heterocyclyl groups include, but are not limited to, furyl, thienyl, imidazolyl, thiazolyl, pyrazolyl, triazolyl, tetrazolyl, pyrrolidinyl, piperidinyl, piperazinyl, morpholinyl, tetrahydropyranyl, isoquinolinyl, pyridyl, pyrimidinyl and benzo[d][1,3]dioxolyl, When a particular group is "substituted", said group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

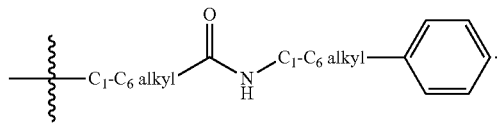

Abbreviations used in the specification, particularly the Schemes and Examples, are as follows:

| | |
|---|---|
| Boc or BOC = | tert-Butoxycarbonyl |
| BOP-Cl = | Benzotriazol-1-yloxy-tris(dimethylamino)phosphoniium hexafluorophosphate chloride |
| Cbz or CBz = | Benzyloxy-carbonyl- |
| COPD = | Chronic ObstructivePulmonary Disease |
| DCC = | N,N'-Dicyclohexylcarbodiimide |
| DCE = | 1,2-Dichloroethene |
| DCM = | Dichloromethane |

| | |
|---|---|
| DIPEA or DIEA = | Diisopropylethylamine |
| DMAP = | 4-N,N-Dimethylaminopyridine |
| DME = | 1,2-Dimethoxyethane |
| DMF = | N,N-Dimethylformamide |
| DMSO = | Dimethylsulfoxide |
| DPP-1 = | Dipeptidyl Peptidase-1 (Cathepsin C) |
| DTT = | Dithiothreitol |
| EtOAc = | Ethyl Acetate |
| GR-AMC = | Glycine-Arginine-amino-4-methyl-coumain |
| GSH = | Glutathione |
| HATU = | O-(7-Azabenzotriazol-1-yl)-N,N,N'',N''-Tetramethyl Uronium Hexafluorophosphate |
| HBTU = | O-(1H-Benzotriazol-1-yl)-N,N,N',N'-tetramethyluronium hexafluorophosphate |
| HEPES = | 4-(2-Hydroxyethyl)-1-Piperizine Ethane Sulfonic Acid |
| HPLC = | High Pressure Liquid Chromatography |
| LDA = | Lithium Diethylamide |
| LHMDS = | Lithium bis(trimethylsilyl)amide |
| MOM = | Methoxymethyl |
| MTBE = | Methyl tert-butyl ether |
| TEA = | Triethylamine |
| TFA = | Trifluoroacetic Acid |
| THF = | Tetrahydrofuran |
| THP = | Tetrahydropyranyl |
| TMS = | Trimethylsilyl |

As used herein, unless otherwise noted, the term "isolated form" shall mean that the compound is present in a form which is separate from any solid mixture with another compound(s), solvent system or biological environment. In an embodiment, the compound of formula (I) is prepared as an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the compound of formula (I) is present as a substantially pure compound.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "DPP-1 mediated disorder" shall include any condition, disease or disorder which may be mediated through inhibition of DPP-1 activity. One skilled in the art will recognize that disorders mediated by DPP-1 include, but are not limited to (a) disorders of the respiratory tract: including obstructive diseases of the airways including asthma, including bronchial, allergic, intrinsic, extrinsic, exercise-induced, drug induce (including aspirin and NSAID-induced) and dust induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sacroidosis; farmer's lung and related diseases; hypersensitive pnemonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vascullitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

(b) skin disorders: psoriasis, atopic dermatitis, contact dermatitis or other eczematous deramtoses, and delayed-type hypersensitivity reactions; phyto- and photodermatitis; seborrhoeic dermatistis, dermatitis herptiformis, lichen planus, lichen slerosus et atrophica, pyoderma gangrenosum, skin sarcoid, discoid lupus erythematosus, pemphigus, pemphigoid, epidermolysis bullosa, urticaria, angioderma, vasculitides, toxido erythmas, cutaceous eosinopiliass, alopecia areata, male-pattern baldness, Sweet's syndrome, Weber-Christian syndrome, erythema multiforma; cellulitis, both infective and non-infective; panniculitis; cutaceous lymphomas, non-melanoma skin cancer and other dysplastic lesions; drug-induced disorders including fixed-drug eruptions;

(c) eye disorders: blepharitis, conjunctivitis, including perennial and vernal allergic conjunctivitis; iritis; anterior and posterior uveitis; choroiditis; autoimmune, degenerative or inflammatory disorders affecting the retina; opthalmitis including sympathetic opthalmitis; sarcoidosis; infections including viral, fugal and bacterial;

(d) genitourinary disorders: nephritis including interstitial and glomerulnephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction;

(e) allograft rejection disorders: acute and chronic following, for example, transplantation of kidney, heart, liver, lung, bone marrow, skin or cornea or following blood transfusion; or chronic graft versus host disease;

(f) auto-immune and allergic disorders including rheumatoid arthritis, irritable bowel syndrome, systemic lupus erythematosus, multiple sclerosis, Hashimoto's thyroiditis, Grave's disease, Addison's disease, diabetes mellitus, idiopathic thrombocytopaenic purpura, eosinophilic fasciitis, hyper-IgE syndrome, antiphospholipid syndrome and Sazary syndrome;

(g) cancers: including treatment of common cancers including prostate, breast, lung, ovarian, pancreatic, bowel and colon, stomach, skin and brain tumors and malignancies affecting the bone marrow (including leukaemias) and lymphoproliferative systems, such as Hodgkin's and non-Hodgkin's lymphoma; including the prevention and treatment of metastatic disease and tumor recurrences, and paraneoplstic syndrome; and (h) infectious diseases: viral diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoser virus (VZV), rhinovirus, adenovirus, coronavirus, influenza, para-influenza; bacterial diseases such as tubercuavium, leprosy; other infectious diseases such as fungal diseases, Chlamydia, candida, aspergillus, cryptococcal meningitis, pneumocystis carnii, cryptosporidiosis, histoplasmosis, toxoplasmosis, trypanosome infection and leishmaniasis.

In another embodiment, the present invention is directed to methods for the treatment and/or prevention of a DDP-1 mediated disorder; wherein the DPP-1 mediated disorder is selected from the group consisting of chronic obstructive pulmonary disease (COPD), asthma, acute lung injury, adult respiratory distress syndrome, abdominal or thoracic aneurism, rheumatoid arthritis, osteoarthritis, multiple sclerosis, sepsis and taxoplasmosis.

In another embodiment, the present invention is directed to methods for the treatment and/or prevention of a DDP-1 mediated disorder; wherein the DPP-1 mediated disorder is selected from the group consisting of rheumatoid arthritis, asthma, chronic obstructive pulmonary disease (COPD), sepsis, irritable bowel disease, cystic fibrosis, and abdominal aortic aneurism.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($R$moles−$S$moles)/($R$moles+$S$moles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee=([\alpha\text{-}obs]/[\alpha\text{-}max])\times 100$.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *"Design of Prodrugs"*, ed. H. Bundgaard, Elsevier, 1985.

Compounds of formula (I) wherein $R^3$ is selected from the group consisting of —$(CH_2)$—$R^4$ and —$CH_2$-phenyl-$Q^2$ and wherein $R^2$ is —$NR^4$-$Q^1$ may be prepared according to the process outlined in Scheme 1, below.

Scheme 1

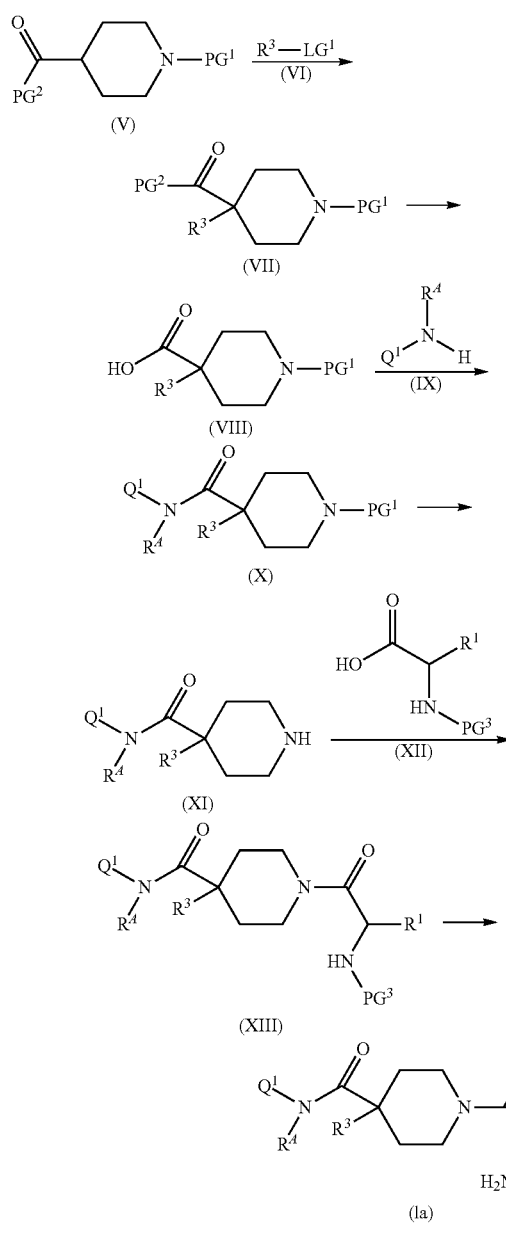

Accordingly, a suitably substituted compound of formula (V), wherein PG$^1$ is a suitably selected nitrogen protecting group such as Boc, CBz, and the like, and PG$^2$ is a suitably selected carboxylic acid protecting group such as methoxy, benzyloxy, and the like, a known compound or compound prepared by known methods, is reacted with a suitably substituted compound of formula (VI), wherein LG$^1$ is a suitably selected leaving group such as bromo, chloro, and the like, a known compound or compound prepared by known methods; in the presence of a suitably selected base such as LDA, LHMDS, and the like; in a suitably selected organic solvent such as THF, diethyl ether, 1,4-dioxane, and the like; to yield the corresponding compound of formula (VII).

The compound of formula (VII) is reacted to remove the oxygen protecting group PG$^2$, according to known methods, to yield the corresponding compound of formula (VIII). For example, wherein PG$^2$ is methoxy, the compound of formula (VII) may be de-protected by reacting with a suitably selected base such as NaOH, in a suitably selected solvent such as THF, and the like.

The compound of formula (VIII) is reacted with a suitably selected amine, a compound of formula (IX), a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (X).

The compound of formula (X) is reacted to remove the nitrogen protecting group PG$^1$, according to known methods, to yield the corresponding compound of formula (XI). For example, wherein PG$^1$ is Boc, the compound of formula (X) may be de-protected by reacting with a suitably selected acid such as HCl, in a suitably selected solvent such as 1,4-dioxane, and the like.

The compound of formula (XI) is reacted with a suitably substituted compound of formula (XII), wherein PG$^3$ is a suitably selected nitrogen protecting group such as Boc, CBz, and the like, a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XIII).

The compound of formula (XIII) is reacted to remove the nitrogen protecting group PG$^3$, according to known methods, to yield the corresponding compound of formula (Ia). For example, wherein PG$^3$ is Boc, the compound of formula (X) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

Compounds of formula (I) wherein R$^3$ is selected from the group consisting of —(CH$_2$)—R$^4$ and —CH$_2$-phenyl-Q$^2$ and wherein R$^2$ is —NR$^4$-Q$^1$ may alternatively be prepared according to the process outlined in Scheme 2, below.

Scheme 2

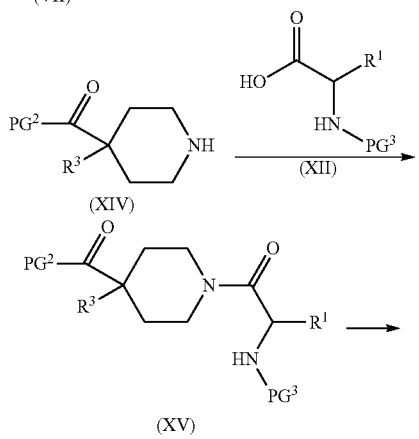

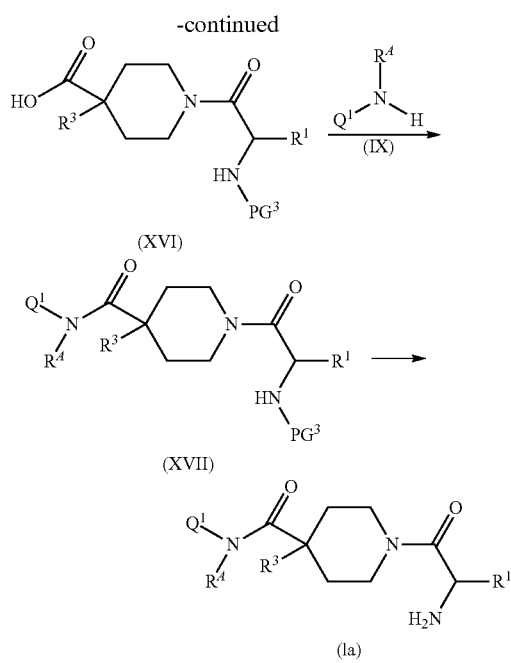

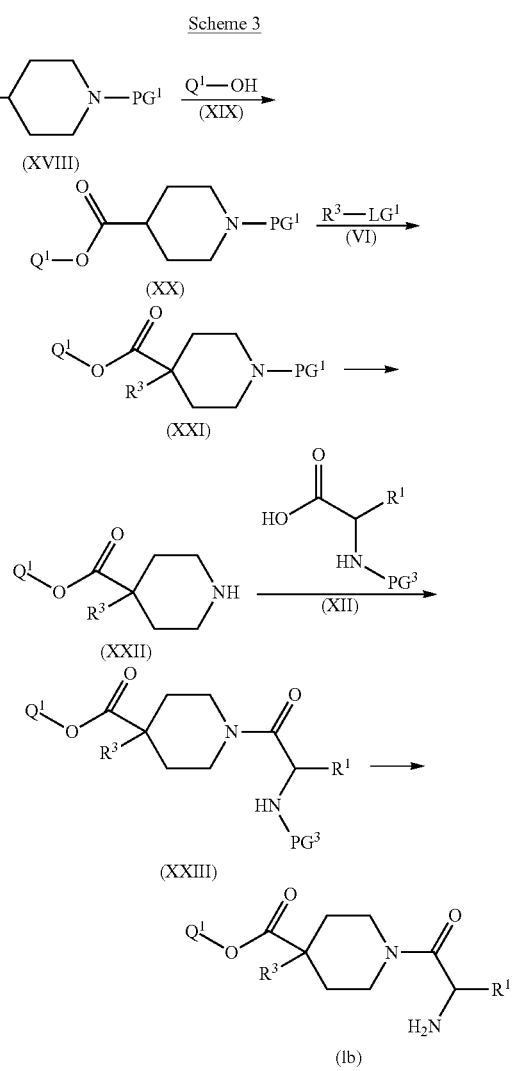

Accordingly, a suitably substituted compound of formula (VII), prepared for example as described in Scheme 1 above, is reacted to remove the nitrogen protecting group $PG^1$, according to known methods, to yield the corresponding compound of formula (XIV). For example, wherein $PG^1$ is Boc, the compound of formula (VII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

The compound of formula (XIV) is reacted with a suitably substituted compound of formula (XII), wherein $PG^3$ is a suitably selected nitrogen protecting group such as Boc, CBz, and the like, a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XV).

The compound of formula (XV) is reacted to remove the oxygen protecting group $PG^2$, according to known methods, to yield the corresponding compound of formula (XVI). For example, wherein $PG^2$ is methoxy, the compound of formula (XV) may be de-protected by reacting with a suitably selected base such as NaOH, in a suitably selected solvent such as THF, and the like.

The compound of formula (XVI) is reacted with a suitably substituted compound of formula (IX) a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XVII).

The compound of formula (XVII) is reacted to remove the nitrogen protecting group $PG^3$, according to known methods, to yield the corresponding compound of formula (Ia). For example, wherein $PG^3$ is Boc, the compound of formula (XVII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

Compounds of formula (I) wherein $R^3$ is selected from the group consisting of —($CH_2$)—$R^4$ and —$CH_2$-phenyl-$Q^2$ and wherein $R^2$ is —O-$Q^1$ may be prepared according to the process outlined in Scheme 3, below.

Scheme 3

Accordingly, a suitably substituted compound of formula (XVIII), wherein $PG^1$ is a suitably selected nitrogen protecting group such as Boc, CBz, and the like, a known compound or compound prepared by known methods, is reacted with a suitably substituted compound of formula (XIX), a known compound or compound prepared by known methods, in the presence of a suitably selected coupling agent such as DCC, BOP-Cl, and the like; in the presence of DMAP; in a suitably selected organic solvent such as DCM, diethyl ether, and the like; to yield the corresponding compound of formula (XX).

The compound of formula (XX) is reacted with a suitably substituted compound of formula (VI), wherein $LG^1$ is a suitably selected leaving group such as bromo, chloro, and the like, a known compound or compound prepared by known methods; in the presence of a suitably selected base such as LDA, LHMDS, and the like; in a suitably selected organic solvent such as THF, diethyl ether, 1,4-dioxane, and the like; to yield the corresponding compound of formula (XXI).

The compound of formula (XXI) is reacted to remove the nitrogen protecting group $PG^1$, according to known methods, to yield the corresponding compound of formula (XXII). For example, wherein $PG^1$ is Boc, the compound of formula (XXI) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

The compound of formula (XXII) is reacted with a suitably substituted compound of formula (XII), wherein $PG^3$ is a suitably selected nitrogen protecting group such as Boc, CBz, and the like, a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XXIII).

The compound of formula (XXIII) is reacted to remove the nitrogen protecting group $PG^3$, according to known methods, to yield the corresponding compound of formula (Ib). For example, wherein $PG^3$ is Boc, the compound of formula (XXIII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

Compounds of formula (I) wherein $R^3$ is an optionally substituted phenyl may be prepared according to the process outlined in Scheme 4, below.

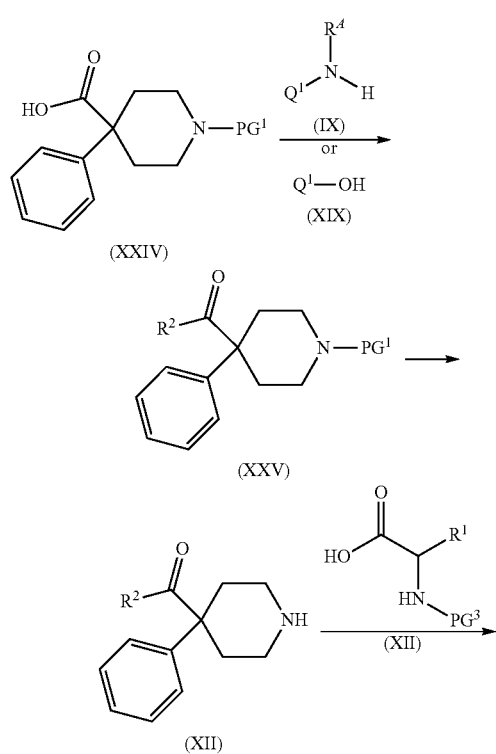

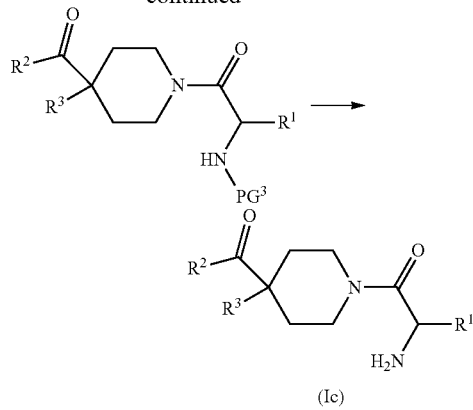

(Ic)

Accordingly, a suitably substituted compound of formula (XXIV), wherein $PG^1$ is a suitably selected nitrogen protecting group such as Boc, CBz, and the like, a known compound or compound prepared by known methods, is reacted with a suitably substituted compound of formula (IX) or a suitably substituted compound of formula (XIX), to yield the corresponding compound of formula (XXV).

More particularly, the compound of formula (XXIV) may be reacted with a suitably substituted compound of formula (IX), a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XXV) wherein $R^2$ is $-NR^4-Q^1$.

Alternatively, the compound of formula (XXIV) may be reacted with a suitably substituted compound of formula (XIX) a known compound or compound prepared by known methods, in the presence of a suitably selected coupling agent such as DCC, BOP-Cl, and the like; in the presence of DMAP; in a suitably selected organic solvent such as DCM, THF, and the like; to yield the corresponding compound of formula (XXV) wherein $R^2$ is $-O-Q^1$.

The compound of formula (XXV) is reacted to remove the nitrogen protecting group $PG^1$, according to known methods, to yield the corresponding compound of formula (XXVI). For example, wherein $PG^1$ is Boc, the compound of formula (XXI) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

The compound of formula (XXVI) is reacted with a suitably substituted compound of formula (XII), wherein $PG^3$ is a suitably selected nitrogen protecting group such as Boc, CBz, and the like, a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XXVII).

The compound of formula (XXVII) is reacted to remove the nitrogen protecting group $PG^3$, according to known methods, to yield the corresponding compound of formula (Ic). For example, wherein $PG^3$ is Boc, the compound of formula (XXVII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

Compounds of formula (I) wherein $R^3$ is an optionally substituted phenyl may alternatively be prepared according to the process outlined in Scheme 5, below.

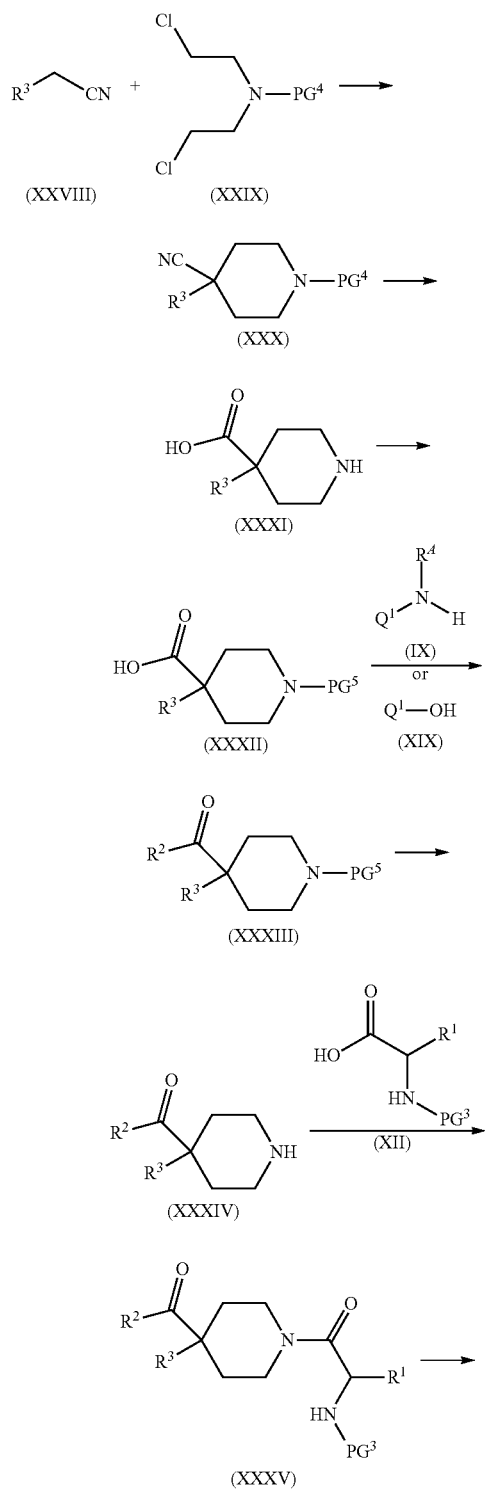

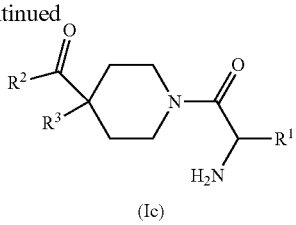

Accordingly, a suitably substituted compound of formula (XXVIII), a known compound or compound prepared by known methods, is reacted with a suitably substituted compound of formula (XXIX), wherein $PG^4$ is a suitably selected nitrogen protecting group such as Boc, CBz, and the like, a known compound or compound prepared by known methods; in the presence of a suitably selected reagent such as NaH, potassium t-butoxide, and the like; in a suitably selected organic solvent such as DMF, THF, and the like; to yield the corresponding compound of formula (XXX).

The compound of formula (XXX) is reacted with a suitably selected hydrolyzing agent such as aqueous HCl, and the like; neat or a suitably selected solvent such as 1,4-dioxane, and the like, preferably neat; to yield the corresponding compound of formula (XXXI). One skilled in the art will recognize that in the reaction of the compound of formula (XXX), under said hydrolysis conditions, the $PG^4$ protecting group will be removed.

The compound of formula (XXXI) is reacted to protect the piperidinyl nitrogen, according to known methods, to yield the corresponding compound of formula (XXXII), wherein $PG^5$ is a suitably selected protecting group such as Boc, CBz, and the like. For example, where $PG^5$ is BOC, the piperidinyl nitrogen on the compound of formula (XXXI) may be protected by reacting with Boc anhydride; in the presence of a suitably selected base such as aqueous NaOH, and the like.

The compound of formula (XXXII) is reacted with a suitably substituted compound of formula (IX) or a suitably substituted compound of formula (XIX), to yield the corresponding compound of formula (XXXIII).

More particularly, the compound of formula (XXXII) may be reacted with a suitably substituted compound of formula (IX), a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XXXIII) wherein $R^2$ is $-NR^4-Q^1$.

Alternatively, the compound of formula (XXXII) may be reacted with a suitably substituted compound of formula (XIX) a known compound or compound prepared by known methods, in the presence of a suitably selected coupling agent such as DCC, BOP-Cl, and the like; in the presence of DMAP; in a suitably selected organic solvent such as DCM, THF, and the like; to yield the corresponding compound of formula (XXXIII) wherein $R^2$ is $-O-Q^1$.

The compound of formula (XXXIII) is reacted to remove the nitrogen protecting group $PG^5$, according to known methods, to yield the corresponding compound of formula (XXXIV). For example, wherein $PG^1$ is Boc, the compound of formula (XXXIII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

The compound of formula (XXXIV) is reacted with a suitably substituted compound of formula (XII), wherein PG$^3$ is a suitably selected nitrogen protecting group such as Boc, CBz, and the like, a known compound or compound prepared by known methods; in the presence of a suitably selected coupling agent such as HBTU, HATU, and the like; in the presence of a suitably selected base such as TEA, DIPEA, pyridine, and the like; in a suitably selected organic solvent such as DMF, THF, and the like; to yield the corresponding compound of formula (XXXV).

The compound of formula (XXXV) is reacted to remove the nitrogen protecting group PG$^3$, according to known methods, to yield the corresponding compound of formula (Ic). For example, wherein PG$^3$ is Boc, the compound of formula (XXXV) may be de-protected by reacting with a suitably selected acid such as HCl, in a suitably selected solvent such as 1,4-dioxane, and the like.

One skilled in the art will recognize that compounds of formula (I) wherein R$^3$ is —CH$_2$-phenyl-Q$^2$, may alternatively be prepared as described in Scheme 6, below.

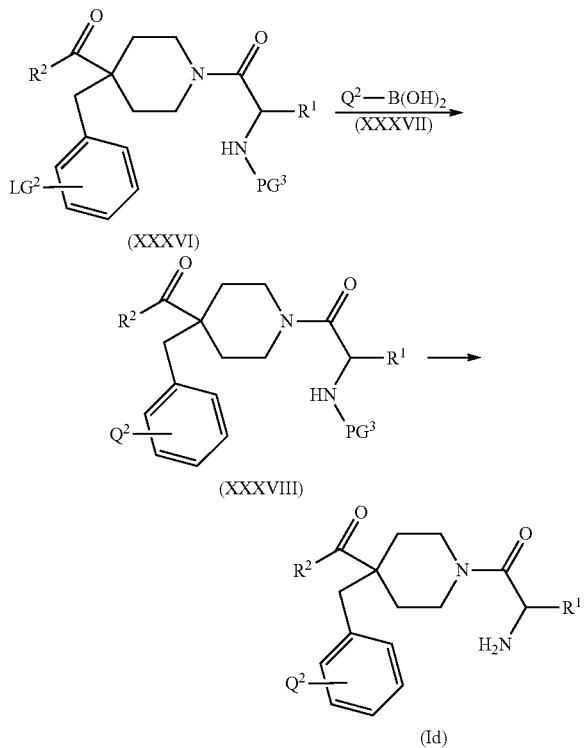

Scheme 6

Accordingly, a suitably substituted compound of formula (XXXVI), wherein LG$^2$ is a suitably selected leaving group such as iodo, bromo, and the like, and wherein PG$^3$ is a suitably selected nitrogen protecting group such as Boc, CBz, and the like, a compound prepared for example as herein described, is reacted with a suitably substituted boronic acid, a compound of formula (XXXVII), a known compound or compound prepared by known methods; in the presence of a suitably selected catalyst such as Pd(dppf)$_2$Cl$_2$, and the like; in the presence of a suitably selected inorganic base such as Na$_2$CO$_3$, Cs$_2$CO$_3$, and the like; in a suitably selected solvent such as 1,4-dioxane, water, and the like or in a mixture of said solvents; to yield the corresponding compound of formula (XXXVIII).

The compound of formula (XXXVIII) is reacted to remove the nitrogen protecting group PG$^3$, according to known methods, to yield the corresponding compound of formula (Id). For example, wherein PG$^3$ is Boc, the compound of formula (XXXVIII) may be de-protected for example, by reacting with a suitably selected acid such as HCl, in a suitably selected solvent such as 1,4-dioxane; or alternatively by reacting with a suitably selected acid such TFA in a suitably selected solvent such as methylene chloride.

One skilled in the art will recognize that wherein the compound of formula (I) is prepared with a terminal carboxy group on the R$^3$ substituent group, said carboxy group may be reacted with a suitably substituted amine (e.g. NHR$^F$R$^G$), in the presence of a suitably selected coupling agent such as HBTU, in the presence of a suitably selected base such as DIPEA, in a suitably selected organic solvent, such as DMF, to yield the corresponding compound, wherein the carboxy group (—C(O)OH) is converted to the corresponding amido group (—C(O)—NR$^F$R$^G$).

One skilled in the art will recognize that wherein the compound of formula (I) is prepared with a terminal nitro group on the R$^3$ substituent group, said nitro group may be reacted with hydrogen, in the presence of a suitably selected catalyst such as Pd/C, in a suitably selected solvent such as THF, ethanol, and the like, to yield the corresponding compound, wherein the nitro group (—NO$_2$) is converted to the corresponding amino group (—NH$_2$). Said amino group may be further reacted with for example, acetic anhydride, in the presence of a base such as DIPEA, in a solvent such as DCE, to yield the corresponding compound, wherein the amino group is converted to the corresponding methyl-carbonyl-amino group (—NH—C(O)—CH$_3$). Said amino group may alternatively be reacted with a suitably substituted sulfonyl chloride, in the presence of a base such as DIPEA, in a solvent such as DCE, to yield the corresponding compound, wherein the amino group is converted to the corresponding sulfonamide group (—NH—SO$_2$—CH$_3$).

One skilled in the art will recognize that wherein the compound of formula (I) is prepared with a terminal cyano group on the R$^3$ substituent group, said cyano group may be reacted with a suitably selected base such as NaOH, in a suitably selected solvent such as THF/methanol, to yield the corresponding compound of formula (I) wherein the cyano group (—CN) is converted to the corresponding amido group (—C(O)—NH$_2$). Alternatively, the cyano group may be reacted with a suitably selected acid such as HCl, to yield the corresponding compound of formula (I) wherein the cyano group (—CN) is converted to the corresponding carboxy group (—C(O)OH). Alternatively, the cyano group may be reacted with azidotrimethylsilane, in the presence of a suitably selected catalyst such as dibutylstannanone, in a suitably selected solvent such as DME, to convert the cyano group (—CN) to the corresponding 1,2,3,4-tetrazol-2-yl group.

Additional chemical transformation on terminal R$^3$ substituent groups such as those described above and in the examples which follow herein, may be performed on suitably substituted compounds of formula (I) or intermediates in the synthesis of compounds of formula (I), as would be readily recognized by one skilled in the art. One skilled in the art will further recognize that such transformations may be effected at any point in the synthesis of the compounds of formula (I), including but not limited to before or after attachment of the R$^2$ substituent group, and/or before or after attachment of the —C(O)—CH(NH$_2$)—R$^1$ substituent group.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1,000 mg or any amount or range therein, and may be given at a dosage of from about 0.01 mg/kg/day to about 100 mg/kg/day, or any amount or range therein, preferably from about 0.1 to about 50 mg/kg/day, or any amount or range therein, preferably from about 0.1 to about 25 mg/kg/day, or any amount or range therein, preferably from about 0.1 to about 15 mg/kg/day, or any amount or range therein, preferably from about 0.1 to about 10 mg/kg/day, or any amount or range therein, preferably from about 0.1 to about 5 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1,000 mg of the compound, or any amount or range therein; preferably about 1.0 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by DPP-1 is required.

The daily dosage of the products may be varied over a wide range from 0.1 to about 10,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1,000 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.1 mg/kg to about 50.0 mg/kg of body weight per day, or any amount or range therein. More preferably, from about 0.1 mg/kg to about 25.0 mg/kg of body weight per day, or any amount or range therein. More preferably, from about 0.1 mg/kg to about 15.0 mg/kg of body weight per day, or any amount or range therein. More preferably, from about 0.1 mg/kg to about 10.0 mg/kg of body weight per day, or any amount or range therein. More preferably, from about 0.1 mg/kg to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. For example, Methot, N., et al., "In Vivo Inhibition of Serine Protease Processing Requires a High Fractional Inhibition of Cathepsin C", *Molecular Pharmacology*, (2008), Vol. 73, No. 6, pp 1857-1865 disclose an in vivo assay in rats for measuring inhibition of Cathepsin C (DPP-1).

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #3

(S)-1-(2-amino-3-(thiophen-2-yl)propanoyl)-4-(biphenyl-4-ylmethyl)-N-(cyclohexylmethyl)piperidine-4-carboxamide hydrochloride

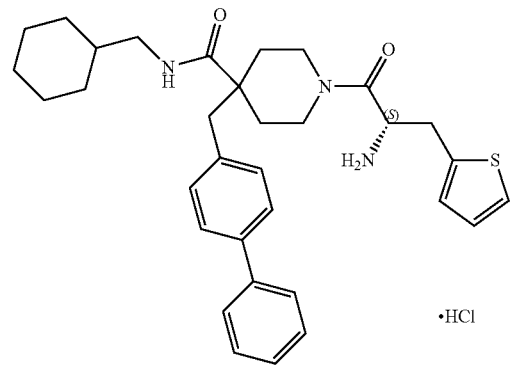

Step A:
4-Biphenyl-4-ylmethyl-piperidine-1,4-dicarboxylic acid 1-tert-butyl ester 4-methyl ester To a solution of piperidine-1,4-dicarboxylic acid 1-tert-butyl ester 4-methyl ester (13.19 mmol; 3.21 g) in dry THF (100 mL) under argon at −78° C. was added, dropwise, a 2M solution of lithium diisopropylamide (2M solution in heptanes/THF/ethylbenzene; 15.83 mmol; 7.92 mL). The resulting solution was stirred at −78° C. for 2 hours. 4-Biphenylmethyl bromide (15.83 mmol; 3.91 g) was added and the resulting solution was stirred at −78° C. for 2 hours, then allowed to warm to room temperature overnight. Ethyl acetate (150 ml) was added. The resulting solution was washed with a 1M aqueous hydrochloric acid solution (2×50 mL) and brine (50 mL) and dried over magnesium sulfate. After filtration and evaporation, the residue was purified via flash column chromatography (eluent gradient: 0 to 50% EtOAc in heptane) to yield 4-biphenyl-4-ylmethyl-piperidine-1,4-dicarboxylic acid 1-tert-butyl ester 4-methyl ester. MS (ESI) m/z 432.3 [M+Na]$^+$.

Step B:
4-Biphenyl-4-ylmethyl-piperidine-1,4-dicarboxylic acid mono-tert-butyl ester To a solution of 4-biphenyl-4-ylmethyl-piperidine-1,4-dicarboxylic acid 1-tert-butyl ester 4-methyl ester (11.4 mmol; 4.65 g) in THF (30 mL) and methanol (20 mL) was added a 1M solution of sodium hydroxide (28.4 mmol; 28.4 mL) and the resulting mixture was heated to reflux for 48 hours. The resulting mixture was then evaporated and a 1N hydrochloric acid solution (200 mL) was added to the residue. A white precipitate formed that was separated via filtration to yield 4-biphenyl-4-ylmethyl-piperidine-1,4-dicarboxylic acid mono-tert-butyl ester. MS (ESI) m/z 395.76 [M+H]$^+$.

Step C:
4-Biphenyl-4-ylmethyl-piperidine-4-carboxylic acid cyclohexylmethylamide hydrochloride To a solution of 4-biphenyl-4-ylmethyl-piperidine-1,4-dicarboxylic acid mono-tert-butyl ester (6.32 mmol; 2.5 g) in DMF (50 mL) was added cyclohexylmethylamine (7.59 mmol; 0.99 mL), N,N-diisopropyl-N-ethylamine (15.8 mmol; 2.80 mL) and HBTU (7.59 mmol; 2.88 g), and the resulting mixture was stirred at room temperature overnight. Ethyl acetate (200 mL) was added, and the resulting solution was washed with a 1N hydrochloric acid solution (2×25 mL), and brine (25 mL), and dried over magnesium sulfate. After filtration and evaporation, the residue was purified via flash column chromatography (eluent gradient: 0 to 50% EtOAc in heptane) to yield 4-biphenyl-4-ylmethyl-4-(cyclohexylmethyl-carbamoyl)-piperidine-1-carboxylic acid tert-butyl ester after evaporation. The material thus obtained was dissolved in THF (8 mL) and a 4N HCl solution in 1,4-dioxane (15 mL) was added. The resulting mixture was stirred overnight at room temperature and evaporated. The residue was triturated with diethyl ether and dried to yield 4-biphenyl-4-ylmethyl-piperidine-4-carboxylic acid cyclohexylmethylamide as a hydrochloride salt. MS (ESI) m/z 391.09 [M+H]$^+$.

Step D: 1-[2-(S)-Amino-3-thiophen-2-yl-propionyl]-4-biphenyl-4-ylmethyl-piperidine-4-carboxylic acid cyclohexylmethylamide hydrochloride To a solution of 4-biphenyl-4-ylmethyl-piperidine-4-carboxylic acid cyclohexylmethylamide (3.98 mmol; 1.7 g) in DMF (20 mL) was added (S)-2-tert-butoxycarbonylamino-3-thiophen-2-yl-propionic acid (4.63 mmol; 1.26 g), N,N-diisopropyl-N-ethylamine (13.9 mmol; 2.46 mL) and HBTU (6.02 mmol; 2.28 g), and the resulting mixture was stirred at room temperature overnight. The resulting mixture was then purified via reverse phase HPLC and the desired fractions were combined and lyophilized. The residue was dissolved in THF (5 mL) and a 4N HCl solution in 1,4-dioxane (15 mL) was added. The resulting solution was stirred for 7 hours at room temperature and evaporated. The residue was triturated with diethyl ether and dried under vacuum to yield 1-[2-(S)-amino-3-thiophen-2-yl-propionyl]-4-biphenyl-4-ylmethyl-piperidine-4-carboxylic acid cyclohexylmethylamide as a hydrochloride salt.
$^1$H-NMR (CD$_3$OD): δ 7.33-7.72 (7H, m), 7.31 (1H, dd), 7.11-7.29 (2H, m), 7.11 (1H, d), 6.96 (1H, d), 4.65-4.68 (1H, m), 4.24-4.32 (1H, m), 3.57-3.74 (2H, m), 3.20-3.40 (4H, m), 2.65-3.10 (4H, m), 0.6-2.20 (15H, m). MS (ESI) m/z 544.04 [M+H]$^+$.

Example 2

Compound #6

(S)-1-(2-amino-3-(thiophen-2-yl)propanoyl)-4-(biphenyl-4-ylmethyl)-N-((tetrahydro-2H-pyran-4-yl)methyl)piperidine-4-carboxamide hydrochloride

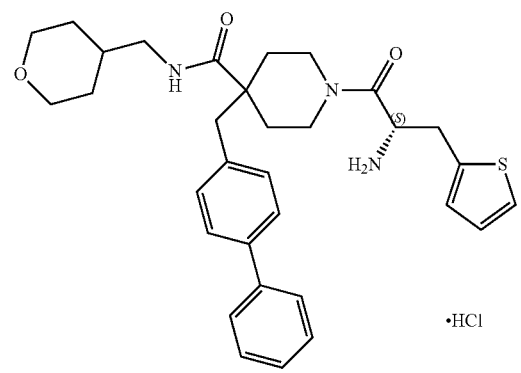

Step A:
4-Biphenyl-4-ylmethyl-piperidine-4-carboxylic acid methyl ester

To a solution of piperidine-1,4-dicarboxylic acid 1-tert-butyl ester 4-methyl ester (7.32 mmol; 3 g) in dichloromethane (10 mL) at 0° C. was added trifluoroacetic acid (10 mL) and the resulting mixture was stirred for 3 hours at 0° C. The resulting mixture was then evaporated. The resulting residue was dissolved in ethyl acetate (50 mL) and washed with a saturated sodium bicarbonate solution (25 mL) and brine (25 mL). The organic phase was dried over magnesium sulfate, filtered, and evaporated to yield 4-biphenyl-4-ylmethyl-piperidine-4-carboxylic acid methyl ester. MS (ESI) m/z 310.28 [M+H]$^+$.

Step B: 4-Biphenyl-4-ylmethyl-1-[2-(S)-tert-butoxycarbonylamino-3-thiophen-2-yl-propionyl]-piperidine-4-carboxylic acid methyl ester To a solution of 4-biphenyl-4-ylmethyl-piperidine-4-carboxylic acid methyl ester (8.73 mmol; 2.7 g) in DMF (20 mL)

was added (S)-2-tert-butoxycarbonylamino-3-thiophen-2-yl-propionic acid (9.58 mmol; 2.60 g), N,N-diisopropyl-N-ethyl-amine (17.46 mmol; 3.1 mL) and HBTU (10.48 mmol; 3.97 g), and the resulting mixture was stirred at room temperature overnight. Ethyl acetate (200 mL) was added and the resulting solution was washed with a 1N hydrochloric acid solution (2×50 mL) and brine (50 mL), and dried over magnesium sulfate. After filtration and evaporation, the residue was purified via flash column chromatography (eluent gradient: 0 to 60% EtOAc in heptane) to yield 4-biphenyl-4-ylmethyl-1-[2-(S)-tert-butoxycarbonylamino-3-thiophen-2-yl-propionyl]-piperidine-4-carboxylic acid methyl ester after evaporation. MS (ESI) m/z 565.36 [M+H]+.

Step C: 4-Biphenyl-4-ylmethyl-1-[2-(S)-tert-butoxycarbonylamino-3-thiophen-2-yl-propionyl]-piperidine-4-carboxylic acid To a solution of 4-biphenyl-4-ylmethyl-1-[2-(S)-tert-butoxycarbonylamino-3-thiophen-2-yl-propionyl]-piperidine-4-carboxylic acid methyl ester (5.63 mmol; 3.17 g) in THF (30 mL) and methanol (20 mL) was added a 1M solution of sodium hydroxide (16.9 mmol; 16.9 mL) and the resulting mixture was heated to reflux for 48 hours. The resulting mixture was then evaporated and a 1N hydrochloric acid solution (200 mL) was added to the residue. A white precipitate formed that was separated via filtration to yield 4-biphenyl-4-ylmethyl-1-[2-(S)-tert-butoxycarbonylamino-3-thiophen-2-yl-propionyl]-piperidine-4-carboxylic acid. MS (ESI) m/z 547.44 [M+H]+.

Step D: 1-[2-(S)-Amino-3-thiophen-2-yl-propionyl]-4-biphenyl-4-ylmethyl-piperidine-4-carboxylic acid (tetrahydro-pyran-4-ylmethyl)-amide hydrochloride To a solution of 4-biphenyl-4-ylmethyl-1-[2-(S)-tert-butoxycarbonylamino-3-thiophen-2-yl-propionyl]-piperidine-4-carboxylic acid (0.24 mmol; 0.13 g) in DMF (5 mL) was added C-(tetrahydro-pyran-4-yl)-methylamine (0.28 mmol; 0.027 g), N,N-diisopropyl-N-ethylamine (0.48 mmol; 0.084 mL) and HBTU (0.28 mmol; 0.108 g), and the resulting mixture was stirred at room temperature overnight. The resulting mixture was then purified via reverse phase HPLC and the desired fractions were combined and lyophilized. The resulting residue was dissolved in THF (5 mL) and a 4N HCl solution in 1,4-dioxane (15 mL) was added. The resulting solution was stirred for 7 hours at room temperature and evaporated. The residue was triturated with diethyl ether and dried under vacuum to yield 1-[2-(S)-amino-3-thiophen-2-yl-propionyl]-4-biphenyl-4-ylmethyl-piperidine-4-carboxylic acid(tetrahydro-pyran-4-ylmethyl)-amide as a hydrochloride salt.

$^1$H-NMR (CD$_3$OD): δ 7.33-7.72 (7H, m), 7.31 (1H, dd), 7.11-7.29 (2H, m), 7.11 (1H, d), 6.96 (1H, d), 4.65-4.68 (1H, m), 4.24-4.32 (1H, m), 3.80-4.00 (4H, m), 3.50-3.70 (2H, m), 3.20-3.50 (4H, m), 2.65-3.20 (4H, m), 0.70-2.30 (9H, m). MS (ESI) m/z 546.04 [M+H]+.

Example 3

Compound #15

(S)-cyclohexylmethyl 1-(2-amino-3-(thiophen-2-yl)propanoyl)-4-(4-cyanobenzyl)piperidine-4-carboxylate hydrochloride

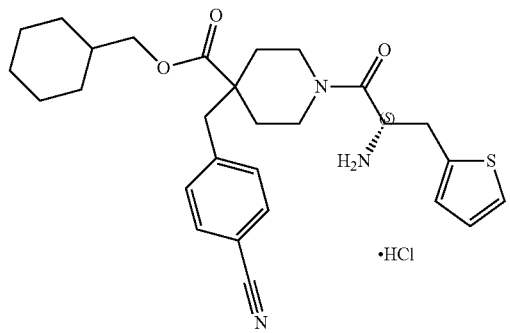

Step A: Piperidine-1,4-dicarboxylic acid 1-tert-butyl ester 4-cyclohexylmethyl ester To a solution of piperidine-1,4-dicarboxylic acid mono-tert-butyl ester (66.94 mmol; 15.35 g) in dichloromethane (100 mL) was added cyclohexylmethanol (55.79 mmol; 6.37 g), dimethylaminopyridine (1.12 mmol; 0.14 g) and dicyclohexylcarbodiimide (66.94 mmol; 12.83 g) and the resulting mixture was stirred for 3 hours at room temperature. The resulting solution was evaporated and the residue was dissolved in ethyl acetate (200 mL). The resulting solution was washed with a 1N hydrochloric acid solution (2×50 mL) and brine (50 mL), and dried over magnesium sulfate. After filtration and evaporation, the residue was purified via flash column chromatography ((eluent gradient: 0 to 5% EtOAc in heptane) to yield piperidine-1,4-dicarboxylic acid 1-tert-butyl ester 4-cyclohexylmethyl ester after evaporation. MS (ESI) m/z 326.29 [M+H]+.

Step B: 4-(4-Cyano-benzyl)-piperidine-1,4-dicarboxylic acid 1-tert-butyl ester 4-cyclohexylmethyl ester To a solution of piperidine-1,4-dicarboxylic acid 1-tert-butyl ester 4-cyclohexylmethyl ester (6.61 mmol; 2.15 g) in dry THF (30 mL) under argon at −78° C. was added, dropwise, a 2M solution of lithium diisopropylamide (2M solution in heptanes/THF/ethylbenzene; 8.59 mmol; 4.29 mL). The resulting solution was stirred at −78° C. for 2 hours. 4-Bromomethyl-benzonitrile (6.61 mmol; 1.30 g) was added and the resulting solution was stirred at −78° C. for 2 hours, then allowed to warm to room temperature overnight. Ethyl acetate (150 ml) was added. The resulting solution was washed with a 1M aqueous hydrochloric acid solution (2×50 mL) and brine (50 mL) and dried over magnesium sulfate. After filtration and evaporation, the residue was purified via flash column chromatography (eluent gradient: 0 to 50% EtOAc in heptane) to yield 4-(4-cyano-benzyl)-piperidine-1,4-dicarboxylic acid 1-tert-butyl ester 4-cyclohexylmethyl ester. MS (ESI) m/z 436.38 [M+Na]+.

Step C: 4-(4-Cyano-benzyl)-piperidine-4-carboxylic acid cyclohexylmethyl ester

To a solution of 4-(4-cyano-benzyl)-piperidine-1,4-dicarboxylic acid 1-tert-butyl ester 4-cyclohexylmethyl ester (3.90 mmol; 1.72 g) in dichloromethane (12 mL) at 0° C. was added trifluoroacetic acid (12 mL) and the resulting mixture was stirred for 2 hours at room temperature. The resulting mixture was evaporated. The resulting residue was dissolved in ethyl acetate (50 mL) and washed with a saturated sodium bicarbonate solution (25 mL) and brine (25 mL). The organic phase was dried over magnesium sulfate, filtered, and evaporated to yield 4-(4-cyano-benzyl)-piperidine-4-carboxylic acid cyclohexylmethyl ester. $^1$H-NMR (CDCl$_3$): 7.55 (1H, d), 7.20 (1H, d), 3.90 (2H, dd), 3.35 (2H, m), 2.70-3.10 (3H, m), 2.60 (1H, m), 2.25 (1H, m), 0.70-2.20 (15H, m).

Step D: 1-[2-(S)-Amino-3-thiophen-2-yl-propionyl]-4-(4-cyano-benzyl)-piperidine-4-carboxylic acid cyclohexylmethyl ester hydrochloride To a solution of 4-(4-cyano-benzyl)-piperidine-4-carboxylic acid cyclohexylmethyl ester (0.377 mmol; 0.128 g) in DMF (2 mL) was added (S)-2-tert-butoxycarbonylamino-3-thiophen-2-yl-propionic acid (0.377 mmol; 0.102 g), N,N-diisopropyl-N-ethylamine (0.755 mmol; 0.134 mL) and HBTU (0.491 mmol; 0.186 g), and the resulting mixture was stirred at room temperature overnight. The resulting mixture was purified via reverse phase HPLC and the desired fractions were combined and lyophilized. The residue was dissolved in a 4 M HCl solution in 1,4-dioxane (3 mL) and the resulting solution was stirred overnight at room temperature. The solution was then evaporated, and the residue was triturated with diethyl ether and dried under vacuum to yield 1-[2-(S)-amino-3-thiophen-2-yl-propionyl]-4-(4-cyano-benzyl)-piperidine-4-carboxylic acid cyclohexylmethyl ester as a hydrochloride salt.
$^1$H-NMR (CD$_3$OD): δ 7.64 (2H, d), 7.46 (1H, d), 7.33 (1H, d), 7.23 (2H, d), 7.10 (1H, dd), 4.69 (1H, m), 4.36 (1H, m), 3.83 (2H, d), 3.60-3.80 (1H, m), 3.30-3.50 (4H, m), 2.55-3.10 (4H, m), 0.55-2.0 (15H, m). MS (ESI) m/z 494.27 [M+H]$^+$.

Example 4

Compound #47

(S)-1-(2-amino-3-(thiophen-2-yl)propanoyl)-N-cyclohexyl-4-((3'-methoxybiphenyl-4-yl)methyl)piperidine-4-carboxamide hydrochloride

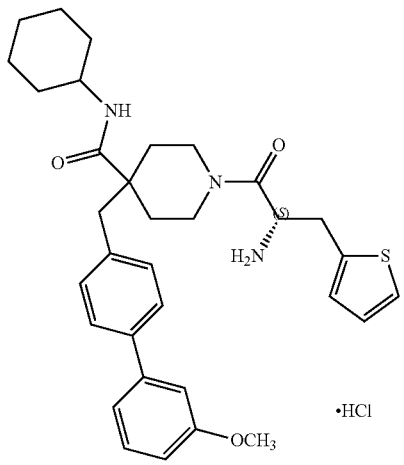

Step A: 1-(2-(S)-Amino-3-thiophen-2-yl-propionyl)-4-(3'-methoxy-biphenyl-4-ylmethyl)-piperidine-4-carboxylic acid cyclohexylamide hydrochloride To a solution of (S)-{2-[4-cyclohexylcarbamoyl-4-(4-iodo-benzyl)-piperidin-1-yl]-2-oxo-1-thiophen-2-ylmethyl-ethyl}-carbamic acid tert-butyl ester 1d (0.221 mmol; 0.15 g) (prepared as described in Example 1 above, substituting 4-iodobenzylbromide for 4-biphenylmethyl bromide and cyclohexylamine for cyclohexylmethylamine) and 3-methoxyphenylboronic acid (0.265 mmol; 0.04 g) in dioxane (2 mL) was added a 10% solution of sodium carbonate in water (0.53 mL), followed by 1,1'-bis-(di-t-butylphosphino)-ferrocene palladium dichloride (0.011 mmol; 7.2 mg). The resulting mixture was heated in sealed tube at 100° C. for 3 hrs. The resulting mixture was allowed to cool to room temperature and then purified via reverse phase HPLC. The desired fractions were collected and lyophilized. The resulting residue was dissolved in a 4 M HCl solution in 1,4-dioxane (3 mL) and the resulting solution was stirred overnight at room temperature. The resulting solution was then evaporated, and the residue was triturated with diethyl ether and dried under vacuum to yield 1-(2-(S)-amino-3-thiophen-2-yl-propionyl)-4-(3'-methoxy-biphenyl-4-ylmethyl)-piperidine-4-carboxylic acid cyclohexylamide as a hydrochloride salt.
$^1$H-NMR (CD$_3$OD): δ 6.82-7.50 (11H, m), 4.65 (1H, m), 4.27 (1H, m), 3.83 (3H, s), 3.60-3.80 (2H, m), 3.20-3.40 (4H, m), 2.65-2.85 (2H, m), 0.6-2.2 (14H, m). MS (ESI) m/z 560.17 [M+H]$^+$.

Example 5

Compound #59

(S)-1-(2-amino-3-(thiophen-2-yl)propanoyl)-N-cyclohexyl-4-(4-(dimethylcarbamoyl)benzyl)piperidine-4-carboxamide hydrochloride

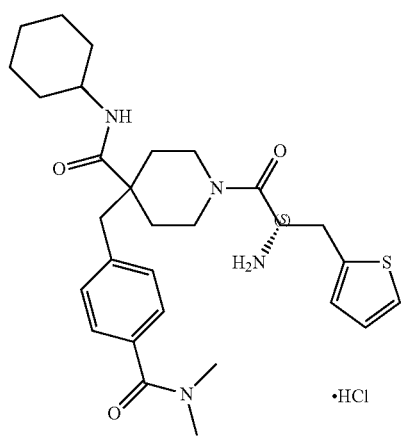

Step A: Piperidine-1,4-dicarboxylic acid 4-benzyl ester 1-tert-butyl ester

To a solution of piperidine-1,4-dicarboxylic acid mono-tert-butyl ester (35.94 mmol; 8.24 g) in dichloromethane (100 mL) was added benzyl alcohol (55.79 mmol; 4.73 mL), dimethylaminopyridine (0.72 mmol; 0.08 g) and dicyclohexylcarbodiimide (43.13 mmol; 8.27 g) and the resulting mixture was stirred for 3 hours at room temperature. The resulting solution was evaporated and the residue was dissolved in ethyl acetate (300 mL). The resulting solution was washed with a 1N hydrochloric acid solution (2×50 mL) and brine (50 mL), and dried over magnesium sulfate. After filtration and evaporation, the residue was purified via flash column chromatography ((eluent gradient: 0 to 50% EtOAc in heptane) to yield piperidine-1,4-dicarboxylic acid 4-benzyl ester 1-tert-butyl ester after evaporation. MS (ESI) m/z 320.19 [M+H]$^+$.

Step B: 4-(4-Methoxycarbonyl-benzyl)-piperidine-1, 4-dicarboxylic acid 4-benzyl ester 1-tert-butyl ester To a solution of piperidine-1,4-dicarboxylic acid 4-benzyl ester 1-tert-butyl ester (30.12 mmol; 9.62 g) in dry THF (100 mL) under argon at −78° C. was added, dropwise, a 2M solution of lithium diisopropylamide (2M solution in heptanes/THF/ethylbenzene; 39.16 mmol; 19.58 mL). The resulting solution was stirred at −78° C. for 2 hours. 4-Bromomethylbenzoic acid methyl ester (30.12 mmol; 6.90 g) was added and the resulting solution was stirred at −78° C. for 2 hours and allowed to warm to room temperature overnight. Ethyl acetate (150 ml) was added. The resulting solution was washed with a 1M aqueous hydrochloric acid solution (2×50 mL) and brine (50 mL) and dried over magnesium sulfate. After filtration and evaporation, the residue was purified via flash column chromatography (eluent gradient: 0 to 50% EtOAc in heptane) to yield 4-(4-methoxycarbonyl-benzyl)-piperidine-1,4-dicarboxylic acid 4-benzyl ester 1-tert-butyl ester. MS (ESI) m/z 468.20 [M+H]$^+$.

Step C: 4-(4-Methoxycarbonyl-benzyl)-piperidine-1, 4-dicarboxylic acid mono-tert-butyl ester To a solution of 4-(4-methoxycarbonyl-benzyl)-piperidine-1,4-dicarboxylic acid 4-benzyl ester 1-tert-butyl ester (10.65 mmol; 4.98 g) in tetrahydrofuran (20 mL) and ethanol (40 mL) was added 10% palladium on carbon (3 g), and the resulting mixture was hydrogenated under 50 psi of hydrogen pressure for 5 hours at room temperature. The catalyst was removed via filtration, and the filtrate was evaporated to yield 4-(4-methoxycarbonyl-benzyl)-piperidine-1,4-dicarboxylic acid mono-tert-butyl ester. $^1$H-NMR (CDCl$_3$): 7.95 (2H, d), 7.19 (2H, d), 3.90 (3H, s), 2.92 (4H, m), 2.05 (2H, s), 1.40-1.70 (4H, m), 1.45 (9H, s).

Step D: 4-(4-Cyclohexylcarbamoyl-piperidin-4-ylmethyl)-benzoic acid methyl ester To a solution of solution of 4-(4-methoxycarbonyl-benzyl)-piperidine-1,4-dicarboxylic acid 4-benzyl ester 1-tert-butyl ester (9.35 mmol; 3.53 g) in DMF (40 mL) was added cyclohexylamine (11.22 mmol; 1.28 mL), N, N-diisopropyl-N-ethylamine (23.38 mmol; 4.14 mL) and HBTU (11.22 mmol; 4.26 g), and the resulting mixture was stirred at room temperature overnight. Ethyl acetate (200 mL) was added, and the resulting solution was washed with a 1N hydrochloric acid solution (2×25 mL), and brine (25 mL), and dried over magnesium sulfate. After filtration and evaporation, the residue was purified via flash column chromatography (eluent gradient: 0 to 70% EtOAc in heptane) to yield 4-cyclohexylcarbamoyl-4-(4-methoxycarbonyl-benzyl)-piperidine-1-carboxylic acid tert-butyl ester after evaporation. The material thus obtained was dissolved in dichloromethane (25 mL) and trifluoroacetic acid (25 mL) was added. The resulting mixture was stirred for 2 hours at room temperature and evaporated. The residue was dissolved in dichloromethane (300 mL) and washed with a saturated sodium bicarbonate solution (50 mL) and brine (50 mL). The organic phase was dried over magnesium sulfate, filtered, and evaporated to yield 4-(4-cyclohexylcarbamoyl-piperidin-4-ylmethyl)-benzoic acid methyl ester. MS (ESI) m/z 459.30 [M+H]$^+$.

Step E: 4-[1-(2-(S)-tert-Butoxycarbonylamino-3-thiophen-2-yl-propionyl)-4-cyclohexylcarbamoyl-piperidin-4-ylmethyl]-benzoic acid methyl ester To a solution of 4-(4-cyclohexylcarbamoyl-piperidin-4-ylmethyl)-benzoic acid methyl ester (3.32 mmol; 1.19 g) in DMF (50 mL) was added (S)-2-tert-butoxycarbonylamino-3-thiophen-2-yl-propionic acid (3.32 mmol; 0.90 g), N,N-diisopropyl-N-ethylamine (6.64 mmol; 1.18 mL) and HBTU (4.32 mmol; 1.64 g), and the resulting mixture was stirred at room temperature overnight. Ethyl acetate (150 mL) was added, and the resulting solution was washed with a 1H hydrochloric acid solution (2×50 mL), and brine (50 mL). The organic phase was dried over magnesium sulfate, filtered, and evaporated. The residue was purified via flash column chromatography (eluent gradient: 0 to 10% methanol in dichloromethane) and the desired fractions were combined and evaporated to yield 4-[1-(2-(S)-tert-butoxycarbonylamino-3-thiophen-2-yl-propionyl)-4-cyclohexylcarbamoyl-piperidin-4-ylmethyl]-benzoic acid methyl ester. MS (ESI) m/z 612.13 [M+H]$^+$.

Step F: 4-[1-(2-(S)-tert-Butoxycarbonylamino-3-thiophen-2-yl-propionyl)-4-cyclohexylcarbamoyl-piperidin-4-ylmethyl]-benzoic acid To a solution of 4-[1-(2-tert-butoxycarbonylamino-3-thiophen-2-yl-propionyl)-4-cyclohexylcarbamoyl-piperidin-4-ylmethyl]-benzoic acid methyl ester (4.46 mmol; 2.73 g) in THF (30 mL) and methanol (10 mL) was added a 1M solution of sodium hydroxide (6.69 mmol; 6.69 mL) and the resulting mixture was stirred overnight at room temperature. The resulting mixture was then evaporated and water (20 mL) was added. A 1N hydrochloric acid solution (10 mL) was added dropwise. A precipitate formed that was separated via filtration to yield 4-[1-(2-(S)-tert-butoxycarbonylamino-3-thiophen-2-yl-propionyl)-4-cyclohexylcarbamoyl-piperidin-4-ylmethyl]-benzoic acid after drying. MS (ESI) m/z 598.23 [M+H]$^+$.

Step G: 1-(2-(S)-Amino-3-thiophen-2-yl-propionyl)-4-(4-dimethylcarbamoyl-benzyl)-piperidine-4-carboxylic acid cyclohexylamide hydrochloride To a solution of 4-[1-(2-tert-butoxycarbonylamino-3-thiophen-2-yl-propionyl)-4-cyclohexylcarbamoyl-piperidin-4-ylmethyl]-benzoic acid (0.201 mmol; 0.12 g) in DMF (1.5 mL) was added N,N-dimethylamine hydrochloride (0.241 mmol; 0.02 g), N,N-diisopropyl-N-ethylamine (0.502 mmol; 0.089 mL) and HBTU (0.241 mmol; 0.091 g), and the resulting mixture was stirred at room temperature overnight. The mixture was then purified via reverse phase HPLC and the desired fractions were combined and lyophilized. The resulting residue was dissolved in a 4N HCl solution in 1,4-dioxane (3 mL) and the resulting solution was stirred for 5 hours at room temperature and evaporated. The residue was triturated with diethyl ether and dried under vacuum to yield 1-(2-(S)-amino-3-thiophen-2-yl-propionyl)-4-(4-dimethylcarbamoyl-benzyl)-piperidine-4-carboxylic acid cyclohexylamide as a hydrochloride salt.

¹H-NMR (CD₃OD): δ 7.43 (1H, d), 7.35 (2H, dd), 7.16 (2H, dd), 7.05 (1H, dd), 6.96 (1H, d), 4.58 (1H, m), 4.31 (1H, m), 3.65 (2H, s), 3.31 (4H, m), 3.10 (3H, s), 2.99 (3H, s), 2.70-2.87 (2H, m), 1.10-2.20 (14H, m). MS (ESI) m/z 525.30 [M+H]⁺.

Example 6

Compound #90

(S)-4-(4-acetamidobenzyl)-1-(2-amino-3-(thiophen-2-yl)propanoyl)-N-cyclohexylpiperidine-4-carboxamide hydrochloride

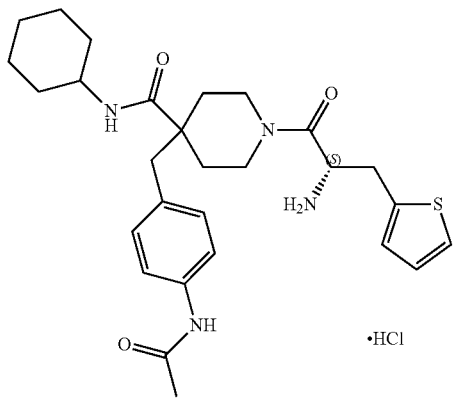

Step A: (S)-{2-[4-(4-Aminobenzyl)-4-cyclohexylcarbamoyl-piperidin-1-yl]-2-oxo-1-thiophen-2-ylmethyl-ethyl}-carbamic acid tert-butyl ester To a solution of {2-[4-Cyclohexylcarbamoyl-4-(4-nitrobenzyl)-piperidin-1-yl]-2-oxo-1-thiophen-2-ylmethyl-ethyl}-carbamic acid tert-butyl ester (9.77 mmol; 5.85 g) (prepared as in Example 1, substituting 4-nitrobenzylbromide for 4-biphenylmethyl bromide and cyclohexylamine for cyclohexylmethylamine), in tetrahydrofuran (20 mL) and ethanol (40 mL) was added 10% palladium on carbon (2 g), and the resulting mixture was hydrogenated under 50 psi of hydrogen pressure overnight at room temperature. The catalyst was removed via filtration, and the filtrate was evaporated to yield (S)-{2-[4-(4-aminobenzyl)-4-cyclohexylcarbamoyl-piperidin-1-yl]-2-oxo-1-thiophen-2-ylmethyl-ethyl}-carbamic acid tert-butyl ester. MS (ESI) m/z 569.40 [M+H]⁺.

Step B: 4-(4-Acetylaminobenzyl)-1-(2-(S)-amino-3-thiophen-2-yl-propionyl)-piperidine-4-carboxylic acid cyclohexylamide hydrochloride To a solution of {2-[4-(4-aminobenzyl)-4-cyclohexylcarbamoyl-piperidin-1-yl]-2-oxo-1-thiophen-2-ylmethyl-ethyl}-carbamic acid tert-butyl ester (0.352 mmol; 0.2 g) in 1,2-dichloroethane (5 mL) was added acetic anhydride (0.422 mmol; 0.043 g) and N,N-diisopropyl-N-ethylamine (0.703 mmol; 0.123 mL) and the resulting solution was stirred for 3 hours at room temperature. The resulting mixture was then evaporated and the residue was purified via reverse phase HPLC. The desired fractions were combined and lyophilized. The resulting residue was dissolved in tetrahydrofuran (10 mL) and a 4N HCl in 1,4-dioxane solution (15 mL), and the mixture was then stirred for 6 hours at room temperature and evaporated. The residue was triturated with diethyl ether and dried under vacuum to yield 4-(4-acetylaminobenzyl)-1-(2-(S)-amino-3-thiophen-2-yl-propionyl)-piperidine-4-carboxylic acid cyclohexylamide as a hydrochloride salt.

¹H-NMR (CD₃OD): δ 7.43 (1H, d), 7.35 (2H, dd), 7.16 (2H, dd), 7.05 (1H, dd), 6.96 (1H, d), 4.70 (1H, m), 4.31 (1H, m), 3.5-3.7 (2H, m), 3.30 (4H, m), 2.65-2.78 (2H, m), 2.10 (3H, s), 1.1-1.90 (14H, m). MS (ESI) m/z 510.94 [M+H]⁺.

Example 7

Compound #87

(S)-1-(2-amino-3-(thiophen-2-yl)propanoyl)-N-cyclohexyl-4-(4-(pyridine-2-sulfonamido)benzyl)piperidine-4-carboxamide hydrochloride

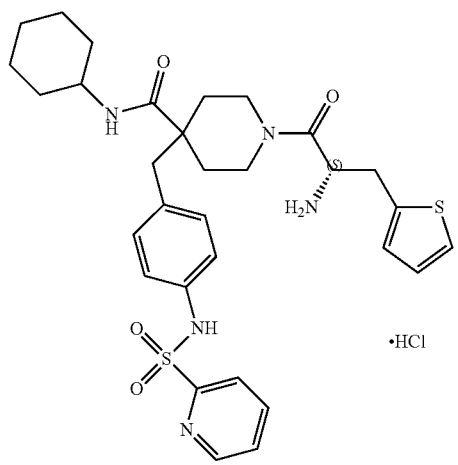

Step A: 1-(2-Amino-3-thiophen-2-yl-propionyl)-4-[4-(pyridine-2-sulfonylamino)-benzyl]-piperidine-4-carboxylic acid cyclohexylamide hydrochloride To a solution of {2-[4-(4-aminobenzyl)-4-cyclohexylcarbamoyl-piperidin-1-yl]-2-oxo-1-thiophen-2-ylmethyl-ethyl}-carbamic acid tert-butyl ester (0.352 mmol; 0.2 g) in 1,2-dichloroethane (5 mL) was added pyridine-2-sulfonyl chloride (0.422 mmol; 0.075 g) and N,N-diisopropyl-N-ethylamine (0.703 mmol; 0.123 mL) and the resulting solution was stirred for 3 hours at room temperature. The resulting mixture was evaporated and the residue was purified via reverse phase HPLC. The desired fractions were combined and lyophilized. The residue was dissolved in tetrahydrofuran (10 mL) and a 4N HCl in 1,4-dioxane solution (15 mL), and the resulting mixture was stirred for 6 hours at room temperature and evaporated. The residue was triturated with diethyl ether and dried under vacuum to yield 4-(4-acetylaminobenzyl)-1-(2-amino-3-thiophen-2-yl-propionyl)-piperidine-4-carboxylic acid cyclohexylamide as a hydrochloride salt.

¹H-NMR (CD₃OD): δ 8.65 (1H, d), 7.94 (2H, m), 7.56 (1H, m), 7.3 (1H, m), 6.87-7.10 (6H, m), 4.62 (1H, m), 4.20 (1H, m), 3.60 (2H, m), 3.30 (4H, m), 2.60-2.80 (2H, m), 1.10-2.10 (14H, m). MS (ESI) m/z 609.87 [M+H]+.

Example 8

Compound #116

(S)-1-(2-amino-3-(thiophen-2-yl)propanoyl)-4-(4-carbamoylbenzyl)-N-(cyclohexylmethyl)piperidine-4-carboxamide hydrochloride

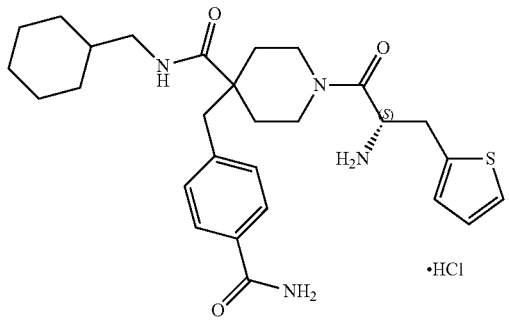

Step A:
4-(4-Carbamoylbenzyl)-piperidine-1,4-dicarboxylic acid mono-tert-butyl ester To a solution of 4-(4-cyanobenzyl)-piperidine-1,4-dicarboxylic acid 1-tert-butyl ester 4-methyl ester (23.04 mmol; 8.26 g) (prepared as in Example 1, but substituting 4-cyanobenzylbromide for 4-biphenylmethyl bromide), in tetrahydrofuran (50 mL) and methanol (50 mL) was added an aqueous 1M NaOH solution (46.1 mmol; 46.1 mL), and the resulting solution was heated to reflux for 48 hours. The mixture was then evaporated and an aqueous 1N HCl solution (50 mL) was added, resulting in the formation of a precipitate. The solid was separated via filtration and dried under vacuum to yield 4-(4-carbamoylbenzyl)-piperidine-1,4-dicarboxylic acid mono-tert-butyl ester. MS (ESI) m/z 384.89 [M+Na]+.

Step B:
4-(4-Carbamoylbenzyl)-piperidine-4-carboxylic acid cyclohexylmethyl amide hydrochloride To a solution of solution of 4-(4-carbamoylbenzyl)-piperidine-1,4-dicarboxylic acid mono-tert-butyl ester (1.38 mmol; 0.5 g) in DMF (5 mL) was added cyclohexylmethylamine (1.18 mmol; 0.154 mL), N,N-diisopropyl-N-ethylamine (2.81 mmol; 0.50 mL) and HBTU (1.38 mmol; 0.51 g), and the resulting mixture was stirred at room temperature overnight. The mixture was purified via reverse phase HPLC. The desired fractions were combined and lyophilized. The residue was dissolved in tetrahydrofuran (2 mL) and a 4N HCl in 1,4-dioxane solution (3 mL), and the resulting mixture was stirred for 4 hours at room temperature and evaporated. The residue was triturated with diethyl ether and dried under vacuum to yield 4-(4-carbamoylbenzyl)-piperidine-4-carboxylic acid cyclohexylmethyl amide as a hydrochloride salt. MS (ESI) m/z 358.40 [M+H]+.

Step C: 1-(2-(S)-Amino-3-thiophen-2-yl-propionyl)-4-(4-carbamoylbenzyl)-piperidine-4-carboxylic acid cyclohexylmethylamide hydrochloride To a solution of 4-(4-carbamoylbenzyl)-piperidine-4-carboxylic acid cyclohexylmethylamide hydrochloride (0.584 mmol; 0.23 g) in DMF (5 mL) was added (S)-2-tert-butoxycarbonylamino-3-thiophen-2-yl-propionic acid (0.642 mmol; 0.174 g), N,N-diisopropyl-N-ethylamine (2.335 mmol; 0.413 mL) and HBTU (0.701 mmol; 0.266 g), and the resulting mixture was stirred at room temperature overnight. The mixture was then purified via reverse phase HPLC and the desired fractions were combined and lyophilized. The resulting residue was dissolved in THF (5 mL) and a 4N HCl solution in 1,4-dioxane (10 mL) was added. The resulting solution was stirred for 5 hours at room temperature and evaporated. The residue was triturated with diethyl ether and dried under vacuum to yield 1-(2-(S)-amino-3-thiophen-2-yl-propionyl)-4-(4-carbamoylbenzyl)-piperidine-4-carboxylic acid cyclohexylmethylamide as a hydrochloride salt.
$^1$H-NMR (CD$_3$OD): 7.80 (2H, m), 7.35 (1H, m), 7.14 (2H, m), 7.00 (1H, m), 6.92 (1H, m), 4.66 (1H, m), 4.21 (1H, m), 3.55-3.70 (2H, m), 3.20-3.40 (6H, m), 2.65-3.00 (2H, m), 0.60-2.15 (15H, m). MS (ESI) m/z 510.98 [M+H]+.

Example 9

Compound #126

(S)-4-(4-(1H-tetrazol-5-yl)benzyl)-1-(2-amino-3-(thiophen-2-yl)propanoyl)-N-cyclohexylpiperidine-4-carboxamide hydrochloride

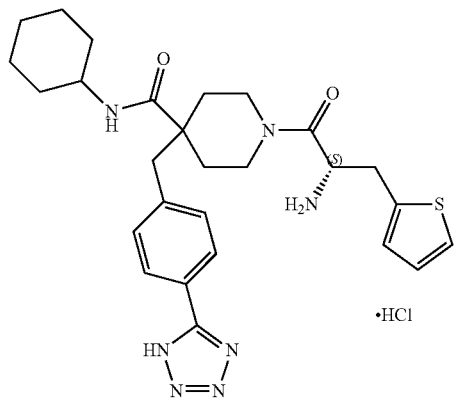

Step A: 1-(2-(S)-Amino-3-thiophen-2-yl-propionyl)-4-[4-(1H-tetrazol-5-yl)-benzyl]-piperidine-4-carboxylic acid cyclohexylamide hydrochloride To a solution of {2-[4-(4-cyanobenzyl)-4-cyclohexylcarbamoyl-piperidin-1-yl]-2-oxo-1-thiophen-2-ylmethyl-ethyl}-carbamic acid tert-butyl ester (9.77 mmol; 5.85 g) (prepared as in Example 1, substituting 4-cyanobenzylbromide for 4-biphenylmethyl bromide and cyclohexylamine for cyclohexylmethylamine), in dimethoxyethane (3 mL) was added trimethylsilyl azide (0.67 mmol; 0.088 mL) and dibutyltin oxide (0.201 mmol; 53.15 mg). The resulting mixture was heated at 100° C. for 18 hours and then purified via reverse phase HPLC. The desired fractions were collected and lyophilized, and the residue was dissolved in THF (2 mL) and a 4N HCl solution in 1,4-dioxane (4 mL) was added. The resulting solution was stirred for 5 hours at room temperature and evaporated. The residue was triturated with diethyl ether and dried under vacuum to yield 1-(2-(S)-amino-3-thiophen-2-yl-propionyl)-4-[4-(1H-tetrazol-5-yl)-benzyl]-piperidine-4-carboxylic acid cyclohexylamide as a hydrochloride salt.
$^1$H-NMR (CD$_3$OD): δ 7.91 (2H, m), 7.40 (1H, d), 7.30 (2H, m), 7.01 (1H, m), 6.92 (1H, d), 4.30 (1H, m), 3.65 (2H, m), 3.00-3.40 (5H, m), 2.60-2.90 (2H, m), 0.60-2.20 (14H, m). MS (ESI) m/z 522.13 [M+H]$^+$.

Example 10

Compound #80

2-[1-(2-(S)-Amino-3-thiophen-2-yl-propionyl)-4-cyclohexylcarbamoyl-piperidin-4-ylmethyl]-benzoic acid hydrochloride

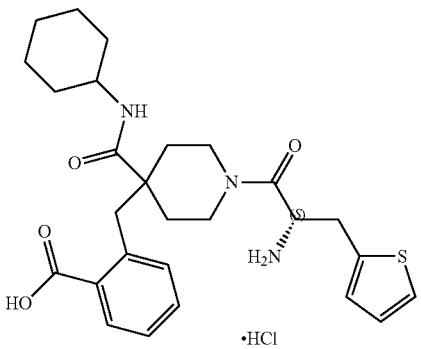

Step A: 2-[1-(2-(S)-Amino-3-thiophen-2-yl-propionyl)-4-cyclohexylcarbamoyl-piperidin-4-ylmethyl]-benzoic acid hydrochloride A solution of {2-[4-(2-Cyano-benzyl)-4-cyclohexylcarbamoyl-piperidin-1-yl]-2-oxo-1-thiophen-2-ylmethylethyl}-carbamic acid tert-butyl ester (0.346 mmol; 200 mg) (prepared as in Example 1, substituting 2-cyanobenzylbromide for 4-biphenylmethyl bromide and cyclohexylamine for cyclohexylmethylamine), in 12N hydrochloric acid (2 mL) was heated to reflux for 3 hours to yield 2-[1-(2-(S)-amino-3-thiophen-2-yl-propionyl)-4-cyclohexylcarbamoyl-piperidin-4-ylmethyl]-benzoic as a hydrochloride salt.

$^1$H-NMR (CD$_3$OD): δ 6.90-7.90 (7H, m), 4.60 (1H, m), 4.20 (1H, m), 3.40-3.70 (2H, m), 3.20-3.40 (4H, m), 2.60-3.10 (2H, m), 1.00-2.50 (14H, m). MS (ESI) m/z 496.70 [M+H]$^+$.

Example 11

Compound #111

4-{[1-(2-(S)-Amino-3-thiophen-2-yl-propionyl)-4-phenyl-piperidine-4-carbonyl]-amino}-trans-cyclohexanecarboxylic acid

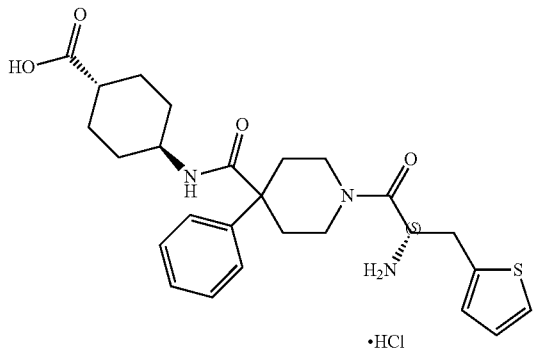

Step A: 4-{[1-(2-(S)-Amino-3-thiophen-2-yl-propionyl)-4-phenyl-piperidine-4-carbonyl]-amino}-trans-cyclohexanecarboxylic acid A solution of (S)-{2-[4-(2-cyanobenzyl)-4-cyclohexylcarbamoyl-piperidin-1-yl]-2-oxo-1-thiophen-2-ylmethylethyl}-carbamic acid tert-butyl ester (0.346 mmol; 200 mg) (prepared by reacting trans-4-amino-cyclohexanecarboxylic acid methyl ester with (S)-2-tert-butoxycarbonylamino-3-thiophen-2-yl-propionic acid), in tetrahydrofuran (1 mL) and methanol (1 mL) was added a 1M NaOH solution (0.376 mmol; 0.376 mL). The resulting mixture was stirred overnight at room temperature. The mixture was then purified via reverse phase HPLC. The desired fractions were combined and lyophilized. The resulting residue was dissolved in tetrahydrofuran (3 mL) and a 4N HCl in dioxane solution (4 mL) was added. The resulting mixture was stirred for 4 hours at room temperature and evaporated. The residue was triturated with diethyl ether to yield 4-{[1-(2-(S)-amino-3-thiophen-2-yl-propionyl)-4-phenyl-piperidine-4-carbonyl]-amino}-trans-cyclohexanecarboxylic acid as a hydrochloride salt.

$^1$H-NMR (CD$_3$OD): δ 7.20-7.40 (6H, m), 6.90-7.04 (2H, m), 7.70 (1H, m), 4.20 (1H, m), 3.57-3.70 (2H, m), 320-3.40 (4H, m), 2.90-3.10 (1H, m), 1.00-2.50 (12H, m). MS (ESI) m/z 484.29 [M+H]$^+$.

Example 12

Compound #133

1-(2-(S)-Amino-3-thiophen-2-yl-propionyl)-4-(3,5-bis-trifluoromethyl-phenyl)-piperidine-4-carboxylic acid cyclohexylmethylamide hydrochloride

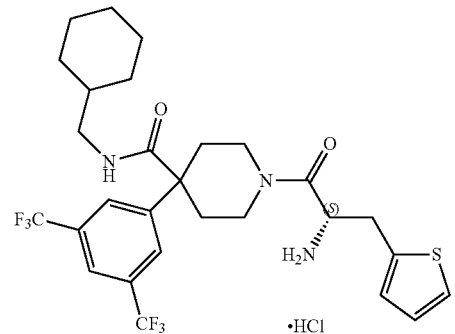

Step A: 4-(3,5-Bis-trifluoromethylphenyl)-piperidine-4-carbonitrile hydrochloride To a solution of (3,5-bis-trifluoromethylphenyl)-acetonitrile (25 mmol; 6.33 g) and bis-(2-chloroethyl)-carbamic acid tert-butyl ester (28 mmol; 6.73 g) in N,N-dimethylformamide (50 mL) under Argon was added sodium hydride (75 mmol; 1.90 g) in small portions over a 30 min period. When the addition was complete, the resulting mixture was heated at 70° C. for 1 hour, then stirred for 2½ days at room temperature. Diethyl ether (250 mL) was added, followed by water (20 mL). The organic layer was separated, washed with brine, dried over magnesium sulfate, filtered, and evaporated. The resulting residue was dissolved in a 4N hydrochloric acid solution (20 mL) and the mixture was stirred for 1 hour at room temperature. The resulting mixture was evaporated and triturated with diethyl ether (50 mL). The solid was separated via centrifugation and purified via reverse phase HPLC. The desired fractions were combined and lyophilized. The resulting residue was dissolved in ethyl acetate (50 mL) and washed with a 1N sodium hydroxide solution (20 mL). The organic phase was dried over magnesium sulfate, filtered and evaporated. The residue was dissolved in diethyl ether, and a 1N HCl solution in diethyl ether (10 mL) was added dropwise. A white precipitate formed that was separated via centrifugation and dried under vacuum to yield 4-(3,5-bis-trifluoromethylphenyl)-piperidine-4-carbonitrile as a hydrochloride salt. MS (ESI) m/z 323.1 [M+H]$^+$.

Step B: 4-(3,5-Bis-trifluoromethylphenyl)-piperidine-1,4-dicarboxylic acid mono-tert-butyl ester A solution of 4-(3,5-bis-trifluoromethylphenyl)-piperidine-4-carbonitrile hydrochloride (1.617 mmol; 580 mg) was dissolved in a 12N hydrochloric acid solution (25 mL) and the resulting mixture was heated to reflux for 3½ days. The mixture was then allowed to cool to room temperature and evaporated to dryness. The residue was dissolved in a 3M sodium hydroxide solution (5 mL) and Boc-anhydride (3.234 mmol; 706 mg) was added. The resulting mixture was stirred at room temperature for 1 hour. The mixture was then acidified with a 2N HCl solution (10 mL) and extracted with diethyl ether (2×100 mL). The combined organic phases were washed with brine, dried over magnesium sulfate, filtered, and evaporated to 4-(3,5-bis-trifluoromethylphenyl)-piperidine-1,4-dicarboxylic acid mono-tert-butyl ester. MS (ESI) m/z 464.1 [M+Na]$^+$.

Step C: 4-(3,5-Bis-trifluoromethylphenyl)-piperidine-4-carboxylic acid cyclohexylmethylamide hydrochloride To a solution of 4-(3,5-bis-trifluoromethylphenyl)-piperidine-1,4-dicarboxylic acid mono-tert-butyl ester (0.5 mmol; 220.7 mg) in DMF (2 mL) was added cyclohexylmethylamine (0.6 mmol; 0.078 mL), N, N-diisopropyl-N-ethylamine (1 mmol; 0.174 mL) and HBTU (0.6 mmol; 228 mg), and the resulting mixture was stirred at room temperature overnight. The mixture was then purified via reverse phase HPLC. The desired fractions were combined and lyophilized. The resulting residue was dissolved in 1,4-dioxane (3 mL) and a 4N HCl solution in 1,4-dioxane (3 mL) was added. The resulting mixture was stirred for 2 hours at room temperature, then evaporated to yield 4-(3,5-bis-trifluoromethylphenyl)-piperidine-4-carboxylic acid cyclohexylmethylamide as a hydrochloride salt. MS (ESI) m/z 437.3 [M+H]$^+$.

Step D: 1-(2-(S)-Amino-3-thiophen-2-yl-propionyl)-4-(3,5-bis-trifluoromethylphenyl)-piperidine-4-carboxylic acid cyclohexylmethylamide hydrochloride To a solution of 4-(3,5-bis-trifluoromethylphenyl)-piperidine-4-carboxylic acid cyclohexylmethylamide hydrochloride (0.169 mmol; 0.08 g) in DMF (3 mL) was added (S)-2-tert-butoxycarbonylamino-3-thiophen-2-yl-propionic acid (0.203 mmol; 55.1 mg), N,N-diisopropyl-N-ethylamine (0.338 mmol; 0.059 mL) and HBTU (0.203 mmol; 77 mg), and the resulting mixture was stirred at room temperature for 20 min. The mixture was then purified via reverse phase HPLC and the desired fractions were combined and lyophilized. The resulting residue was dissolved in 1,4-dioxane (3 mL) and a 4N HCl solution in 1,4-dioxane (3 mL) was added. The resulting solution was stirred for 2 hours at room temperature and evaporated. The residue was triturated with diethyl ether to yield 1-(2-(S)-amino-3-thiophen-2-yl-propionyl)-4-(3,5-bis-trifluoromethylphenyl)-piperidine-4-carboxylic acid cyclohexylmethylamide as a hydrochloride salt.

$^1$H-NMR (DMSO-d$_6$): δ 8.3 (3H, b), 8.0 (1H, s), 7.7-7.8 (2H, s), 7.25 (1H, m), 6.85 (2H, m), 4.7 (1H, m), 4.25 (1H, m), 2.2-3.8 (8H, m), 2.3-3.0 (4H, m), 0.6-2.0 (10H, m). MS (ESI) m/z 590.2 [M+H]$^+$.

Additional compounds of the present invention were prepared according to the processes as described in the Schemes and Examples above. Where sufficient material was prepared, the structure of said compounds was confirmed by $^1$HNMR and/or MS. Where available and confirmed, the measured and calculated molecular weight values are listed in Table 4, below.

TABLE 4

| | Molecular Weight | |
| --- | --- | --- |
| ID No. | Measured (M + H) | Calculated |
| 1 | 463.3 | 462.62 |
| 2 | 449.1 | 448.59 |
| 3 | 544.4 | 543.78 |
| 4 | 516.4 | 515.72 |
| 5 | 476.4 | 475.68 |
| 6 | 546.3 | 545.75 |
| 7 | 566.4 | 569.82 |
| 8 | 530.4 | 529.75 |
| 9 | 528.4 | 527.72 |
| 10 | | 400.57 |
| 11 | 469.3 | 452.66 |
| 12 | | 452.6 |
| 13 | 435.3 | 435.01 |
| 14 | 503.2 | 50.311 |
| 15 | 494.3 | 493.67 |
| 16 | 478.3 | 477.61 |
| 17 | 426.3 | 425.58 |
| 18 | | 468.56 |
| 19 | 537.3 | 536.66 |
| 20 | 521.3 | 520.60 |
| 21 | | 401.55 |
| 22 | 470.3 | 469.65 |
| 23 | | 401.55 |
| 24 | 470.3 | 469.65 |
| 25 | 454.3 | 453.59 |
| 26 | | 436.55 |
| 27 | 505.2 | 504.64 |
| 28 | 489.3 | 488.58 |
| 29 | | 476.66 |
| 30 | 545.3 | 544.76 |
| 31 | | 528.7 |
| 32 | | 514.68 |
| 33 | 531.3 | 530.74 |
| 34 | 514.12 | 513.69 |
| 35 | 472.0 | 471.65 |
| 36 | 473.1 | 472.64 |
| 37 | 514.3 | 513.69 |
| 38 | 494.1 | 493.72 |
| 39 | 478.2 | 477.65 |
| 40 | 574.2 | 573.76 |
| 41 | 580.0 | 579.55 |
| 42 | 531.2 | 530.74 |
| 43 | 532.2 | 531.73 |
| 44 | 561.2 | 560.76 |
| 45 | 587.2 | 586.80 |
| 46 | 561.2 | 560.76 |
| 47 | 560.2 | 559.78 |
| 48 | 565.1 | 565.18 |
| 49 | 547.2 | 546.74 |
| 50 | 531.2 | 530.74 |
| 51 | 555.3 | 554.76 |
| 52 | 574.3 | 573.76 |
| 53 | 598.3 | 597.75 |
| 54 | 587.3 | 589.8 |
| 55 | 574.3 | 573.76 |
| 56 | 579.3 | 578.82 |
| 57 | 567.3 | 566.77 |
| 58 | 551.3 | 550.77 |

TABLE 4-continued

Molecular Weight

| ID No. | Measured (M + H) | Calculated |
|---|---|---|
| 59 | 525.3 | 524.73 |
| 60 | 573.3 | 572.78 |
| 61 | 497.3 | 496.68 |
| 62 | 498.2 | 497.66 |
| 66 | 455.2 | 454.64 |
| 67 |  | 386.54 |
| 68 | 439.3 | 438.58 |
| 69 | 440.3 | 439.62 |
| 70 |  | 371.53 |
| 71 | 455.2 | 454.64 |
| 72 |  | 386.54 |
| 73 | 558.2 | 557.54 |
| 74 | 590.1 | 589.51 |
| 75 | 424.2 | 423.56 |
| 77 | 512.1 | 511.45 |
| 78 | 564.2 | 564.2 |
| 79 | 483.0 | 482.59 |
| 80 | 496.7 | 497.66 |
| 81 | 499.5 | 498.65 |
| 82 | 479.0 | 478.66 |
| 83 | 416.2 | 415.58 |
| 84 | 484.1 | 483.68 |
| 85 | 456.3 | 455.62 |
| 86 | 454.0 | 453.65 |
| 87 | 609.9 | 609.82 |
| 88 | 547.0 | 546.76 |
| 89 | 600.7 | 600.73 |
| 90 | 510.9 | 510.7 |
| 91 | 454.4 | 453.65 |
| 92 | 658.2 | 658.44 |
| 95 | 468.7 | 468.67 |
| 96 | 580.2 | 579.55 |
| 97 | 532.3 | 531.73 |
| 98 | 547.3 | 546.74 |
| 99 | 555.3 | 554.76 |
| 100 | 598.3 | 597.75 |
| 101 | 574.2 | 573.76 |
| 102 | 574.4 | 573.76 |
| 103 | 442.1 | 441.6 |
| 104 | 456.1 | 455.62 |
| 106 | 536.2 | 535.8 |
| 107 | 552.3 | 551.8 |
| 108 | 538.3 | 537.75 |
| 109 | 498.1 | 497.66 |
| 110 | 512.1 | 511.69 |
| 111 | 484.2 | 483.63 |
| 112 | 498.1 | 497.66 |
| 113 | 498.0 | 497.66 |
| 114 | 443.2 | 442.61 |
| 115 | 484.4 | 48363 |
| 116 | 511.0 | 510.7 |
| 117 | 512.9 | 512.68 |
| 118 | 476.2 | 475.46 |
| 120 | 592.2 | 591.62 |
| 121 | 471.3 | 470.64 |
| 122 | 443.9 | 442.58 |
| 123 | 560.4 | 559.78 |
| 124 | 492.5 | 492.69 |
| 125 | 494.8 | 494.66 |
| 126 | 522.1 | 521.69 |
| 127 | 536.1 | 535.72 |
| 128 | 538.1 | 537.69 |
| 129 | 468.2 | 467.68 |
| 130 | 470.4 | 469.65 |
| 131 | 470.4 | 469.65 |
| 133 | 590.2 | 589.65 |
| 134 | 468.3 | 467.68 |
| 136 | 415.2 | 414.6 |
| 138 | 386.2 | 385.55 |
| 139 | 402.3 | 401.55 |
| 152 | 469.1 | 468.67 |

Biological Example 1

DPP-1 Inhibition Assay (In Vitro)

Test compounds were assessed for DPP-1 (Cathepsin C) inhibitory activity using a fluorogenic substrate, GR-AMC (Glycine-Arginine-amino-4-methylcoumarin, Bachem, I-1215). The amount of amino-methylcoumarin released is proportional to the DPP-1 activity, and the reaction is monitored kinetically with a Molecular Devices plate reader using black 96-well plates.

All compounds were tested under room temperature conditions. The assay buffer consisted of 50 mM HEPES, pH 7.0, 100 mM NaCl, 2 mM glutathione (GSH), and 0.002% TWEEN 20. GSH and TWEEN 20 were added to the buffer fresh daily. Just prior to use, an in-house preparation of recombinant human DPP-1 (240 μM stock, MW 49.6 kD) was diluted 600-fold in assay buffer containing fresh 2 mM dithiothreitol (DTT) to activate the enzyme, then diluted into assay buffer (without DTT) 133-fold for a DPP-1 working solution of 3 nM. Test compounds were diluted in DMSO for 20× their final assay concentrations.

Additions to a 96-well black Costar 3915 plates were as follows: 90 μL of 11 μM GR-AMC, 5 μL test compound (followed by mixing), and 5 μL 3 nM DPP-1 to start the reaction. Fluorescent reactions were monitored kinetically at 360 nm excitation, 440 nm emission on a Molecular Devices Spectramax XPS reader. The Softmax Pro software of the reader determined the initial velocity of the selected data (the first 3-5 minutes of the reaction), and the best linear regression fit of the initial kinetic data. Final assay conditions were 0.15 nM DPP-1, 10 uM GR-AMC, 50 mM HEPES, pH 7.0, 100 mM NaCl, 2 mM GSH, 0.002% TWEEN 20, 1 uM DTT, 5.0% DMSO. Initial velocity rates were plotted vs. test compound concentration by use of a four-parameter logistics equation (nonlinear regression, sigmoidal dose-response (variable slope), with fixed Hill (1.0) using GraphPad Prism® software for determination of DPP-1 $IC_{50}$. Within-run assay coefficient of variation (CV) was generally <10%; between-run CV <20%.

Representative compounds of the present invention were tested according to the procedure as described above, with results as listed in Table 5, below. Where a compound was tested according to the above procedure multiple times, the average value is listed in the Table 5, below.

TABLE 5

| DPP-1 Inhibition | |
|---|---|
| ID No. | $IC_{50}$ (μM) |
| 1 | 1.8 |
| 2 | >10[d] |
| 3 | 0.084 |
| 4 | 0.43 |
| 5 | 3.0 |
| 6 | 0.074 |
| 7 | 1.3 |
| 8 | 0.035 |
| 9 | 0.93 |
| 10 | ~5 |
| 11 | 0.22 |
| 12 | ~5 |
| 13 | 4.3 |
| 14 | 0.35 |
| 15 | 0.083 |
| 16 | 1.2 |
| 17 | 4.4 |
| 18 | 5.4 |

TABLE 5-continued

DPP-1 Inhibition

| ID No. | IC$_{50}$ (μM) |
|---|---|
| 19 | 0.4 |
| 20 | 3.1 |
| 21 | 7.4 |
| 22 | 0.093 |
| 23 | 8.2 |
| 24 | 0.099 |
| 25 | 1.8 |
| 26 | 6.1 |
| 27 | 0.22 |
| 28 | 1.7 |
| 29 | 9.5 |
| 30 | 0.88 |
| 31 | 5.8 |
| 32 | ~20 |
| 33 | 0.23 |
| 35 | >20[d] |
| 36 | 0.6 |
| 37 | 0.23 |
| 38 | 0.75 |
| 39 | 18 |
| 40 | 0.035 |
| 41 | 0.037 |
| 42 | 0.029 |
| 43 | 0.029 |
| 44 | 0.029 |
| 45 | 0.052 |
| 46 | 0.038 |
| 47 | 0.034 |
| 48 | 0.039 |
| 49 | 0.024 |
| 50 | 0.035 |
| 51 | 0.035 |
| 52 | 0.1 |
| 53 | 0.14 |
| 54 | 0.031 |
| 55 | 0.1 |
| 56 | 0.049 |
| 57 | 0.0363 |
| 58 | 0.073 |
| 59 | 0.086 |
| 60 | 0.033 |
| 61 | 0.047 |
| 62 | 0.36 |
| 66 | 0.054 |
| 67 | 9.1 |
| 68 | 0.91 |
| 69 | 0.073 |
| 70 | 9.4 |
| 71 | 0.037 |
| 72 | 5.0 |
| 73 | 0.25 |
| 74 | >20[d] |
| 75 | 2.8 |
| 77 | 2.3 |
| 78 | 5.6 |
| 79 | 0.62 |
| 80 | 0.22 |
| 81 | 0.024 |
| 82 | 0.11 |
| 83 | 9.5 |
| 84 | 0.056 |
| 85 | 0.11 |
| 86 | 0.04 |
| 87 | 0.02 |
| 88 | 0.031 |
| 89 | 0.15 |
| 90 | 0.049 |
| 91 | 0.023 |
| 92 | 5.6 |
| 95 | 0.063 |
| 96 | 0.084 |
| 97 | 0.039 |
| 98 | 0.045 |
| 99 | 0.046 |
| 100 | 0.12 |
| 101 | 0.14 |
| 102 | 0.19 |
| 103 | 0.31 |
| 104 | 0.076 |
| 106 | 5.6 |
| 107 | >20[d] |
| 108 | ~4 |
| 109 | 0.025 |
| 110 | 0.17 |
| 111 | 0.089 |
| 112 | 0.2 |
| 113 | 0.07 |
| 114 | 0.22 |
| 115 | 0.2 |
| 116 | 0.05 |
| 117 | 0.33 |
| 118 | 3.4 |
| 120 | 0.23 |
| 121 | 0.13 |
| 122 | 1.3 |
| 123 | 0.82 |
| 124 | 0.027 |
| 125 | 0.16 |
| 126 | 0.17 |
| 127 | 0.083 |
| 128 | 0.69 |
| 129 | 0.017 |
| 130 | 0.041 |
| 131 | 0.14 |
| 133 | 0.067 |
| 134 | 0.016 |
| 136 | 6.5 |
| 138 | 1.7 |
| 139 | 2.6 |
| 152 | 0.82 |

[d]For these compounds, the number of different concentrations tested was not sufficient to calculate an IC$_{50}$ value beyond a determination that it was greater than about 10 μM or greater than about 20 μM, as noted.

Solid, Oral Formulation

Prophetic Example

As a specific embodiment of an oral composition, 100 mg of the Compound #3, prepared as in Example 1, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A compound of formula (I)

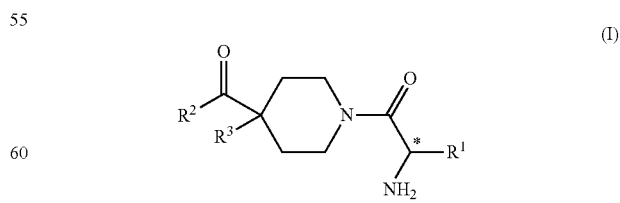

wherein $R^1$ is selected from the group consisting of $C_{2-4}$alkynyl, —$CH_2$—CN, —CH(OH)—$CH_3$, —($C_{1-2}$alkyl)-O—($C_{1-2}$alkyl), —($C_{1-2}$alkyl)-S—($C_{1-2}$alkyl), —($C_{1-2}$ alkyl)-SO—($C_{1-2}$alkyl), —($C_{1-2}$alkyl)-$SO_2$—($C_{1-2}$ alkyl), —$CH_2$-(5 to 6 membered heteroaryl) and —CH(OH)-(5 to 6 membered heteroaryl);

wherein the 5 to 6 membered heteroaryl, whether alone or as part of a substituent group, is optionally substituted with a halogen;

$R^2$ is selected from the group consisting of —O-$Q^1$ and —$NR^A$-$Q^1$;

$R^A$ is selected from the group consisting of hydrogen and methyl;

$Q^1$ is selected from the group consisting of hydrogen, $C_{1-4}$-alkyl, $C_{3-8}$cycloalkyl, —$CH_2$—($C_{3-8}$cycloalkyl), heterocyclyl and —$CH_2$-(heterocyclyl);

wherein the $C_{3-8}$cycloalkyl or heterocyclyl, whether alone or as part of a substituent group is optionally substituted with one or more substituents independently selected from the group consisting of halogen, hydroxy, $C_{1-4}$-alkyl, trifluoromethyl, $C_{1-4}$-alkoxy, cyano, amino, ($C_{1-4}$alkyl)amino, di($C_{1-4}$-alkyl)amino, —$CO_2H$ and —C(O)—O—($C_{1-4}$-alkyl);

alternatively, $R^A$ and $Q^1$ are taken together with the nitrogen atom to which they are bound to form a ring structure selected from the group consisting of piperidinyl, piperazinyl, pyrrolidinyl, morpholinyl, azepinyl, azetadinyl and decahydro-isoquinolin-2-yl;

$R^3$ is selected from the group consisting of (a) phenyl; wherein the phenyl is optionally substituted with one or more substituents independently selected from the group consisting of halogen, cyano, nitro, $NR^BR^C$, $C_{1-4}$-alkyl, trifluoromethyl, $C_{1-4}$-alkoxy, —$CO_2H$, —C(O)—$NR^DR^E$, —NH—C(O)—($C_{1-4}$-alkyl), —NH—$SO_2$—($C_{1-4}$alkyl), —NH—$SO_2$—$CF_3$ and —NH—$SO_2$-(pyridyl);

wherein $R^B$ and $R^C$ are each independently selected from the group consisting of hydrogen and $C_{1-4}$-alkyl;

and wherein $R^D$ is selected from the group consisting of hydrogen and $C_{1-4}$-alkyl; and $R^E$ is selected from the group consisting of hydrogen, $C_{1-4}$-alkyl, $C_{3-8}$cycloalkyl and phenyl;

(b) —($CH_2$)—$R^4$; wherein $R^4$ is selected from the group consisting of phenyl, pyridyl, pyrimidinyl and thiazolyl;

wherein the phenyl, pyridyl, pyrimidinyl or thiazolyl is optionally substituted with one or more substituents independently selected from the group consisting of halogen, cyano, nitro, $NR^FR^G$, $C_{1-4}$-alkyl, trifluoromethyl, $C_{1-4}$-alkoxy, —$CO_2H$, —C(O)—$NR^HR^J$, —NH—C(O)—($C_{1-4}$alkyl), —NH—$SO_2$—($C_{1-4}$alkyl), —NH—$SO_2$—$CF_3$ and —NH—$SO_2$-(pyridyl);

wherein $R^F$ and $R^G$ are each independently selected from the group consisting of hydrogen and $C_{1-4}$-alkyl;

and wherein $R^H$ is selected from the group consisting of hydrogen and $C_{1-4}$-alkyl; and $R^J$ is selected from the group consisting of hydrogen, $C_{1-4}$-alkyl, $C_{3-8}$cycloalkyl and phenyl;

alternatively, $R^H$ and $R^J$ are taken together with the nitrogen atom to which they are bound to form a ring structure selected from the group consisting of piperidinyl, piperazinyl, pyrrolidinyl, morpholinyl, azepinyl and azetadinyl;

and (c) —$CH_2$-phenyl-$Q^2$;

wherein $Q^2$ is selected from the group consisting of phenyl, pyridyl, pyrimidinyl, imidazolyl, thiazolyl, triazolyl, tetrazolyl and benzo[d][1,3]dioxolyl;

and wherein the $Q^2$ phenyl or pyridyl is optionally substituted with one or more substituents independently selected from halogen, hydroxy, cyano, $C_{1-4}$-alkyl, trifluoromethyl, $C_{1-4}$alkoxy, —$NR^KR^L$, —NH—C(O)—($C_{1-4}$-alkyl), —$CO_2H$ and —C(O)—O—($C_{1-4}$-alkyl);

and wherein $R^K$ and $R^L$ are each independently selected from the group consisting of hydrogen and $C_{1-4}$-alkyl;

provided that when $R^1$ is —CH(OH)—$CH_3$ and $R^3$ is phenyl, then $R^2$ is other than ethoxy;

or a pharmaceutically acceptable salt thereof.

2. A compound as in claim 1, wherein $R^1$ is selected from the group consisting of $C_{2-4}$alkynyl, —$CH_2$—CN, —CH(OH)—$CH_3$, —($C_{1-2}$alkyl)-O—($C_{1-2}$alkyl), —($C_{1-2}$alkyl)-S—($C_{1-2}$alkyl), —($C_{1-2}$alkyl)-SO—($C_{1-2}$alkyl), —($C_{1-2}$alkyl)-$SO_2$—($C_{1-2}$alkyl), —$CH_2$-(5 to 6 membered heteroaryl) and —CH(OH)-(5 to 6 membered heteroaryl);

wherein the 5 to 6 membered heteroaryl, whether alone or as part of a substituent group, is optionally substituted with a halogen;

$R^2$ is selected from the group consisting of —O-$Q^1$ and —$NR^A$-$Q^1$;

$R^A$ is selected from the group consisting of hydrogen and methyl;

$Q^1$ is selected from the group consisting of hydrogen, $C_{1-4}$-alkyl, $C_{3-6}$cycloalkyl, —$CH_2$—($C_{3-6}$cycloalkyl), 5 to 6 membered heterocyclyl and —$CH_2$-(5 to 6 membered heterocyclyl);

wherein the $C_{3-6}$cycloalkyl or 5 to 6 membered heterocyclyl, whether alone or as part of a substituent group is optionally substituted with one to two substituents independently selected from the group consisting of halogen, hydroxy, $C_{1-4}$-alkyl, trifluoromethyl, —$CO_2H$ and —C(O)—O—($C_{1-4}$-alkyl);

alternatively, $R^A$ and $Q^1$ are taken together with the nitrogen atom to which they are bound to form a ring structure selected from the group consisting of piperidinyl, piperazinyl, pyrrolidinyl, morpholinyl and decahydro-isoquinolin-2-yl;

$R^3$ is selected from the group consisting of (a) phenyl; wherein the phenyl is optionally substituted with one to two substituents independently selected from the group consisting of halogen, cyano, nitro, $NR^BR^C$, $C_{1-4}$alkyl, trifluoromethyl, —$CO_2H$ and —C(O)—$NR^DR^E$;

wherein $R^B$ and $R^C$ are each independently selected from the group consisting of hydrogen and $C_{1-2}$alkyl;

and wherein $R^D$ is selected from the group consisting of hydrogen and $C_{1-4}$-alkyl; and $R^E$ is selected from the group consisting of hydrogen, $C_{1-4}$-alkyl, $C_{3-8}$cycloalkyl and phenyl;

(b) —($CH_2$)—$R^4$; wherein $R^4$ is selected from the group consisting of phenyl and pyridyl;

wherein the phenyl or pyridyl is optionally substituted with one to two substituents independently selected from the group consisting of halogen, cyano, nitro, $NR^FR^G$, $C_{1-4}$-alkyl, trifluoromethyl, $C_{1-4}$alkoxy, —$CO_2H$, —C(O)—$NR^HR^J$, —NH—C(O)—($C_{1-4}$alkyl), —NH—$SO_2$—($C_{1-4}$alkyl), —NH—$SO_2$—$CF_3$ and —NH—$SO_2$-(pyridyl);

wherein $R^F$ and $R^G$ are each independently selected from the group consisting of hydrogen and $C_{1-2}$alkyl;

wherein $R^H$ is selected from the group consisting of hydrogen and $C_{1-4}$-alkyl; and $R^J$ is selected from the group consisting of hydrogen, $C_{1-4}$alkyl, $C_{3-6}$cycloalkyl and phenyl; alternatively, $R^H$ and $R^J$ are taken together with the nitrogen atom to which they are bound to form a ring structure selected from the group consisting of piperidinyl, piperazinyl, pyrrolidinyl and morpholinyl;

and (c) —CH$_2$-phenyl-Q$^2$; wherein Q$^2$ is selected from the group consisting of phenyl, pyridyl, pyrimidinyl, tetrazolyl and benzo[d][1,3]dioxolyl;

and wherein the Q$^2$ phenyl or pyridyl is optionally substituted with one to two substituents independently selected from halogen, hydroxy, cyano, trifluoromethyl, C$_{1-4}$-alkoxy, —NR$^K$R$^L$, —NH—C(O)—(C$_{1-4}$alkyl), —CO$_2$H and —C(O)—O—(C$_{1-4}$alkyl); and wherein R$^K$ and R$^L$ are each independently selected from the group consisting of hydrogen and C$_{1-4}$-alkyl;

provided that when R$^1$ is —CH(OH)—CH$_3$ and R$^3$ is phenyl, then R$^2$ is other than ethoxy;

or a pharmaceutically acceptable salt thereof.

3. A compound as in claim 2, wherein

R$^1$ is selected from the group consisting of C$_{2-4}$alkynyl, —CH(OH)—CH$_3$, —CH$_2$—CN, —(C$_{1-2}$alkyl)-O—(C$_{1-2}$alkyl), —(C$_{1-2}$alkyl)-S—(C$_{1-2}$alkyl), —(C$_{1-2}$alkyl)-SO—(C$_{1-2}$alkyl), —(C$_{1-2}$alkyl)-SO$_2$—(C$_{1-2}$alkyl), —CH$_2$-(5 membered heteroaryl) and —CH(OH)-(5 membered heteroaryl); wherein the 5 membered heteroaryl is optionally substituted with a halogen;

R$^2$ is selected from the group consisting of —OH, —OCH$_3$, —O—CH$_2$—(C$_{5-6}$cycloalkyl) and —NR$^A$-Q$^1$;

R$^A$ is selected from the group consisting of hydrogen and methyl;

Q$^1$ is selected from the group consisting of C$_{5-6}$cycloalkyl, —CH$_2$—(C$_{5-6}$cycloalkyl), 5 to 6 membered saturated heterocyclyl and —CH$_2$-(5 to 6 membered heterocyclyl); wherein the C$_{5-6}$cycloalkyl or 5 to 6 membered heterocyclyl, whether alone or as part of a substituent group is optionally substituted with a substituent selected form the group consisting of hydroxy, C$_{1-2}$alkyl, —CO$_2$H and —C(O)—O—(C$_{1-2}$alkyl)

alternatively, R$^A$ and Q$^1$ are taken together with the nitrogen atom to which they are bound to form a ring structure selected form the group consisting of piperidin-1yl, morpholin-4-yl and decahydro-isoquinolin-2-yl;

R$^3$ is selected from the group consisting of (a) phenyl; wherein the phenyl is optionally substituted with one to two substituent independently selected from the group consisting of C$_{1-2}$alkyl and trifluoromethyl;

(b) —CH$_2$—R$^4$; wherein R$^4$ is selected from the group consisting of phenyl and pyridyl;

wherein the phenyl is optionally substituted with one to two substituents independently selected from the group consisting of halogen, trifluoromethyl, C$_{1-2}$alkoxy, cyano, nitro, amino, —CO$_2$H, —C(O)—NR$^H$R$^J$, —NH—C(O)—(C$_{1-2}$alkyl), —NH—SO$_2$—(C$_{1-2}$alkyl), —NH—SO$_2$—CF$_3$ and —NH—SO$_2$-(pyridyl);

wherein R$^H$ is selected from the group consisting of hydrogen and C$_{1-2}$alkyl; and R$^J$ is selected from the group consisting of hydrogen, C$_{1-2}$alkyl, C$_{5-6}$cycloalkyl and phenyl; alternatively, R$^H$ and R$^J$ are taken together with the nitrogen atom to which they are bound to form a ring structure selected from the group consisting of pyrrolidinyl and morpholinyl;

and (c) —CH$_2$-(phenyl)-Q$^2$; wherein Q$^2$ is selected from the group consisting of phenyl, pyridyl, pyrimidinyl, tetrazolyl and benzo[d][1,3]dioxolyl;

and wherein the Q$^2$ phenyl or pyridyl is optionally substituted with a substituent selected from the group consisting of halogen, hydroxy, cyano, trifluoromethyl, C$_{1-2}$alkoxy, —NH—C(O)—(C$_{1-2}$alkyl) and CO$_2$H;

or a pharmaceutically acceptable salt thereof.

4. A compound as in claim 3, wherein

R$^1$ is selected from the group consisting of n-propyn-2-yl, 1R-hydroxyethyl, —CH$_2$—CN, -(methyl)-O-(methyl), -(methyl)-S-(methyl), -(ethyl)-S-(methyl), -(ethyl)-S-(ethyl), -(ethyl)-SO-(ethyl), -(ethyl)-SO$_2$-(ethyl), —CH$_2$-(fur-2-yl), —CH$_2$-(thien-2-yl), —CH$_2$-(4-bromo-thien-2-yl), —CH$_2$-(5-chloro-thien-2-yl), —CH$_2$-(imidazolyl-4-yl), —CH$_2$-(thiazol-2-yl), —CH$_2$-(pyrazol-1-yl), —CH$_2$-(1,2,4-triazol-1-yl) and —CH(OH)-(thien-2-yl);

R$^2$ is selected from the group consisting of hydroxy, methoxy, cyclohexyl-methoxy-, morpholin-4-yl, piperidin-1-yl, decahydro-isoquinolin-2-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-;

R$^3$ is selected from the group consisting of phenyl, 4-methylphenyl, 3,5-di(trifluoromethyl)phenyl, —CH$_2$-phenyl, —CH$_2$-(4-chlorophenyl), —CH$_2$-(3-iodophenyl), —CH$_2$-(4-iodophenyl), —CH$_2$-(2-cyanophenyl), —CH$_2$-(4-cyanophenyl), —CH$_2$-(4-nitrophenyl), —CH$_2$-(4-aminophenyl), —CH$_2$-(4-trifluoromethylphenyl), —CH$_2$-(2-carboxyphenyl), —CH$_2$-(4-carboxyphenyl), —CH$_2$-(3-methoxyphenyl), —CH$_2$-(2,4-difluorophenyl), —CH$_2$-(4-(amino-carbonyl)-phenyl), —CH$_2$-(4-(cyclohexyl-amino-carbonyl)-phenyl), —CH$_2$-(4-(phenyl-amino-carbonyl)-phenyl), —CH$_2$-(4-(dimethyl-amino-carbonyl)-phenyl), —CH$_2$-(4-(morpholin-4-yl-carbonyl)-phenyl), —CH$_2$-(4-(pyrrolidin-1-yl-carbonyl)-phenyl), —CH$_2$-(4-(methyl-sulfonyl-amino)-phenyl), —CH$_2$-(4-(trifluoromethyl-sulfonyl-amino)-phenyl), —CH$_2$-(4-(pyrid-2-yl-sulfonyl-amino)-phenyl), —CH$_2$-(4-(methyl-carbonyl-amino)-phenyl), —CH$_2$-(pyrid-3-yl), —CH$_2$-(pyrid-4-yl), —CH$_2$-(3-(phenyl)-phenyl), —CH$_2$-(4-(phenyl)-phenyl), —CH$_2$-(4-(4-cyanophenyl)-phenyl), —CH$_2$-(4-(3-methoxyphenyl)-phenyl), —CH$_2$-(3-(3-carboxyphenyl)-phenyl), —CH$_2$-(3-(4-carboxyphenyl)-phenyl), —CH$_2$-(4-(3-carboxyphenyl)-phenyl), —CH$_2$-(4-(4-carboxyphenyl)-phenyl), —CH$_2$-(3-(4-trifluoromethylphenyl)-phenyl), —CH$_2$-(4-(4-trifluoromethylphenyl)-phenyl), —CH$_2$-(4-(2-methyl-carbonyl-amino-phenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl), —CH$_2$-(4-(tetrazol-5-yl)-phenyl) and —CH$_2$-(4-(benzo[d][1,3]dioxol-5-yl)-phenyl);

or a pharmaceutically acceptable salt thereof.

5. A compound as in claim 4, wherein $R^1$ is selected from the group consisting of —$CH_2$—CN, -(methyl)-S-(methyl), -(ethyl)-S-(methyl), —$CH_2$-(fur-2-yl), —$CH_2$-(thien-2-yl), —$CH_2$-(imidazolyl-4-yl), —$CH_2$-(thiazol-2-yl) and —CH(OH)-(thien-2-yl);

$R^2$ is selected from the group consisting of cyclohexyl-methoxy-, piperidin-1-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino-, 1-methyl-piperidin-4-yl-methyl-amino- and 4,5-dihydro-thiazol-2-yl-amino-;

$R^3$ is selected from the group consisting of phenyl, 4-methylphenyl, 3,5-di(trifluoromethyl)phenyl, —$CH_2$-phenyl, —$CH_2$-(4-chlorophenyl), —$CH_2$-(3-iodophenyl), —$CH_2$-(4-iodophenyl), —$CH_2$-(2-cyanophenyl), —$CH_2$-(4-cyanophenyl), —$CH_2$-(4-nitrophenyl), —$CH_2$-(4-aminophenyl), —$CH_2$-(4-trifluoromethylphenyl), —$CH_2$-(2-carboxyphenyl), —$CH_2$-(4-carboxyphenyl), —$CH_2$-(3-methoxyphenyl), —$CH_2$-(2,4-difluorophenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-yl-carbonyl)-phenyl), —$CH_2$-(4-(pyrrolidin-1-yl-carbonyl)-phenyl), —$CH_2$-(4-(methyl-sulfonyl-amino)-phenyl), —$CH_2$-(4-(trifluoromethyl-sulfonyl-amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl), —$CH_2$-(pyrid-4-yl), —$CH_2$-(3-(phenyl)-phenyl), —$CH_2$-(4-(phenyl)-phenyl), —$CH_2$-(4-(4-cyanophenyl)-phenyl), —$CH_2$-(4-(3-methoxyphenyl)-phenyl), —$CH_2$-(3-(3-carboxyphenyl)-phenyl), —$CH_2$-(3-(4-carboxyphenyl)-phenyl), —$CH_2$-(4-(3-carboxyphenyl)-phenyl), —$CH_2$-(4-(4-carboxyphenyl)-phenyl), —$CH_2$-(3-(4-trifluoromethyl-phenyl)-phenyl), —$CH_2$-(4-(4-trifluoromethyl-phenyl)-phenyl), —$CH_2$-(4-(2-methyl-carbonyl-amino-phenyl)-phenyl), —$CH_2$-(4-(3-methyl-carbonyl-amino-phenyl)-phenyl), —$CH_2$-(4-(pyrid-3-yl)-phenyl), —$CH_2$-(4-(pyrid-4-yl)-phenyl), —$CH_2$-(4-(2-methoxy-pyrdi-3-yl)-phenyl), —$CH_2$-(4-(6-methoxy-pyrid-3-yl)-phenyl), —$CH_2$-(4-(2-chloro-pyrid-3-yl)-phenyl), —$CH_2$-(3-(6-hydroxy-pyrid-3-yl)-phenyl), —$CH_2$-(4-(6-hydroxy-pyrid-3-yl)-phenyl), —$CH_2$-(3-(pyrimidin-5-yl)-phenyl), —$CH_2$-(4-(pyrimidin-5-yl)-phenyl), —$CH_2$-(4-(tetrazol-5-yl)-phenyl) and —$CH_2$-(4-(benzo[d][1,3]dioxol-5-yl)-phenyl);

and wherein the starred stereo-center is present in an enantiomeric excess of the stereo-configuration wherein the amino group is in the down orientation;

or a pharmaceutically acceptable salt thereof.

6. A compound as in claim 4, wherein $R^1$ is selected from the group consisting of -(ethyl)-S-(methyl), —$CH_2$-(fur-2-yl), —$CH_2$-(thien-2-yl) and —$CH_2$-(thiazol-2-yl);

$R^2$ is selected from the group consisting of cyclohexyl-methoxy-, piperidin-1-yl, cyclohexyl-amino, cyclohexyl-methyl-amino-, 4-hydroxy-cyclohexyl-amino-, trans-(1-(4-hydroxy-cyclohexyl)-amino)-, trans-(1-(4-methoxycarbonyl-cyclohexyl)-amino)-, trans-(1-(4-methoxycarbonyl-cyclohexyl)-methyl-amino)-, trans-(1-(4-carboxy-cyclohexyl)-amino)-, trans-(1-(4-carboxy-cyclohexyl)-methyl-amino)-, trans-(1-(4-methoxycarbonyl-cyclohexyl)-amino)-, trans-(1-(4-carboxy-cyclohexyl)-amino)-, N-methyl-N-(cyclohexyl-methyl)-amino-, tetrahydropyran-4-yl-amino-, tetrahydropyran-4-yl-methyl-amino- and 4,5-dihydro-thiazol-2-yl-amino-;

$R^3$ is selected from the group consisting of phenyl, 4-methylphenyl, 3,5-di(trifluoromethyl)phenyl, —$CH_2$-phenyl, —$CH_2$-(4-chlorophenyl), —$CH_2$-(3-iodophenyl), —$CH_2$-(4-iodophenyl), —$CH_2$-(2-cyanophenyl), —$CH_2$-(4-cyanophenyl), —$CH_2$-(4-nitrophenyl), —$CH_2$-(4-aminophenyl), —$CH_2$-(4-trifluoromethylphenyl), —$CH_2$-(2-carboxyphenyl), —$CH_2$-(4-carboxyphenyl), —$CH_2$-(3-methoxyphenyl), —$CH_2$-(2,4-difluorophenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-yl-carbonyl)-phenyl), —$CH_2$-(4-(pyrrolidin-1-yl-carbonyl)-phenyl), —$CH_2$-(4-(methyl-sulfonyl-amino)-phenyl), —$CH_2$-(4-(trifluoromethyl-sulfonyl-amino)-phenyl), —$CH_2$-(4-(pyrid-2-yl-sulfonyl-amino)-phenyl), —$CH_2$-(4-(methyl-carbonyl-amino)-phenyl), —$CH_2$-(pyrid-3-yl), —$CH_2$-(pyrid-4-yl), —$CH_2$-(4-(phenyl)-phenyl), —$CH_2$-(4-(4-cyanophenyl)-phenyl), —$CH_2$-(4-(3-methoxyphenyl)-phenyl), —$CH_2$-(3-(3-carboxyphenyl)-phenyl), —$CH_2$-(3-(4-carboxyphenyl)-phenyl), —$CH_2$-(4-(3-carboxyphenyl)-phenyl), —$CH_2$-(4-(4-carboxyphenyl)-phenyl), —$CH_2$-(3-(4-trifluoromethyl-phenyl)-phenyl), —$CH_2$-(4-(4-trifluoromethyl-phenyl)-phenyl), —$CH_2$-(4-(2-methyl-carbonyl-amino-phenyl)-phenyl), —$CH_2$-(4-(3-methyl-carbonyl-amino-phenyl)-phenyl), —$CH_2$-(4-(pyrid-3-yl)-phenyl), —$CH_2$-(4-(pyrid-4-yl)-phenyl), —$CH_2$-(4-(2-methoxy-pyrdi-3-yl)-phenyl), —$CH_2$-(4-(6-methoxy-pyrid-3-yl)-phenyl), —$CH_2$-(4-(2-chloro-pyrid-3-yl)-phenyl), —$CH_2$-(3-(6-hydroxy-pyrid-3-yl)-phenyl), —$CH_2$-(4-(6-hydroxy-pyrid-3-yl)-phenyl), —$CH_2$-(3-(pyrimidin-5-yl)-phenyl), —$CH_2$-(4-(pyrimidin-5-yl)-phenyl), —$CH_2$-(4-(tetrazol-5-yl)-phenyl) and —$CH_2$-(4-(benzo[d][1,3]dioxol-5-yl)-phenyl);

and wherein the starred stereo-center is present in an enantiomeric excess of the (S)-stereo-configuration;

or a pharmaceutically acceptable salt thereof.

7. A compound as in claim 4, wherein $R^1$ is —$CH_2$-(thien-2-yl);

$R^2$ is selected from the group consisting of cyclohexyl-methoxy-, cyclohexyl-amino, cyclohexyl-methyl-amino-, trans-(1-4-methoxycarbonyl-cyclohexyl)-amino)-, trans-(1-(4-carboxy-cyclohexyl)-amino)-, trans-(1-(4-methoxycarbonyl-cyclohexyl)-amino)-, N-methyl-N-(cyclohexyl-methyl)-amino-, and tetrahydropyran-4-yl-methyl-amino-;

$R^3$ is selected from the group consisting of phenyl, 4-methylphenyl, 3,5-di(trifluoromethyl)phenyl, —$CH_2$-phenyl, —$CH_2$-(3-iodophenyl), —$CH_2$-(4-iodophenyl), —$CH_2$-(4-cyanophenyl), —$CH_2$-(4-nitrophenyl), —$CH_2$-(4-aminophenyl), —$CH_2$-(3-methoxyphenyl), —$CH_2$-(4-(amino-carbonyl)-phenyl), —$CH_2$-(4-(cyclohexyl-amino-carbonyl)-phenyl), —$CH_2$-(4-(phenyl-amino-carbonyl)-phenyl), —$CH_2$-(4-(dimethyl-amino-carbonyl)-phenyl), —$CH_2$-(4-(morpholin-4-ylcarbonyl)-phenyl), —CH$_2$-(4-(pyrrolidin-1-yl-carbonyl)-phenyl), —CH$_2$-(4-(methyl-sulfonyl-amino)-phenyl), —CH$_2$-(4-(pyrid-2-yl-sulfonyl-amino)-phenyl), —CH$_2$-(4-(methyl-carbonyl-amino)-phenyl), —CH$_2$-(pyrid-3-yl), —CH$_2$-(pyrid-4-yl), —CH$_2$-(4-(phenyl)-phenyl), —CH$_2$-(4-(4-cyanophenyl)-phenyl), —CH$_2$-(4-(3-methoxyphenyl)-phenyl), —CH$_2$-(4-(2-methyl-carbonyl-amino-phenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl), —CH$_2$-(4-(tetrazol-5-yl)-phenyl) and —CH$_2$-(4-(benzo[d][1,3]dioxol-5-yl)-phenyl);

and wherein the starred stereo-center is present in an enantiomeric excess of the (S)-stereo-configuration;

or a pharmaceutically acceptable salt thereof.

8. A compound as in claim 4, wherein

R$^1$ is —CH$_2$-(thien-2-yl);

R$^2$ is selected from the group consisting of cyclohexyl-amino, cyclohexyl-methyl-amino-, trans-(1-(4-methoxycarbonyl-cyclohexyl)-amino)-, N-methyl-N-(cyclohexyl-methyl)-amino-, and tetrahydropyran-4-yl-methyl-amino-;

R$^3$ is selected from the group consisting of phenyl, 4-methylphenyl, —CH$_2$-phenyl, —CH$_2$-(4-iodophenyl), —CH$_2$-(4-cyanophenyl), —CH$_2$-(4-nitrophenyl), —CH$_2$-(4-(amino-carbonyl)-phenyl), —CH$_2$-(4-(cyclohexyl-amino-carbonyl)-phenyl), —CH$_2$-(4-(phenyl-amino-carbonyl)-phenyl), —CH$_2$-(4-(morpholin-4-yl-carbonyl)-phenyl), —CH$_2$-(4-(methyl-sulfonyl-amino)-phenyl), —CH$_2$-(4-(pyrid-2-yl-sulfonyl-amino)-phenyl), —CH$_2$-(4-(methyl-carbonyl-amino)-phenyl), —CH$_2$-(pyrid-4-yl), —CH$_2$-(4-(phenyl)-phenyl), —CH$_2$-(4-(4-cyanophenyl)-phenyl), —CH$_2$-(4-(3-methoxyphenyl)-phenyl), —CH$_2$-(4-(3-methyl-carbonyl-amino-phenyl)-phenyl), —CH$_2$-(4-(pyrid-3-yl)-phenyl), —CH$_2$-(4-(pyrid-4-yl)-phenyl), —CH$_2$-(4-(2-methoxy-pyrdi-3-yl)-phenyl), —CH$_2$-(4-(6-methoxy-pyrid-3-yl)-phenyl), —CH$_2$-(4-(2-chloro-pyrid-3-yl)-phenyl), —CH$_2$-(3-(6-hydroxy-pyrid-3-yl)-phenyl), —CH$_2$-(4-(6-hydroxy-pyrid-3-yl)-phenyl), —CH$_2$-(3-(pyrimidin-5-yl)-phenyl), —CH$_2$-(4-(pyrimidin-5-yl)-phenyl) and —CH$_2$-(4-(benzo[d][1,3]dioxol-5-yl)-phenyl);

and wherein the starred stereo-center is present in an enantiomeric excess of the (S)-stereo-configuration;

or a pharmaceutically acceptable salt thereof.

9. A compound as in claim 4, wherein

R$^1$ is selected from the group consisting of fur-2-yl-methyl- and thien-2-yl-methyl;

R$^2$ is selected form the group consisting of cyclohexyl-methyl-amino- and cyclohexyl-amino-;

R$^3$ is selected from the group consisting of —CH$_2$-(pyrid-3-yl) and —CH$_2$-(4-(phenyl)-phenyl);

and wherein the starred stereo-center is present in an enantiomeric excess of the (S)-stereo-configuration;

or a pharmaceutically acceptable salt thereof.

10. A compound as in claim 4, wherein R$^1$ is —CH$_2$-(thien-2-yl); R$^2$ is selected from the group consisting of cyclohexyl-amino, cyclohexyl-methyl-amino-, trans-(1-(4-methoxycarbonyl-cyclohexyl)-amino)- and N-methyl-N-(cyclohexyl-methyl)-amino-; R$^3$ is selected from the group consisting of phenyl, 4-methylphenyl, —CH$_2$-(4-cyanophenyl), —CH$_2$-(4-nitrophenyl), —CH$_2$-(4-(pyrid-2-yl-sulfonyl-amino)-phenyl), —CH$_2$-(4-(pyrid-4-yl)-phenyl), —CH$_2$-(4-(6-methoxy-pyrid-3-yl)-phenyl), —CH$_2$-(4-(6-hydroxy-pyrid-3-yl)-phenyl) and —CH$_2$-(4-(pyrimidin-5-yl)-phenyl); and wherein the starred stereo-center is present in an enantiomeric excess of the (S)-stereo-configuration; or a pharmaceutically acceptable salt thereof.

11. A compound as in claim 1, wherein the starred stereo-center is present in an enantiomeric excess of the (S)-stereo-configuration.

12. A pharmaceutical composition comprising a pharmaceutically acceptable carrier and a compound of claim 1.

13. A pharmaceutical composition made by mixing a compound of claim 1 and a pharmaceutically acceptable carrier.

14. A process for making a pharmaceutical composition comprising mixing a compound of claim 1 and a pharmaceutically acceptable carrier.

* * * * *